US00RE34504E

United States Patent [19]

Uehara et al.

[11] E Patent Number: Re. 34,504

[45] Reissued Date of Patent: Jan. 11, 1994

[54] ELECTRONIC ENDOSCOPE SYSTEM PROVIDED WITH A MEANS OF IMAGING FROZEN PICTURES HAVING FEW PICTURE IMAGE SMEARS

[75] Inventors: Masao Uehara; Mashide Kanno; Katsuyuki Saito; Akinobu Uchikubo; Katsuyoshi Sasagawa; Shinji Yamashita; Akira Kusumoto; Kazunari Nakamura, all of Hachioji, Japan; Shinichiro Hattori; Keiichi Hiyama, both of Akishima; Jun Hasegawa, Hino; Masahiko Sasaki; Takehiro Nakagawa, both of Hachioji, all of Japan

[73] Assignee: Olympus Optical Co., Ltd., Tokyo, Japan

[21] Appl. No.: 597,906

[22] Filed: Oct. 11, 1990

Related U.S. Patent Documents

Reissue of:

[64] Patent No.: 4,901,143
Issued: Feb. 13, 1990
Appl. No.: 311,510
Filed: Feb. 16, 1989

[30] Foreign Application Priority Data

| | | | |
|---|---|---|---|
| Feb. 16, 1988 | [JP] | Japan | 63-31809 |
| May 6, 1988 | [JP] | Japan | 63-109187 |
| Aug. 12, 1988 | [JP] | Japan | 63-199791 |
| Aug. 19, 1988 | [JP] | Japan | 63-206804 |
| Aug. 23, 1988 | [JP] | Japan | 63-209677 |
| Oct. 14, 1988 | [JP] | Japan | 63-259917 |
| Oct. 27, 1988 | [JP] | Japan | 63-272833 |
| Nov. 11, 1988 | [JP] | Japan | 63-286322 |

[51] Int. Cl.[5] ..... A61B 1/04; A61B 1/06

[52] U.S. Cl. ..... 358/98; 128/6; 358/105; 358/222

[58] Field of Search ..... 358/98, 105, 222; 128/6; H04N 7/18

[56] References Cited

U.S. PATENT DOCUMENTS

| | | | |
|---|---|---|---|
| 4,410,914 | 10/1983 | Siau | 358/222 |
| 4,476,494 | 10/1984 | Tugayé | 358/222 |

FOREIGN PATENT DOCUMENTS

| | | |
|---|---|---|
| 61-071790 | 4/1986 | Japan . |
| 61-071791 | 4/1986 | Japan . |
| 63-053531 | 3/1988 | Japan . |
| 63-129329 | 6/1988 | Japan . |
| 63-129331 | 6/1988 | Japan . |
| 63-167576 | 7/1988 | Japan . |

*Primary Examiner*—Howard W. Britton
*Attorney, Agent, or Firm*—Armstrong, Westerman, Hattori, McLeland & Naughton

[57] ABSTRACT

There is provided a frozen picture memorizing memory holding as a frozen picture image a picture image signal imaged by an electronic endoscope. By the operation of a frozen picture directing switch, whether the frozen picture is adapted to the memorizing condition or not is judged through a picture image movement detecting circuit. In case it is judged to be adapted to the memorizing condition, the picture image signal is memorized actually as a frozen picture image to obtain a clear frozen picture having little color smear and fogging.

70 Claims, 68 Drawing Sheets

| | Sig 1 | Sig 2 |
|---|---|---|
| 0 | GND | GND |
| 1 | GND | Vcc |
| 2 | Vcc | GND |
| 3 | Vcc | Vcc |

ELECTRONIC ENDOSCOPE SYSTEM PROVIDED WITH A MEANS OF IMAGING FROZEN PICTURES HAVING FEW PICTURE IMAGE SMEARS

Matter enclosed in heavy brackets [ ] appears in the original patent but forms no part of this reissue specification; matter printed in italics indicates the additions made by reissue.

BACKGROUND OF THE INVENTION

1. Field of the Invention and Related Art Statement: This invention relates to electronic endoscope systems wherein clear frozen pictures having few color smears can be obtained.

Recently, there is developed an endoscope imaging apparatus wherein such solid state imaging device as a CCD is provided at the tip of an endoscope, a body cavity interior is illuminated sequentially with three colors of red, green and blue, the picture image of the body cavity interior is color-imaged and a diagnosis is made on the basis of the color picture image displayed in a monitor apparatus. In this system, as it is necessary to image component picture images of three colors in order to image one color picture image, time will be taken and color smears of the picture image will be likely to be generated by the movement of the object being imaged and the hand vibration.

As a means of preventing such color smears, it is suggested in the publication of Japanese Patent Application Laid Open No. 71790/1986 to provide a means of detecting color smears of picture images on the basis of a difference between the picture images imaged at different times by an imaging means so as to control the imaging speed of the imaging means in response to the output of this detecting means. According to this prior art example, the moving speed of the imaging means will vary in response to the moving speed of the object and, even in the case of a quickly moving object, color smears will be able to be prevented from being generated.

However, the color smear preventing means in the endoscope imaging apparatus in the above mentioned prior art example is to prevent color smears in moving picture images and has no means of obtaining frozen pictures.

When an endoscope picture image is displayed as a moving picture image as it is in a monitor apparatus, in case it is desired to diagnose details, the part to be noted will move unfavorably. Therefore, there are a freezing switch directing the displaying of a frozen picture and an apparatus whereby the subsequent picture image writing into a picture image memory is inhibited by this freezing switch so that a frozen picture image may be displayed on the monitor picture surface.

In such case, in the general prior art example, when a frozen picture image is directed by the above mentioned switch, on the basis of this direction, the freezing operation of the imaging means will be made unconditionally. Therefore, in case the freezing direction is made at the time when the object and the endoscope tip position are moving relatively, a color smear will be generated on the frozen picture. As such color smear makes the natural object image hard to see, the affected part or the like will be likely to be overlooked by the observer.

There has been a problem that, in order to obtain a frozen picture in which such color smear is not generated, such complicated operation as repeating the freezing direction and freezing release until a frozen picture in which there is no color smear is obtained is required.

On the other hand, in the publication of Japanese Patent Application Laid Open No. 71791/1986, the present assignee suggests an apparatus wherein a release switch is provided so that, in case the release switch is operated, a color smear and the like of a picture image memorized in a frame memory may be detected and, in case the color smear amount is large, the color smear may be corrected to be small.

This apparatus has defects that, as it is to process picture images to correct color smears, the apparatus is so large in the scale as to be hard to apply to general electronic endoscopes and that picture images can not be corrected in the peripheral parts.

OBJECTS AND SUMMARY OF THE INVENTION

An object of the present invention is to provide an electronic endoscope system which is simple in [the formation] *its construction* and whereby frozen picture image *having* few [in the] picture image smears and the like can be obtained.

Another object of the present invention is to provide an electronic endoscope whereby frozen pictures adapted to diagnoses can be obtained.

In the present invention, there are provided a picture image memorizing means memorizing photoelectrically converted picture image signals with an imaging device forming an electronic endoscope, a frozen picture directing means directing said picture image memorizing means to memorize frozen pictures, a movement detecting means detecting the movement amounts of picture image signals and a frozen picture memory controlling means memorizing actual frozen pictures by judged signals judged to be adapted to memorizing conditions by the judgment of the movement detecting means so that clear frozen pictures few in such picture image smears as color smears may be obtained with a simple formation.

The object to be imaged by an endoscope is mostly a living body which is often moving with the heart pulses and breaths of the examinee. The pulses and breaths have periods. At some timing, the object will be stationary or move very little. Therefore, at such time, a color smear or the like will be hardly generated. When such state is sensed by a movement detecting means and a frozen picture is actually written in by the sensing signal, a frozen picture small in the movement amount will be obtained. Therefore, without repeating the complicated operations of directing and releasing the frozen picture, a clear frozen picture can be easily obtained.

BRIEF DESCRIPTION OF THE DRAWINGS

FIG. 1 is a [formation] *schematic* view of an electronic endoscope system of the first embodiment.

FIG. 2 is a block diagram showing the formation of a color smear sensing means.

FIGS. 3 and 4 are views showing respectively the distributions of the green components and blue components of the respective pixels forming an endoscope picture image.

FIG. 5 is a block diagram showing another [formation] *schematic* example of a color smear sensing means.

FIG. 6 is a conceptional view showing the distribution of the values of the green components/blue components forming an endoscope picture image.

FIG. 7 is a view showing a variation with time within one field period of an output of a divider in FIG. 5.

FIG. 25 is a block diagram showing the formation of the system of the fifth embodiment.

FIG. 26 is a block diagram showing the formation of a video signal processing circuit.

FIG. 27 is a [formation] *schematic* view of a movement detecting circuit.

FIG. 28 is a circuit diagram of a level discriminating circuit.

FIG. 64 is an operation explaining view of the minimum value detecting circuit in FIG. 63a.

DETAILED DESCRIPTION OF PREFERRED EMBODIMENTS

Figure 1:
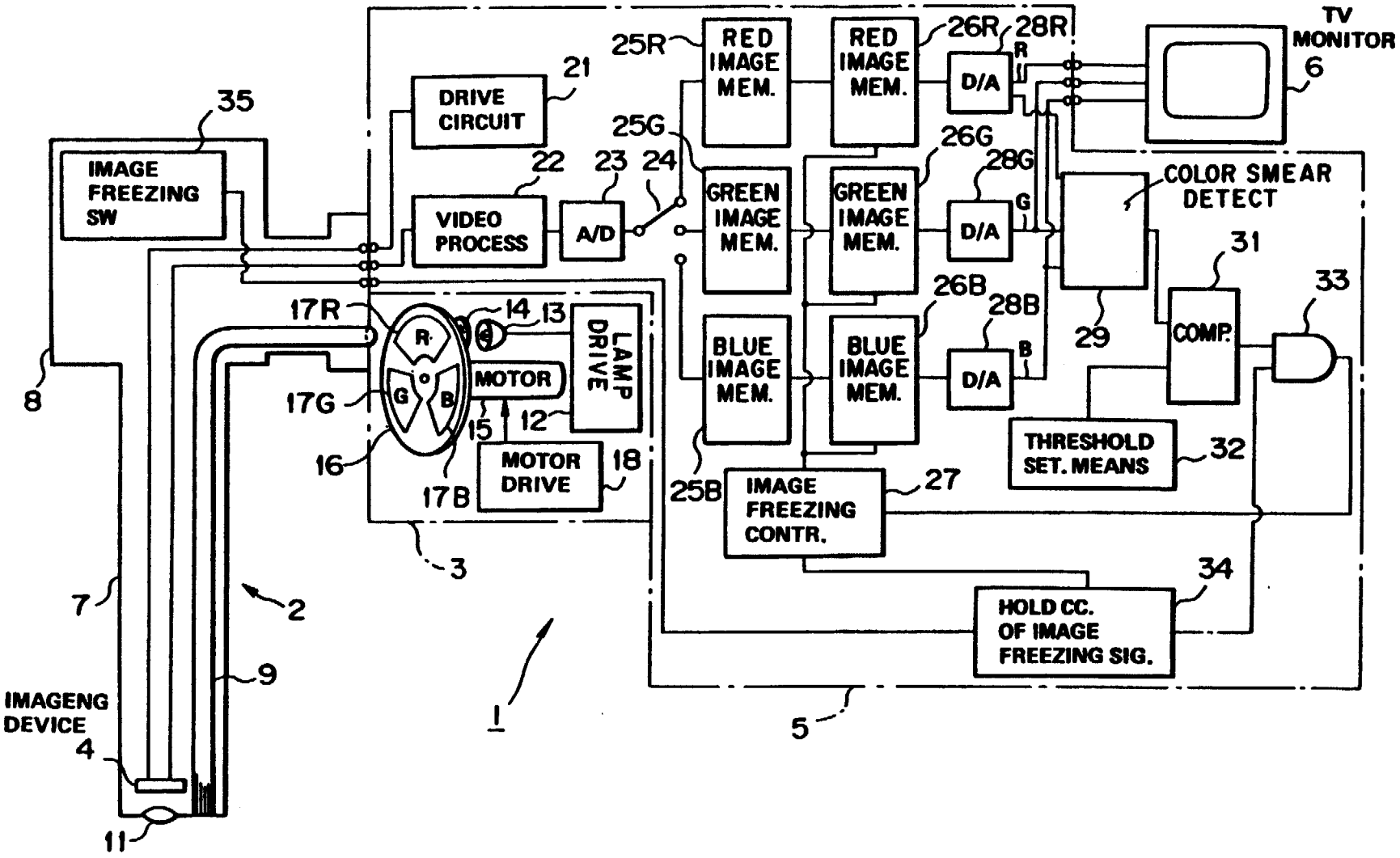
FIGS. 1 to 7 relate to the first embodiment of the present invention.

As shown in FIG. 1, an electronic endoscope system 1 of the first embodiment comprises an electronic endoscope 2, a light source apparatus 3 feeding an illuminating light to this electronic endoscope 2, a signal processing apparatus 5 for processing signals of an imaging device 4 contained in the electronic endoscope 2 and a TV monitor 6 displaying video signals output from this signal processing apparatus 5.

The above mentioned electronic endoscope 2 has an elongate insertable part 7 which can be inserted into a body cavity or the like and an operating part 8 is formed at the rear end of this insertable part 7. A light guide 9 formed of a glass fiber bundle is inserted through this insertable part 7 and is connected at the hand base side end to the light source apparatus 3 so that an illuminating light from the light source apparatus 3 may be fed to the light guide 9 at the end. The illuminating light is emitted from the exit end surface of the tip part of the insertable part 7 so as to illuminate an object to be imaged. An image of the illuminated object is formed on the imaging device 4 by an objective lens 11 provided in the tip part. This imaging device 4 photoelectrically converts the formed image and stores it as an electric charge.

Now, the above mentioned light source apparatus 3 is a frame sequential type light source apparatus sequentially outputting lights different in the wavelength. That is to say, a white color light of such lamp as a xenon lamp emitted by a lamp driving circuit 12 is condensed by a condenser lens 14 and is radiated to the end surface of the light guide 9 through respective layer-like red, green and blue color transmitting filters 17R, 17G and 17B fitted to a rotary wheel 16 rotated by a motor 15. That is to say, the light guide 9 sequentially illuminates the object with the lights of the respective wavelengths of red, green and blue. By the way, the motor 15 is rotated at a constant speed by a motor driving circuit 18.

When the illuminating periods by the lights of the respective wavelengths end, a driving signal from a driving circuit 21 will be applied to the imaging device 4, will be read out of the imaging device 4, will be amplified through a video processing circuit 22, will be then converted to a digital signal from an analogue signal by an A/D converter 23 and will be able to be input into picture image memories 25R, 25G and 25B for RED, GREEN and BLUE formed of semiconductor memories or the like through a switching switch 24. For example, the signal imaged under the light of the wavelength of red is written into the RED picture image memory 25R. Second picture image memories 26R, 26G and 26B are connected at the input ends respectively to the output ends of these picture image memories 25R, 25G and 25B. The picture image memories 25R, 25G and 25B are to output as synchronized color picture image signals the picture image signals of the respective color frames (or color fields) imaged by the frame sequential system.

The above mentioned picture image memories 26R, 26G and 26B are to memorize frozen pictures. In case the picture images of the picture image memories 25R, 25G and 25B are being written in and read out, the signals of moving picture images will be output and the writing in will be inhibited so that the picture images written in before this writing in may be output as frozen pictures. These picture image memories 26R, 26G and 26B are controlled by a picture image freezing controlling circuit 27.

The picture image data of the above mentioned picture image memories 26R, 26G and 26B are converted to analogue color signals R, G and B respectively by D/A converters 28R, 28G and 28B and are color-displayed on the monitor picture surface by the TV monitor 6. Also, the analogue color signals R, G and B are input into a color smear sensing means or detecting means 29 and the color smear amount or movement amount between the color signals R and G, G and B or B and R is detected and is output to one input end of a comparator 31. A threshold value corresponding to the allowable color smear amount is input into this comparator 31 at the other input end from a threshold value setting means 32 and is compared with the color smear amount output from the above mentioned color smear sensing means 29 and a comparison result signal, that is, a discriminating signal is output. When the color smear amount is smaller than this threshold value, an "H" discriminating signal will be output and will be input into an AND circuit 33. A gate signal is output to this AND circuit 33 from a picture image frozen signal holding circuit 34. During this gate period, if the above mentioned "H" discriminating signal is output, the discriminating signal will be input as a controlling signal freezing the picture image into the picture image freezing controlling circuit 27 through the AND circuit 33. When this discriminating signal (controlling signal) is input, this controlling circuit 27 will stop the subsequent picture image data writing into the picture image memories 26R, 26G and 26B and will control the output of the picture image data of the frozen pictures from the picture image memories 26R, 26G and 26B.

Now, the gate signal of the above mentioned picture image freezing signal holding circuit 34 is generated by the operation of a picture image freezing switch 35 provided in the operating part of the electronic endoscope 2.

That is to say, when this switch 35 is operated, a gate signal will be output from the picture image freezing signal holding circuit 34, the AND circuit 33 will be opened and a signal judging whether the picture image is small in the color smear amount in the comparator 31 will be passed to the picture freezing controlling circuit 27. At the timing of judging the color smear amount to be smaller than the threshold value, the picture image freezing controlling circuit 27 is set in a frozen picture displaying (frozen picture reading out) mode in which the picture image memories 26R, 26G and 26B are prohibited from having data written in and the picture image data written in before then are repeatedly read out. Therefore, at the timing when the picture image becomes small in the color smear amount after the above mentioned switch 35 is operated, a frozen picture image can be displayed in the TV monitor 6.

Figure 2:
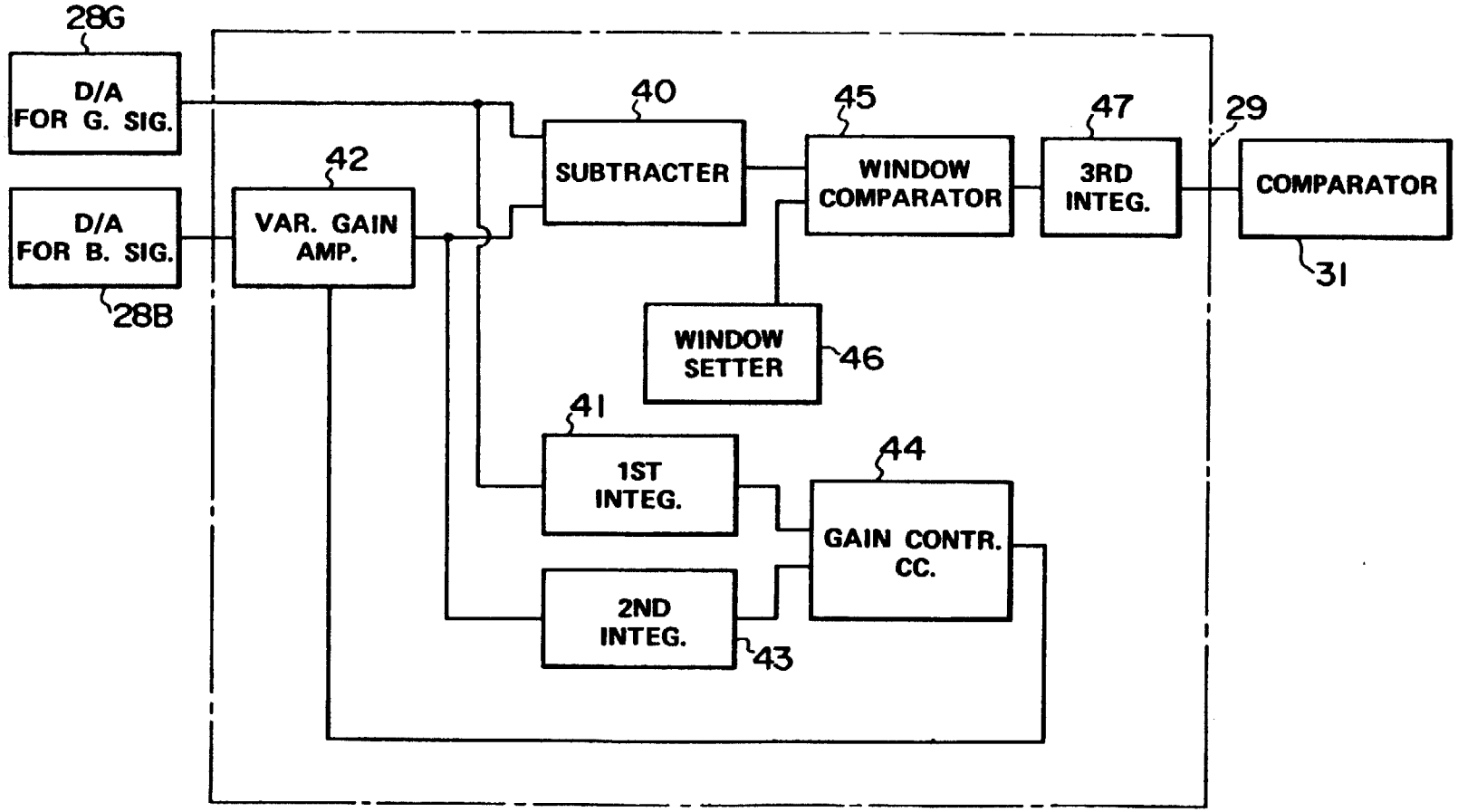

Now, the concrete formation of the above mentioned color smear detecting *circuit* 29 is shown in FIG. 2.

Figure 3:
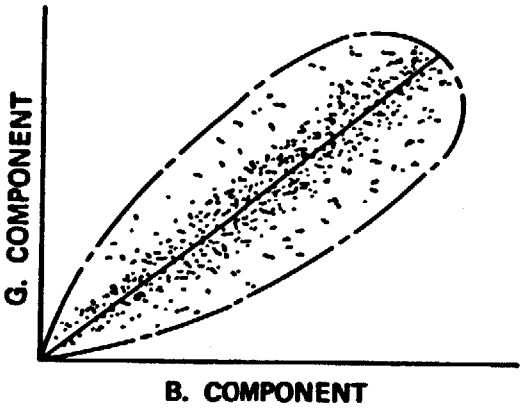

The relation between the green (G) components and blue (B) components of an ordinary endoscope picture image is investigated to be as shown in FIG. 3. It is found from this graph that the G components and B components of the respective pixels forming the endoscope picture image are dispersed in a limited range with a linear function as a center. The dispersion is different depending on the object but most pixels are present near the straight line in the center. Therefore, the ratio of the G components to the B components of most pixels of the ordinary endoscope picture image may be considered to be substantially constant.

Figure 4:
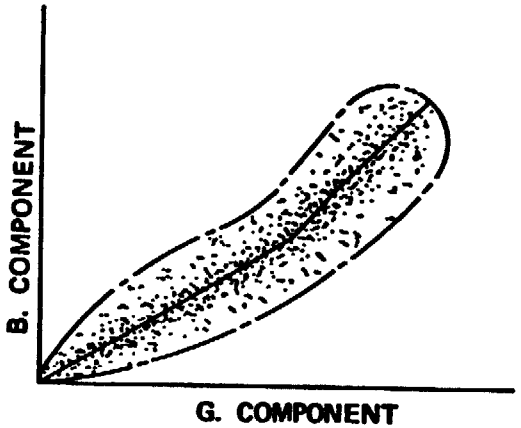

In some [object] *objects*, as shown in FIG. 4, the G components and B components may be distributed like a bent line. However, they are like a simple bent line. In considering the range of the sizes of the pixel data as sectioned, the ratio of the G components to the B components can be said to be substantially constant.

The formation shown in FIG. 2 is to sense color smears from the picture image signals of green and blue on the basis of the above mentioned fact. That is to say, the output of a D/A converter 28G is input into a subtracter 40 at one input end and is input into a first integrator 41. On the other hand, the output of a D/A converter 28B is input into the subtracter 40 at the other input end through a variable gain amplifier 42 and is input into a second integrator 43. The respective outputs of the first integrator 41 and second integrator 43 are input into a gain controlling circuit 44 controlling the gain of the variable gain amplifier 42. The output end of the gain controlling circuit 44 is connected to the gain controlling input end of the variable gain amplifier 42.

The subtracter 40 is connected at the output end to a window comparator 45 to which is connected a window setter 46 for setting a window. A window comparator 45 is connected at the output end to a third integrator 47. The output of [a comparator] *the integrator* 47 is input into the above mentioned comparator 31 as an output of the color smear detecting means 29.

The color smear preventing operation of the thus formed electronic endoscope system 1 shall be explained in the following and then the operation of the color smear detecting means 29 in FIG. 2 shall be explained.

A white color light radiated from the lamp 13 passes through the color filter disc 16 rotated and driven by the motor 15 so as to be color sequential lights of R, G and B which enter one end surface of the light guide 9 of the electronic endoscope 2. The color sequential lights having entered the end surface of the light guide 9 are transmitted through the light guide 9, reach the tip of the electronic endscope 2 and are emitted from the other end surface of the light guide 9. The emitted color sequential lights illuminate such object as a stomach wall and the image of the object is formed on the imaging device 4 by the objective lens 11. The imaging device 4 is driven by the driving circuit 21 and its output is made a video signal by the video processing circuit 22.

The output of the video processing circuit 22 is digitalized by the A/D converter 23 and the digital picture image data are input and recorded respectively into the picture image memories 25R, 25G and 25B while being switched for the respective R, G and B component picture image data by the switching switch 24. By the way, the switching switch 24 is operated to be switched sequentially in response to the light colors of the color sequential lights as synchronized with the rotation of the color filter disc 16.

Then the respective picture image data recorded in the picture image memories 25R, 25G and 25B are transferred at a high speed to the picture image memories 26R, 26G and 26B. This transferring operation is made by utilizing the synchronized signal period of the television. The picture image data transferred to the picture image memories 26R, 26G and 26B are read out as synchronized with the synchronized signal of the television, are converted to analogue signals by the D/A converters 28R, 28G and 28B and are displayed in the TV monitor 6. Usually, as the above mentioned transfer is made for each frame, moving picture images will be observed in the TV monitor 6.

In case the picture image is observed as frozen, the operator will push the picture image freezing switch 35 to direct freezing. When this picture image freezing switch 35 is pushed to operate, a picture image freezing directing signal will be transmitted to the picture image freezing signal holding circuit (or holding circuit of image freezing signals) 34. Even after the picture image freezing switch 35 pushing operation is released, the above mentioned freezing directing signal will be held in the picture image freezing signal holding circuit 34.

On the other hand, the respective outputs of the above mentioned D/A converters 28G and 28B are input into also the color smear detecting means 29 in which the color smear amount for each frame is detected. This color smear amount is compared by the comparator 31 with the value set in advance by the threshold value setting means 32. When the color smear amount is below a set constant value, the comparator 31 will output a true value to the AND circuit 33 at one input end. The output of the above mentioned picture image freezing signal holding circuit 34 is input into the AND circuit 33 at the other input end. Only in case both of the outputs of the comparator 31 and picture image freezing signal holding circuit are true values, the AND circuit 33 will deliver a frozen picture displaying controlling signal to the picture image freezing controlling circuit 27.

The picture image freezing controlling circuit 27 receives this controlling signal and stops at a proper timing the transfer of the picture image data to the picture image memories 26R, 26G and 26B from the picture image memories 25R, 25G and 25B. As a result, frozen pictures will be recorded in the picture image memories 26R. 26G and 26B and will be observed in the TV monitor 6.

In such case, the observed frozen pictures are frozen pictures in which the color smear is below a certain value and is not substantially generated and which are easy to see.

In order to release the picture image freezing, the picture image freezing signal holding circuit 34 may be reset with a release switch not illustrated or may be toggle-operated with the picture image freezing switch 35.

As described above, the object to be imaged with an endoscope is mostly a living body and is mostly moving with the heart pulses and breaths of the examinee. At a [timing] *certain time*, the object will be stationary or will move very little. Therefore, as in the above mentioned embodiment, if the color smear amount is watched with the color smear detecting means 29, the state in which the object is stationary or moves very little and the color smear amount is below a certain value is detected and the picture image is frozen at this time, a frozen picture in which the influence of the color smear is practically removed will be able to be obtained.

Therefore, if the picture image freezing switch 35 is operated in a state that the noted part can be displayed on the picture surface of the TV monitor 6, at the time when the color smear is little, a frozen picture having little color smear will be able to be displayed on the picture surface of the TV monitor 6 and will be very useful in the case of diagnosing.

The operation of the color smear sensing means shown in FIG. 2 shall be explained in the following.

First of all, the output of the D/A converter 26G is integrated for one field or one frame period by the integrator 41. On the other hand, the output of the D/A converter 26B is amplified by the variable gain amplifier 42 and is then integrated for one field or one frame period by the integrator 43. The respective outputs of the integrators 41 and 43 are compared with each other in the gain controlling circuit 44. The output of this gain controlling circuit 44 controls the gain of the variable gain amplifier 42 so that the respective outputs of both integrators 41 and 43 may be equal to each other.

As a result, though the G components are higher in the level than the B components in an ordinary endoscope picture image, the G components and B components of the picture image signal input into the subtracter 40 are equal to each other in the integrated value within the field or frame period. The subtracter outputs the difference between the outputs of the D/A converter 26G and the variable gain amplifier 42. In case no color smear is produced, in most pixels, the output of the subtracter 40 will be substantially 0, that is to say, the values obtained by multiplying the [C] *G* components and B components by the gain of the variable gain amplifier 42 will be equal to each other. On the contrary, in case a color smear is produced, in less pixels than in the above, the output of the subtracter 40 will be [substantially] *a value other than* 0.

When only the pixel signals in which the output of the subtracter 40 is near 0 are extracted by the window comparator 45 and are integrated by the integrator 47 over the entire picture surface, the color smear amount over the entire picture surface will be obtained. Therefore, the output of the integrator 47 shows a color smear amount and therefore, when this output is input into the comparator 31, a controlling signal to the picture image freezing controlling circuit 27 will be able to be obtained.

Figure 5:
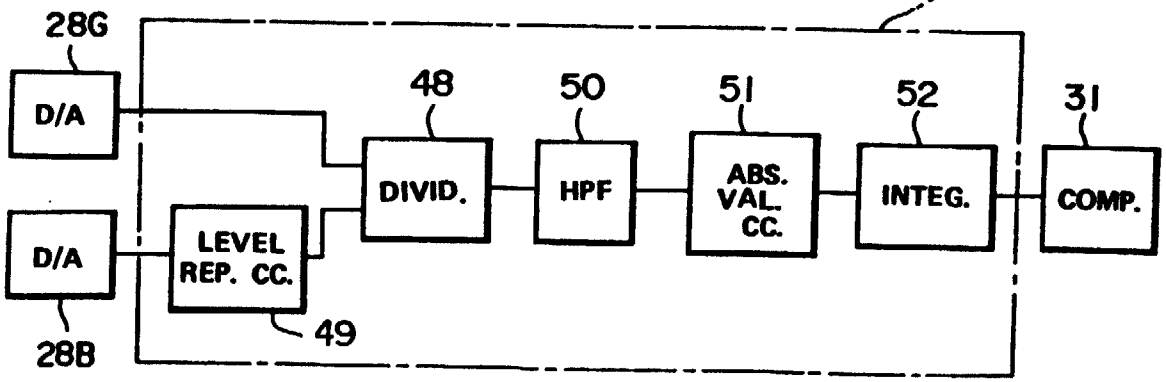
Figure 6:
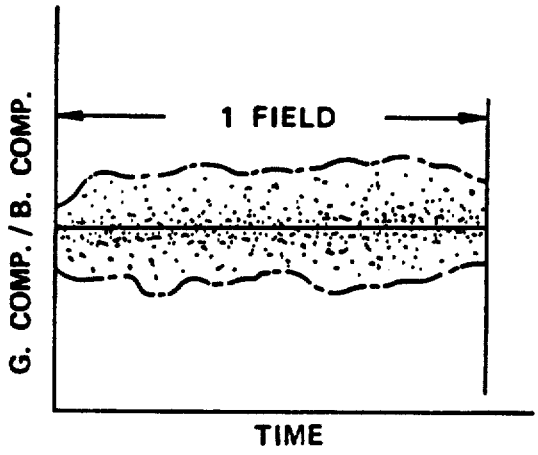

FIG. 5 is a block diagram showing another formation of the color smear detecting means 29. The output of the D/A converter [26G] *28G* is input into a divider 48 at one input end. On the other hand, the output of the D/A converter [26B] *28B* is input into the above mentioned divider 48 at the other input end through a level replacing circuit 49 outputting other values than 0 when the input is 0. The divider 48 is connected at the output end to a high pass filter 50 intercepting direct current components and passing only alternating current components. The output of the high pass filter 50 is input into an absolute value circuit 51 formed of a rectifying circuit or the like. The output of the absolute value circuit 51 is input into an integrator 52 making an integrating operation only in one field or one frame period. The output of this integrator 52 is input into the comparator 31 as the output of the color smear detecting means 29.

The operation of the thus formed color smear detecting means 29 shall be explained in the following. The output of the D/A converter [26B] *28B* will be replaced with a value near 1 only in case the value is near 0 by a level replacing circuit 49. This is to prevent the denominator of the divider 48 from being near 0. In the divider 48, (G components)/(B components) is calculated. As clear also from the above described FIGS. 3 and 4, the value of (G components)/(B components), that is, the gradient of the linear function in FIG. 3 is dispersed with a constant value in the center and this dispersion shows the state of the color smear.

Figure 7:
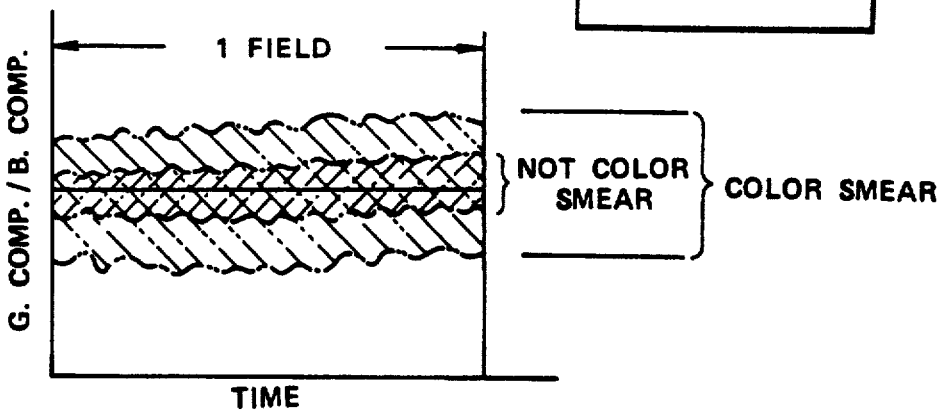

FIG. 7 shows the variation with time within one field period of the output of the divider 48. When no color smear is generated, the dispersion will be little but, when a color smear is generated, the dispersion will be much. This dispersion is taken out in the form of alternating current components by the high pass filter 50 and its amount is integrated over the entire picture surface by the absolute value circuit 51 and integrator 52. The output of this integrator 52 shows the color smear amount and is input into the comparator 31 to obtain a picture image freezing controlling signal.

By the way, in the above mentioned first embodiment, there is an advantage that, as the switch 35 directing to freeze picture images is provided in (the operating part 8 of) the electronic scope 2, in case it is desired to obtain a frozen picture, the operation will be able to be easily made.

Figure 8:
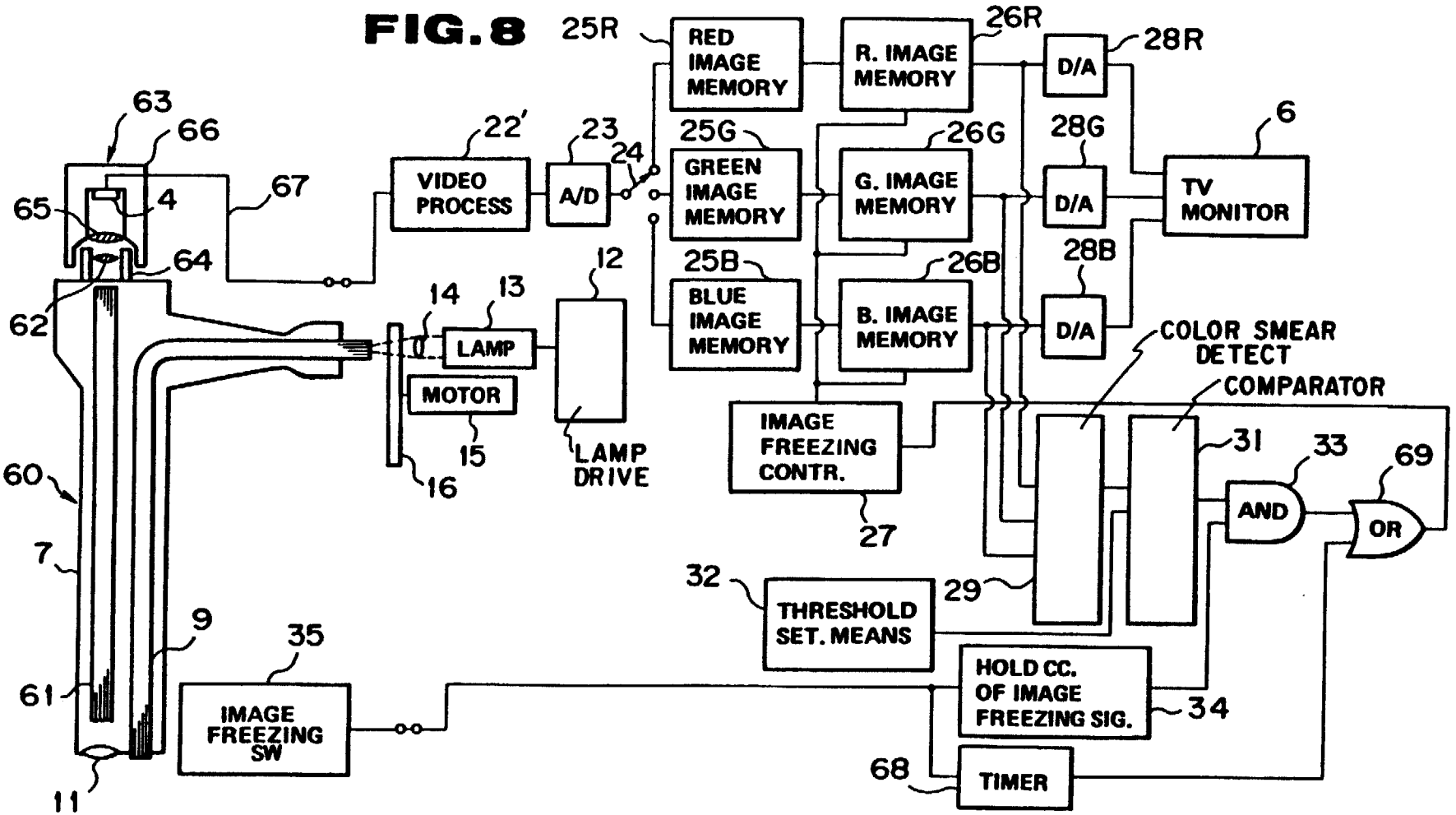
FIG. 8 is a block diagram showing the formation of a system of a modification of the first embodiment.

FIG. 8 is a block [formation] *schematic* diagram showing a modification of the first embodiment. The same or similar component members as in the embodiment shown in FIG. 1 are represented by attaching the same reference numerals. In FIG. 8, the reference numeral 60 represents a general fiber scope formed of an objective lens 11, light guide 9, image guide 61 and eyepiece lens 62. The reference numeral 63 represents a color sequential type TV camera head removably fitted to the eyepiece part 64 of the above mentioned fiber scope 60 and formed of an image forming lens 65, imaging device 4 and camera 66. The imaging device 4 is arranged in an image forming position on the end surface of the above mentioned image guide 61 by the image forming lens 5. The imaging device 4 is connected to a video processing circuit 22' through a connecting cord 67. (Here the driving circuit 21 and video processing circuit 22 as combined are represented by 22'.)

The same as in the embodiment shown in FIG. 1, the light from the lamp 13 driven by the lamp driving circuit 12 is condensed on one end surface of the light guide 9 through the condenser lens 14 and the color filter disc 16 rotated and driven by the motor 15. The reference numeral 35 represents a picture image freezing switch formed of a foot switch and connected to a picture image freezing signal holding circuit 34 formed of a latch or the like and to a timer 68.

The output of the above mentioned video processing circuit 22' is A/D-converted by the A/D converter 23 and is input and recorded into the picture image memories 25R, 25G and 25B through the switching switch 24. The picture image memories 25R, 25G and 25B are further connected at the respective output ends respectively to the picture image memories 26R, 26G and 26B. The respective outputs of the picture image memories 26R, 26G and 26B are input respectively into the D/A converters 28R, 28G and 28B and also into the color smear detecting means 29 formed of a digital correlator and others.

The respective outputs of the D/A converters 28R, 28G and 28B are input into the TV monitor 6. The output of the color smear detecting means 29 is input into the comparator 31 at one input end. The threshold value setting means 32 is connected to the comparator 31 at the other input end. The outputs of the comparator 31 and picture image freezing signal holding circuit 34 are input into the AND circuit 33. The outputs of the AND circuit 33 and timer 68 are input into an OR circuit 69. The output of the OR circuit 69 is input into the picture image freezing controlling circuit 27. The same as in the above described embodiment, the picture image freezing controlling circuit 27 is connected at the output end to the picture image memories 26R, 26G and 26B at the respective picture image freezing controlling terminals.

The operation of this embodiment is substantially the same as of the embodiment shown in FIG. 1. However, the differences are as follows. The picture image of the object is formed on the imaging device 4 through the objective lens 11, image guide 61, eyepiece lens 62 and image forming lens 65 and its output signal is input into the video processing circuit 22'. As the picture image freezing switch 35 is formed of a foot switch, the picture image freezing is instructed by operating this switch with a foot. As the color smear sensing means 29 is connected to the picture image memories 26R, 26G and 26B, digital picture image data are input directly into this color smear sensing means 29. Therefore, in this color smear sensing means 29, the same processing as in the color smear sensing means shown in FIG. 2 or 5 is digitally made.

The timer 68 is to cope with the case that, even when a fixed time has elapsed after the picture image freezing switch 35 is operated to instruct freezing, the color smear of the imaged picture image will not reduce and the picture image freezing controlling signal will not be output from the comparator 31. A signal replacing this controlling signal is output from this timer 68 after a fixed time elapses and the picture image freezing controlling circuit 27 is forcibly driven through the OR circuit 69 to freeze the picture image to obtain a frozen picture.

By the way, in this embodiment, the threshold value $V_{th}$ of the threshold value setting means 32 can be varied, for example, by a variable resistance VR. Thus, the operator can freely set the color smear amount of the frozen picture. For example, in case a frozen picture clearer than a frozen picture obtained at a set value is desired, it may be varied by the variable resistance VR. Also, even the case that the desired color smear amount is different between the case of imaging the noted object near it and the case of imaging it far from it can be coped with. Further, even in the case that the imaging condition is different between the case of the electronic scope and the case of the television camera, a threshold value adapted to the respective cases can be set.

Now, in the color smear detecting means shown in FIGS. 2 and 5, the picture image is integrated over the entire picture surface by the integrators 41, 43, 47 and 52. However, in an ordinary electronic endoscope, as shown by the hatching in FIG. 9, the endoscope picture image part 70 is a [part] *portion of the entire picture image*. Therefore, in making various integrations in the above mentioned respective integrators 41, etc., it is necessary to integrate no pixel other than in the endoscope picture image part. For that purpose, a mask signal showing the endoscope picture image part 70 may be generated to control the function of the integrators. Instead of generating the mask signal, the contributing part by the part other than the endoscope picture image part 70 may be subtracted from the outputs of the integrators.

Further, the color smear may not be sensed over the entire endoscope picture image but may be sensed, for example, only in the picture image central part or on specific scanning lines. In such case, a proper mask signal may be generated and the color smear may be sensed only in a specific region.

Figure 10:
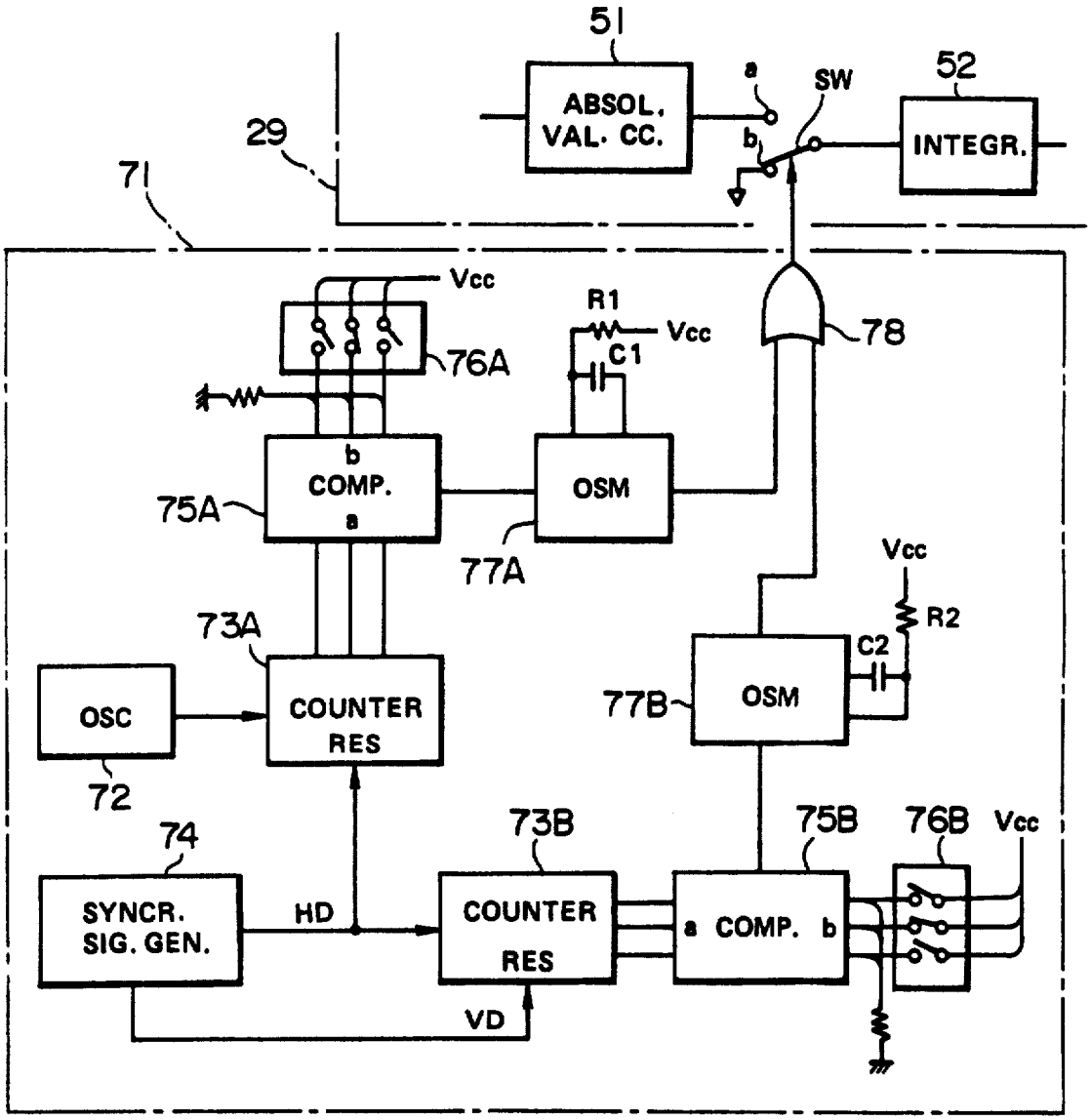
FIG. 10 is a block diagram showing the formation of a mask signal generating circuit determining the range of sensing color smears.

An example of a mask signal generating circuit 71 for sensing a color smear in a part of an endoscope picture image is shown in FIG. 10.

A clock CLK of a reference clock generator 72 is input into a first counter 73A, is preset by a horizontal synchronized signal HD of a synchronized signal generator 74 and then starts counting. The output of this counter 73A is input into a digital comparator 75A at the input ends on one side and this comparator 75A at the input ends b on the other side can variably set the set values by a dip switch 76A.

When the output of the counter A reaches this set value, the output of the comparator 75A will become "H", a one-shot multivibrator 77A will be triggered and pulses of a pulse width set by a condenser C1 and resistance R1 will be output. The output of this one-shot multivibrator 77A controls the switching of a switch SW provided between the absolute value circuit 51 and integrator 52 of the color smear sensing means 29 shown in FIG. 5 through an OR circuit 78.

The horizontal synchronized signal HD is input into a second counter 73B. The output of this counter 73B is input into a second comparator 75B and is compared with the set value of a dip switch 76B. The output of this comparator 75B is input into a second one-shot multivibrator 77B to trigger this one-shot multivibrator 77B. This one-shot multivibrator 77B outputs pulses of a width set by a resistance R2 and condenser C2. These pulses switch a switch SW through an OR circuit 78. By the way, the counter 73B is reset by a vertical synchronized signal VD.

Figure 11:
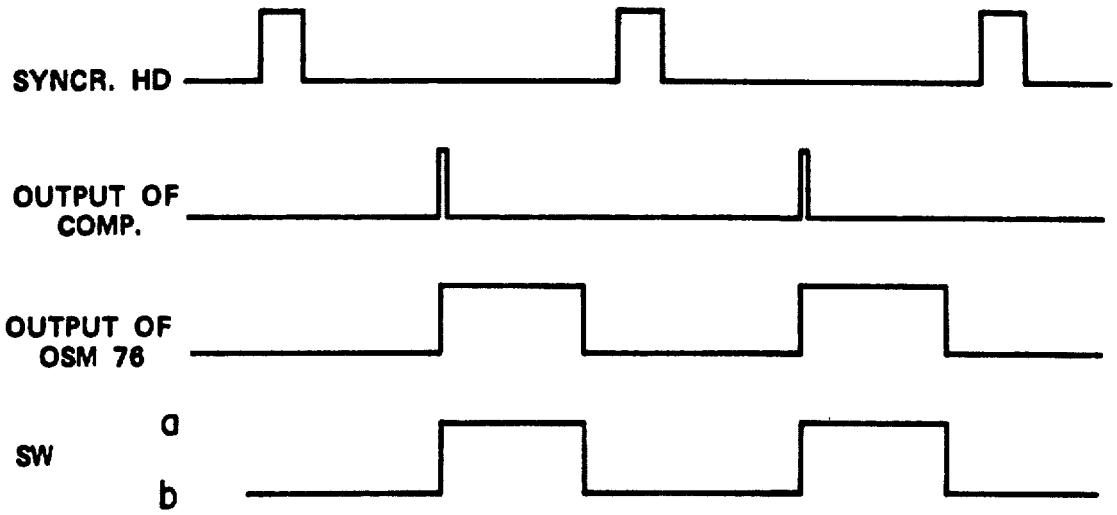
FIG. 11 is a view for explaining the operation in FIG. 10.

The operation of this signal generating circuit 71 is as shown in FIG. 11.

After being reset by the respective horizontal synchronized signals HD in FIG. 11, the counter 73A counts the [clocks] *clock pulses* CLK *of the clock generator 72*. When the counted value of this counter 73A reaches a set value, the comparator 75A will output a coinciding signal, will start the one-shot multivibrator 77A and will output pulses. By these pulses, the switch SW is switched to the contact a side from the contact b. Only in the period when these pulses are output, the integrator 52 will operate to integrate the output of the absolute value circuit 51.

The above mentioned explanation is of the operation of detecting color smears only in a period of a part within the respective horizontal periods and color smears are detected only in a period of a part in the respective vertical periods by the counter 73B, comparator 75B and one-shot multivibrator 77B.

Figure 9:
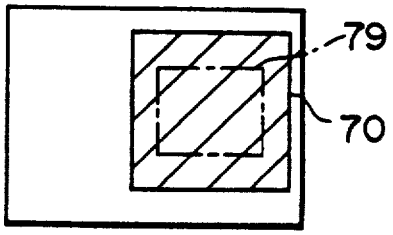
FIG. 9 is an explanatory view showing that an endoscope picture image is displayed in a part of a monitor picture surface.

Thus, color smears can be detected, for example, in a part 79 (indicated by the one-point chain lines) of the endoscope picture image 70 in FIG. 9.

The timing when pulses are output by the above mentioned dip switch 76A can be variably set. Also, for example, if the resistance R1 of the one-shot multivibrator 77A is varied, the pulse width will be able to be variably set. At the same time, the range of the color smear sensing operation in the vertical direction can be variably set by the dip switch 76B and resistance R2.

In the smear detecting means shown in FIGS. 2 and 5, a color smear is sensed by utilizing green (G) components and blue (B) components. However, the invention is not limited to this. The color smear may be sensed by using any other color [component] *components of the* picture image.

For example, red (R) components and green (G) components may be utilized or red (R) components and blue (B) components may be utilized. Also, as in the modification shown in FIG. 12, color smears may be sensed, for example, by using picture image components imaged by red and green and picture image components imaged by green.

In the system of this modification, a red and green color transmitting filter 17(R+G) is used instead of the green color transmitting filter 17G in the system in FIG. 1. Therefore, the green picture image memories 25G and 26G in FIG. 1 become red+green picture image memories 25(R+G) and 26(R+G) and a D/A converter 28(R+G) is indicated instead of the D/A converter 28G. The output of this D/A converter 28(R+G) becomes a red+green color signal R+G. This color signal R+G and the color signal G are input into the color smear detecting means 29. This color signal (R+G) has the red color signal R subtracted by a subtracter and a green color signal G is Produced and is input together with the red and blue color signals R and B into the monitor 6.

The above mentioned detecting means 29 provided with the mask signal generating circuit 71 in FIGS. 2, 5 and 10 can be used as it is.

Figure 12:
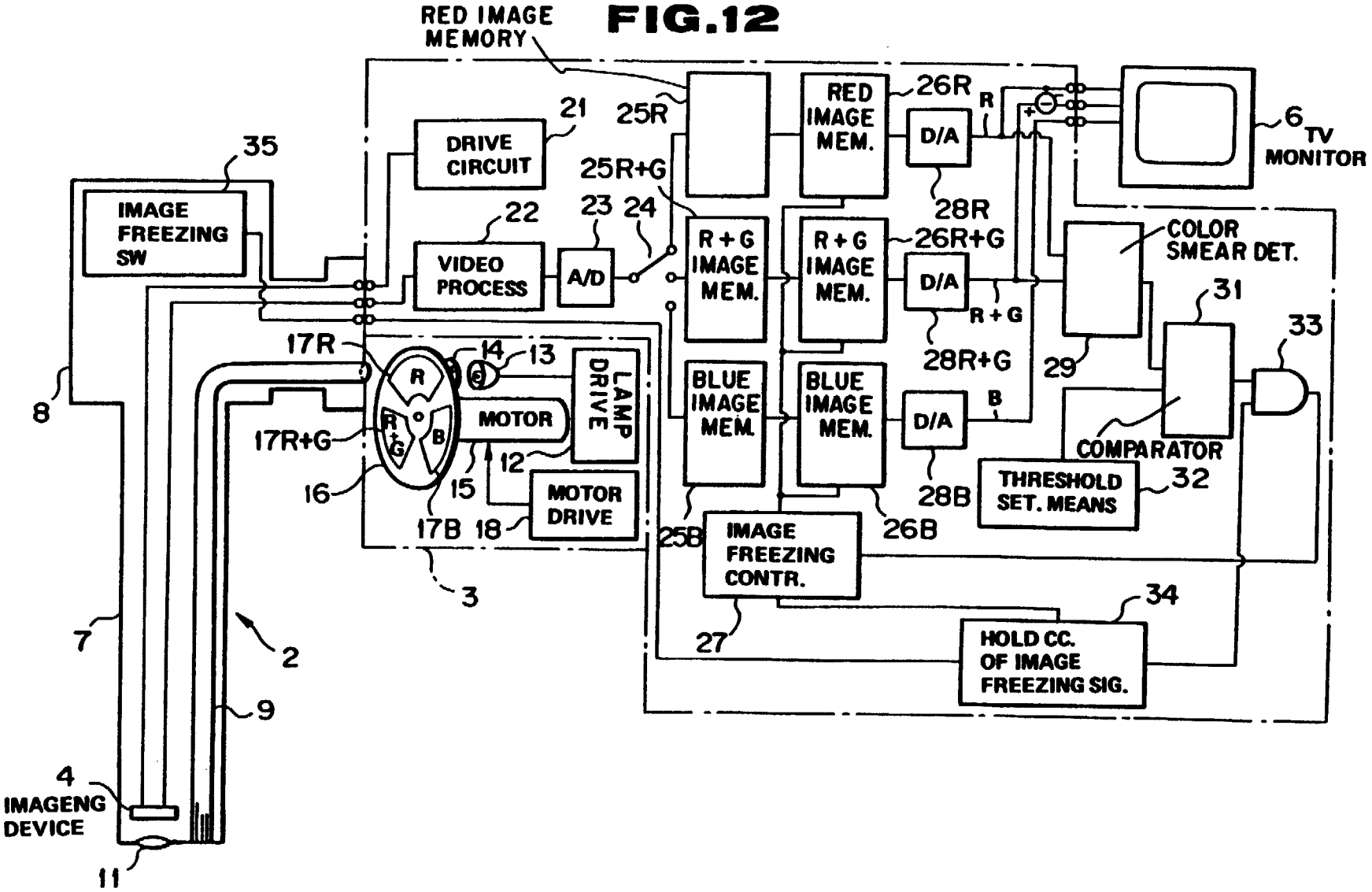
FIG. 12 is a block diagram showing the formation of another modification of the first embodiment.

In the modification shown in FIG. 12, as the color smear of a picture image having a common wavelength range or a red wavelength range in this case is sensed, the size of the color smear amount can be more positively evaluated from the size of the correlation amount between two picture images.

In FIGS. 1 to 11, the color smear amount between the picture image components imaged in different wavelength ranges at different times is sensed. In FIG. 12, the color smear amount between the picture image components having a partly common wavelength range is sensed.

Figure 13:
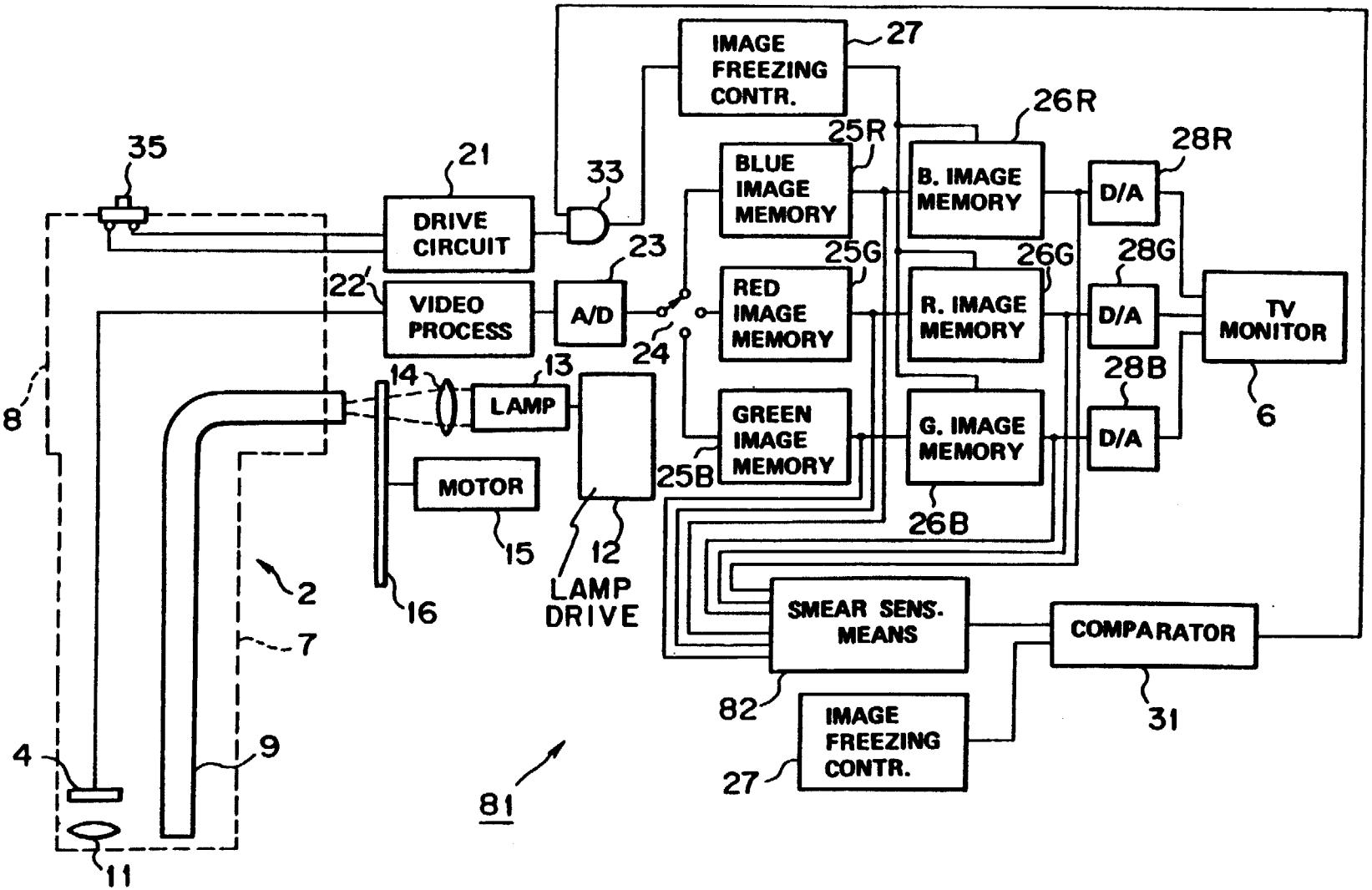
FIG. 13 is a block diagram showing the formation of a system of the second embodiment of the present invention.

Now, a system 81 of sensing the color smear amount between the picture image components imaged by the same wavelength components is shown in FIG. 13.

The color signals G and B of the D/A converters 28G and 28B are input into the color smear detecting means 29 in the system 1 shown in FIG. 1. However, in this system 81, the picture image data of the picture image memories 25R, 25G and 25B and the picture image data of the picture image memories 26R, 26G and 26B are input into the color smear detecting means 82. Between different fields or frames and with the picture image components of the same wavelength range, the respective color smear amounts or picture image smear amounts are sensed.

Figure 14:
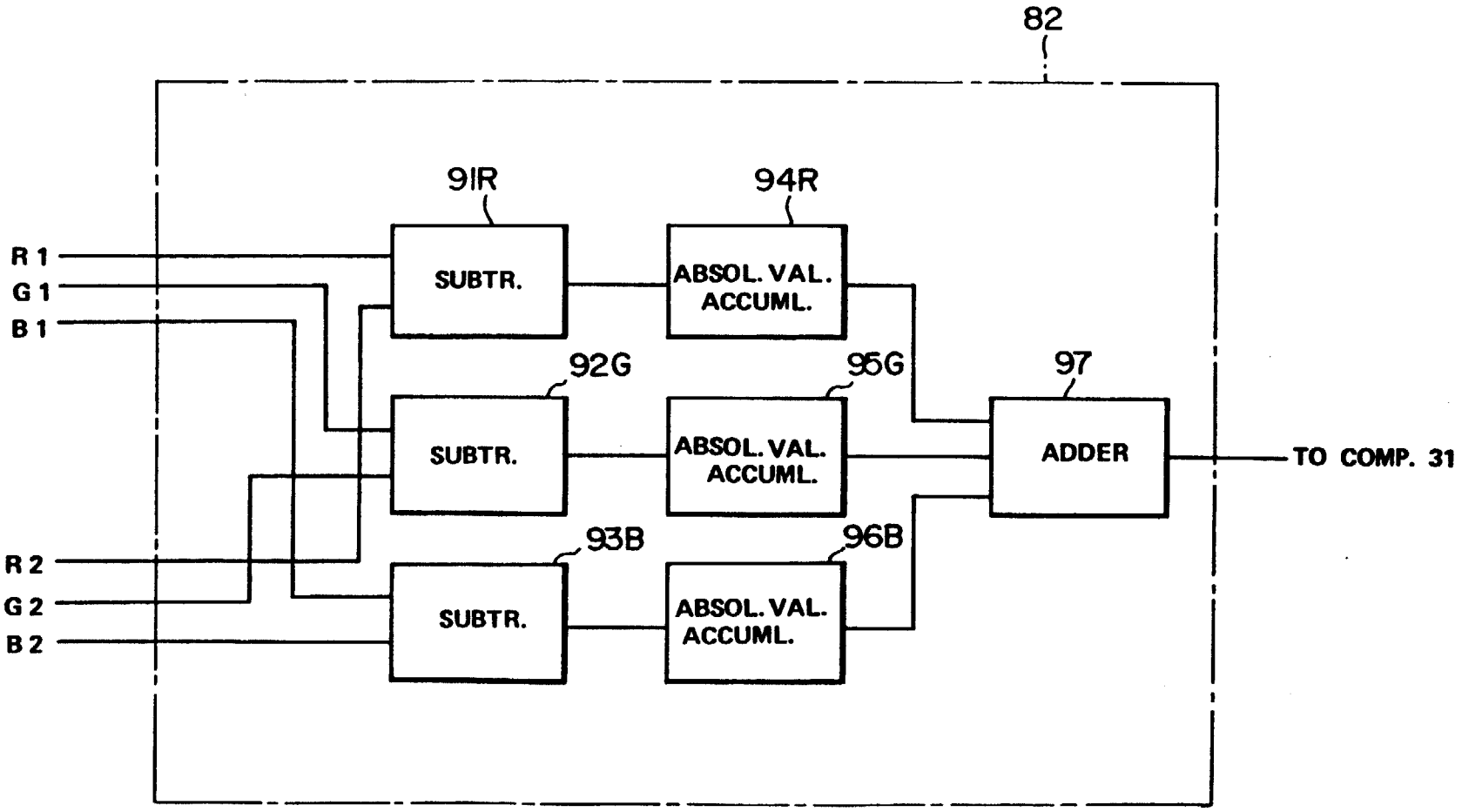
FIG. 14 is a block diagram showing the formation of smear sensing means to be used in the second embodiment.

The formation of this detecting means is shown in FIG. 14 in which 91R, 92G and 93B represent respectively a red subtractor, green subtractor and blue subtractor formed of ROM's or arithmetic logical operation IC's. The respective outputs (represented respectively by R1 and R2)of the picture image memories 25R and 26R are input into the subtractor 91R. The respective outputs G1 and G2 of the picture image memories 25G and 26G are input into the subtracter 92G. Further, the respective outputs B1 and B2 of the picture [Fuage] *gauge* memories 25B and 26B are input into the subtracter 93B. The respective outputs of the subtracters 91R, 92G and 93B are input respectively into absolute value accumulators 94R, 95R and 96B. These absolute value accumulators 94R, 95G and 96B are connected at the respective output ends to an adder 97. The others are of the same formation as is explained in FIG. 1 and are represented by the same reference numerals. (See the video processing circuit 22' in FIG. 8.)

The operation of the thus formed smear detecting means 82 shall be explained in the following. First of all, the difference between the outputs R1 and R2 of the picture image memories 25R and 26R is operated in the subtracter 91R and the absolute values of the results are accumulated over one field or one frame by the absolute value accumulator 94R. The red component picture image data recorded in the picture image memories 25R and 26R are smeared by one field or one frame in the time and therefore, if the relative speed between the object and the endoscope tip is large, the picture image smear between both will be large and the output of the subtracter 91R will be also large.

On the contrary, in case the relative speed between the object and the endoscope tip is small and they are substantially stationary, the output of the subtractor 91R will be substantially zero and the output of the absolute value accumulator 94R will be also substantially zero.

The green component picture image data and blue component picture image data are also processed in the same manner respectively by the subtracter 92G and absolute value accumulator 95 and by the subtracter 93 and absolute value accumulator 96B and the accumulated value of the absolute values of the differences of the picture image data between two fields or two frames is output. The accumulated value outputs from the respective absolute value accumulators 94R, 95G and 96B are added by the adder 97. Therefore, the output of this adder 97 corresponds to the size of the smear between the fields or frames of the respective color component picture images over one field or one frame. The larger the smear, the larger the output of the adder 97. On the contrary, the smaller the smear, the smaller the output of the adder 97. The output of this adder 97 is input into the comparator 31 and is compared with a preset value.

Figure 15:
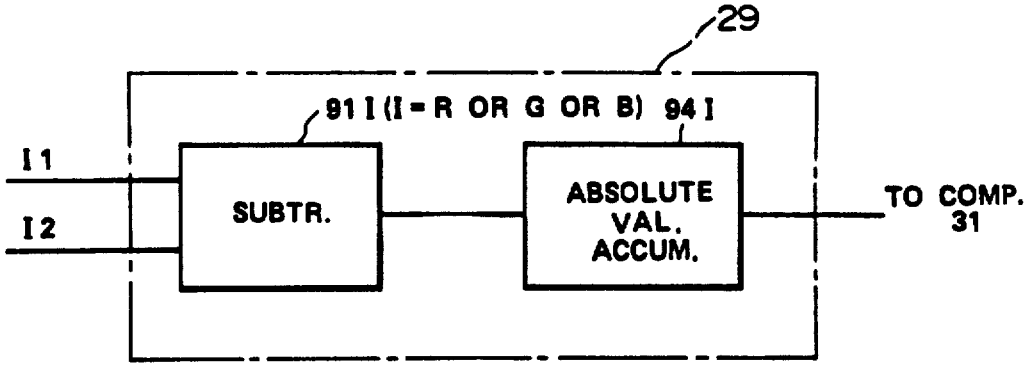
FIG. 15 is a block diagram showing another [formation] *schematic* example of a smear sensing means.

In this formation example, in order to detect the smear amount, all of the respective color components of red, green and blue are shown to be used. However, the invention is not limited to this. Only the components of any one color may be used. In such case, as shown in FIG. 15, the system can be formed of subtracters 91I and absolute value accumulators 94I. By the way, here 1 is shown to represent any of Color signals R, G and B of red, green and blue. Thus the [hardwear] *hardware* can be simplified, the entire system or apparatus can be made small and the cost can be reduced.

FIG. 15 shows the case of components of one color. However, the smear amount of a picture image of components of two colors can be sensed in the formation. In this case, too, there is an advantage that the formation can be made simpler than in the case of three colors.

In the above mentioned second embodiment is shown a formation wherein the smear amount is detected by using the same color component picture image of continuous two fields or two frames. However, the invention is not limited to this. The smear amount may be detected by using the same component picture image of two fields or two frames separated in the time by more than two fields or two frames.

In the above mentioned second embodiment is explained an application to the electronic scope 2 wherein the imaging device 4 is arranged in the tip part of the insertable part 7. However, it is apparent that, as shown in FIG. 8, the invention can be applied likewise to the fiber scope 60 and this fiber scope 60 as fitted in the eyepiece part 64 with the television camera 63 instead of the electronic scope 2.

By the way, in FIG. [11] *12*, the color smear is sensed in the red and green component picture image and green component picture image. However, it is apparent that any other combination will do.

Figure 16:
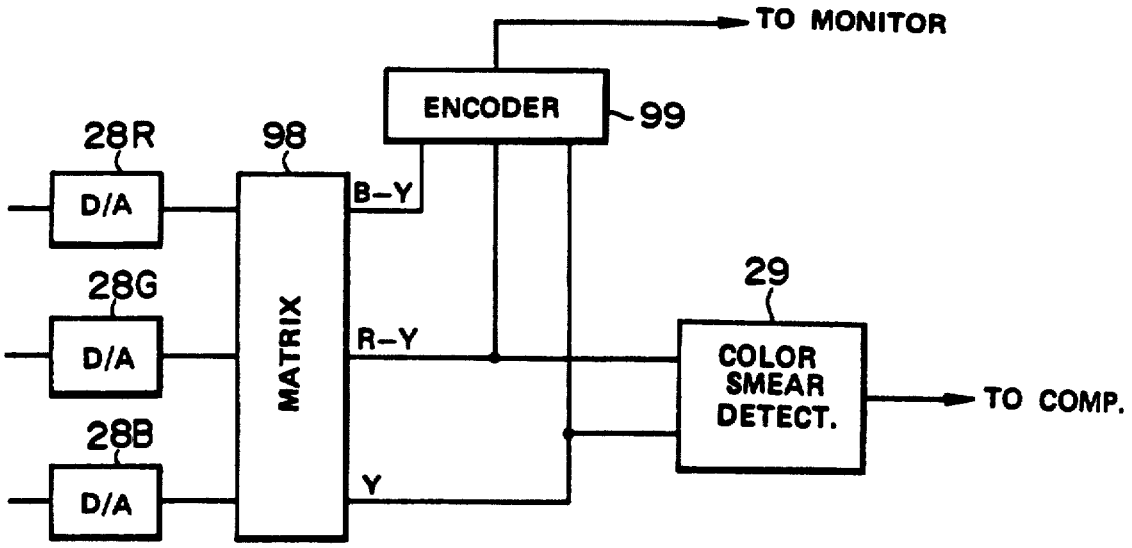
FIG. 16 is a block diagram showing the formation of a part of a modification different from FIG. 12.

As shown in FIG. 16, for example, in the embodiment in FIG. 1, a matrix circuit 98 is provided on the output side of the D/A converters 28R, 28G and 28B and, for example, a luminance signal Y and color difference signal R-Y (or B-Y) may be input into the color smear detecting means 29 to detect a color smear amount. Two color difference signals R-Y and B-Y may be input into the color smear detecting means 29 to detect the color smear amount.

Not only the color signals R, G and B but also, as shown in FIG. 16, a composite video signal produced in an encoder 99 may be input into the monitor 6.

According to the above mentioned first or second embodiment, in case the smear amount of picture image components between fields or frames imaged at different times with different color components or the same color components is sensed and is below an allowable value, the picture image freezing controlling means will be operated to obtain a frozen picture and therefore, if only the operation of freezing the picture image is made by the operator, a frozen picture having little color smear or picture image smear will be able to be obtained.

Therefore, it is not necessary to make a complicated operation of repeating the freezing instruction and freezing release in order to obtain a frozen picture having no color smear, the inspection time is reduced accordingly, the pain of the examinee can be alleviated and the affected part can be effectively prevented from being overlooked by the color smear or the like. A color smear preventing apparatus which is simpler in the formation, smaller and cheaper than a system using a color smear correcting means can be provided.

Figure 17:
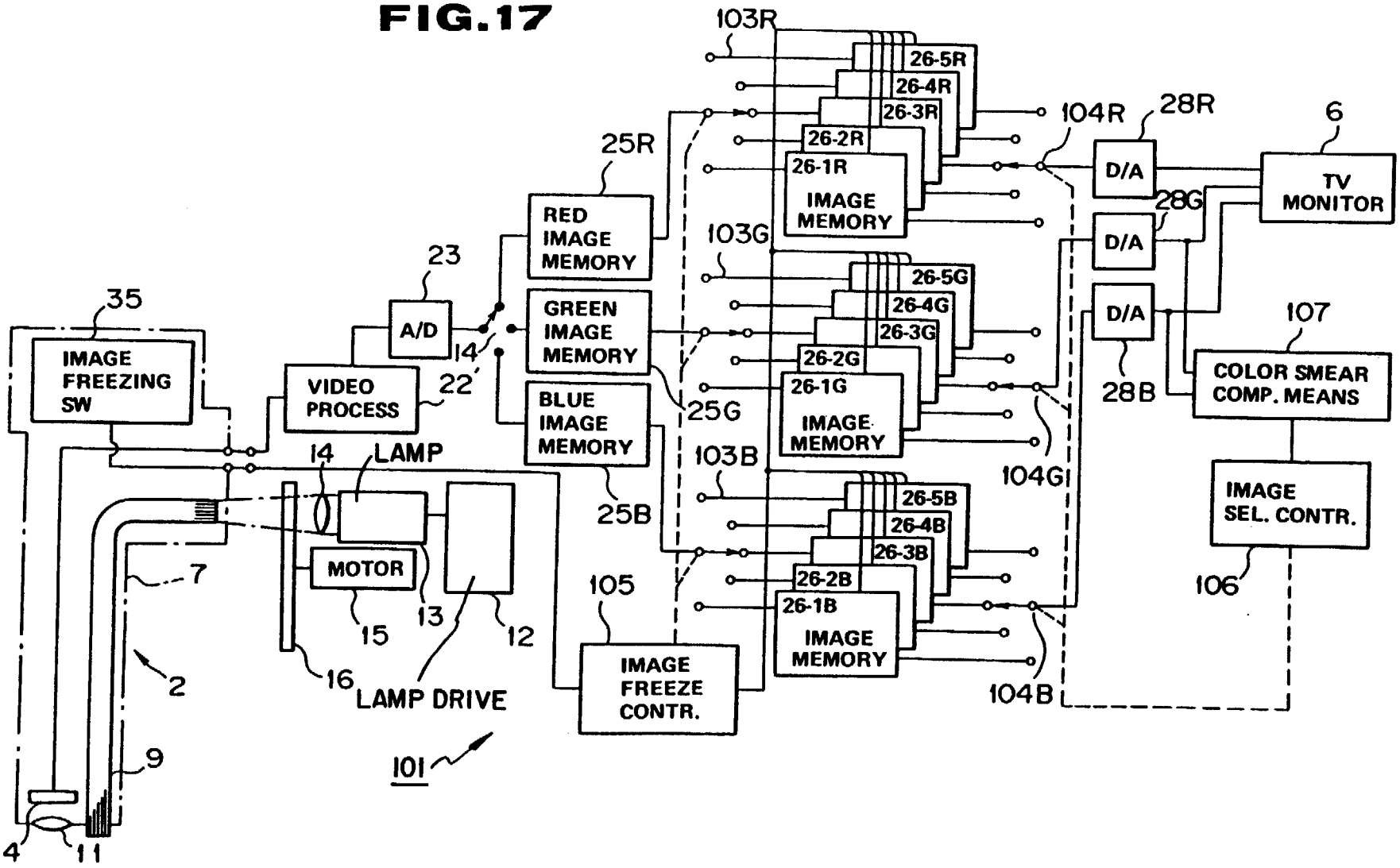
FIG. 17 is a block diagram showing the formation of a system of the third embodiment of the present invention.

The third embodiment of the present invention shall be explained in the following with reference to FIG. 17.

The system 101 of this third embodiment is the system 1 in FIG. 1 wherein the picture image memories 26R, 26G and 26B are replaced with a plurality of picture image memories 26-1R, 26-2R, . . . , 26-5R; . . . , 26-1G, 26-2G, . . . , 26-5G; 26-1B, 26-2B, . . . , 26-5B represented respectively by {26-iR}, {26-iG} and {26-iB} and input picture image switching switches 103R, 103G and 103B and output picture image switching switches 104R, 104G and 104B are provided respectively at the input ends and output ends of the plurality of picture image memories {26-iR}, {26-iB} and {226-iB}.

The input picture image switching switches 103R, 103G and 103B are sequentially switched by a picture image freezing controlling circuit 105. The output picture image switching switches 104R, 104G and 104B are controlled in switching by a selection controlling signal by a picture image selection controlling circuit 106. This picture image selection controlling circuit 106 is controllable by a color smear comparing means 107 into which the output signals, for example, of the D/A converters 28G and 28B are input.

In the above mentioned color smear comparing means 107, an A/D converter 112 is provided at the output end of the integrater 47 in the color smear sensing circuit 29 shown in FIG. 2, the output of this A/D converter 112 is input into a register 113 formed of a semiconductor memory or the like, the data input into this register 113 are then compared with the data input into a comparator 114 through the A/D converter 112 and the compared result is input into a timing controlling circuit 115 which controls the register 113 to hold the data value corresponding to the minimum smear amount before then on the basis of the compared result by the comparator 114. The minimum color smear picture image number on the entire picture image is output to the picture image selection controlling circuit 106.

The [others] *other components of this embodiment* are of the same formation as of the above described embodiment.

The operation of this third embodiment shall be explained in the following:

The white color light radiated from the lamp 13 passes through the color filter disc 16 rotated and driven by the motor 15 so as to be color sequential lights of R, G and B which enter one end surface of the light guide 9 of the electronic endoscope 2. The color sequential lights having entered the end surface of the light guide 9 are transmitted through the light guide 9, reach the tip of the electronic endoscope 2 and are emitted from the other end surface of the light guide 9. The emitted color sequential lights illuminate such object to be imaged as a stomach wall and the image of the object is formed on the imaging device 4 by the objective lens 11 The imaging device 4 is driven by the video processing circuit 22' and its output is made a video signal by the video processing circuit 22'.

The output of the video processing circuit 22' is digitalized by the A/D converter 23 and the digital picture image data are input and recorded respectively into the picture image memories 25R, 25G and 25B while being switched for the respective R, G and B component Picture image data by the switching switch 24. By the way, the switching switch 24 is operated to make the sequential switching in response to the light colors of the color sequential lights as synchronized with the rotation of the color filter disc 16.

Then, the respective picture image data recorded in the picture image memories 25R, 225G and 25B are transferred at a high speed to the picture image memories 26-1R, 26-1G and 26-1B through the input picture image switching switches 103R, 103G and 103B. This transferring operation is made by utilizing the synchronized signal period of the television. The picture image data transferred to the picture image memories 21-1R, 21-1G and 21-1B are read out as synchronized with the synchronized signal of the television, are converted to analogue signals by the D/A converters 28R, 28G and 28B through the picture image memory output switches 104R, 104G and 104B and are displayed in the TV monitor 6. Usually, as the above mentioned transfer is made for each frame, moving picture images are observed in the TV monitor 6.

In the case of freezing and observing a picture image, the operator pushes the picture image freezing switch 35 to instruct the freezing. When this picture image freezing switch is operated to be pressed, a picture image freezing instructing signal will be transmitted to the picture image freezing controlling circuit 105.

In the picture image freezing controlling circuit 105, the picture image memory input switches 103R, 103G and 103B are switched respectively to predetermined frames or fields and respective R, G and B component picture image data are sequentially recorded at different timings into the remaining (four in this embodiment) picture image memories 26-2G, 26-5G and 26-2B, . . . ,26-5B. When the recording in all the picture image memories ends, by the picture image selection controlling circuit 106, the picture image data at the respective timings are sequentially selected and read out of the above mentioned picture image picture image memories {26-iR}, {26-iG} and {26-iB} and are delivered to the color smear comparing means 107.

In the color smear comparing means 107, which timing at which the R, G and B picture images among the five picture image groups are recorded is least in the color smear is sensed and the sensed result is output to the picture image selection controlling circuit 106 by which the picture image memory output switches 104R, 104G and 104B are switched and controlled on the basis of the sensing signal from the above mentioned color smear comparing means 107 so that the picture image of the least color smear may be displayed. As a result, the frozen picture image of the least color smear is displayed on the TV monitor 6.

The frozen picture displayed in this case is the least in the color smear among the five picture images and is easy to see.

The operation of the color smear comparing means 107 shall be explained in the following:

The operation that the G and B picture image signals of one field or one frame are integrated by the integrator 47 through the subtracter 40 or the like is the same as in FIG. 2. The output of this integrator 47 shows the color smear amount. In order to detect the picture image in which the output of the integrator 47 showing this color smear amount is minimum, the output of the integrator 47 is digitalized by the A/D converter 112 and is input into a comparator 114 so as to be compared with the contents of a register 113 in which the compared result just before is memorized. By the way, in the case of comparing the first picture image, the register 113 may be reset to be cleared to 0. Thus, the color smear amounts of the five picture images are sequentially compared and finally the value of the integrator 47 in the case of the picture image of the least color smear is digitalized and recorded in the register 113. By a timing controlling circuit 115, the picture image memory number corresponding to the picture image of the least color smear amount on the basis of the contents of the register 113 is output to the picture image selection controlling circuit 106 by which the switching switches 104R, 104G and 104B are controlled so as to select the picture image memories 26-jR, 26-jG and 26-jB of the picture image memory number j.

In the above mentioned embodiment, after the picture image freezing switch 35 is pushed, a plurality of picture images are recorded sequentially in the picture image memory group. However, the invention is not limited to this. A plurality of picture images may be always recorded sequentially or cyclically in the picture image memory group and, in case the picture image freezing switch 35 is operated, the picture image of the least color .smear amount may be selected from among a Plurality of picture images [until just before] *recorded just before the freezing switch 35 was pushed.* As it takes some time for the operator to operate to freeze a Picture image, the freezing timing will be delayed. The above mentioned method can eliminate this delay and is therefore useful.

Figure 18:
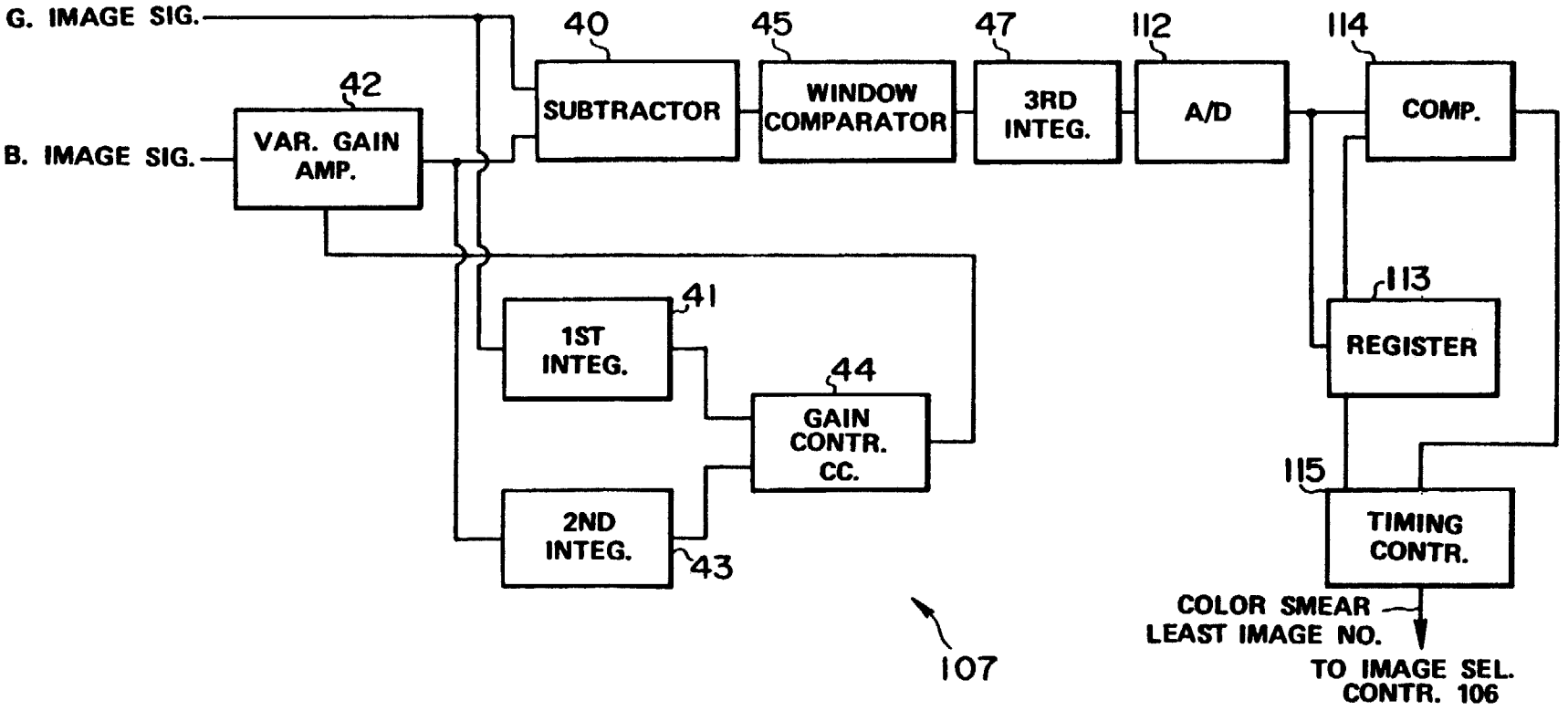
FIG. 18 is a block diagram showing the formation of a color smear comparing means in the third embodiment.

Also, in the color smear comparing means shown in FIG. 18, the entire picture surface is integrated by the integrators 41, 43 and 47 but, in an ordinary electronic endoscope, the endoscope picture image part is [a part] *a portion of the entire image.* Therefore, as described above, the integration may be controlled to be made in the endoscope picture image part only. Also, the color smear may be sensed only in a part of the endoscope picture image.

In order that the invention may be applied to other embodiments, for example, the color smear may be sensed by utilizing a two-color color component picture image having had the outline enhanced or extracted by making a differentiation or the like.

The video signal obtained generally from an electronic endoscope apparatus is gamma-corrected. The color smear may be detected for the signal made linear through a circuit having a reverse gamma characteristic before being input into the color smear comparing means.

According to this embodiment, it is possible to obtain a frozen picture having the least color smears among the picture images memorized in a plurality of picture image memories.

Now, in the above described respective embodiments, there is formed a means wherein the size of the correlated amount between the picture images imaged at different times, that is, the correlated amount in the time is determined and the movement amount of the object is detected from the size. However, the present invention is not limited to this. A system or apparatus using any of the following movement amount sensing means will do.

Figure 19:
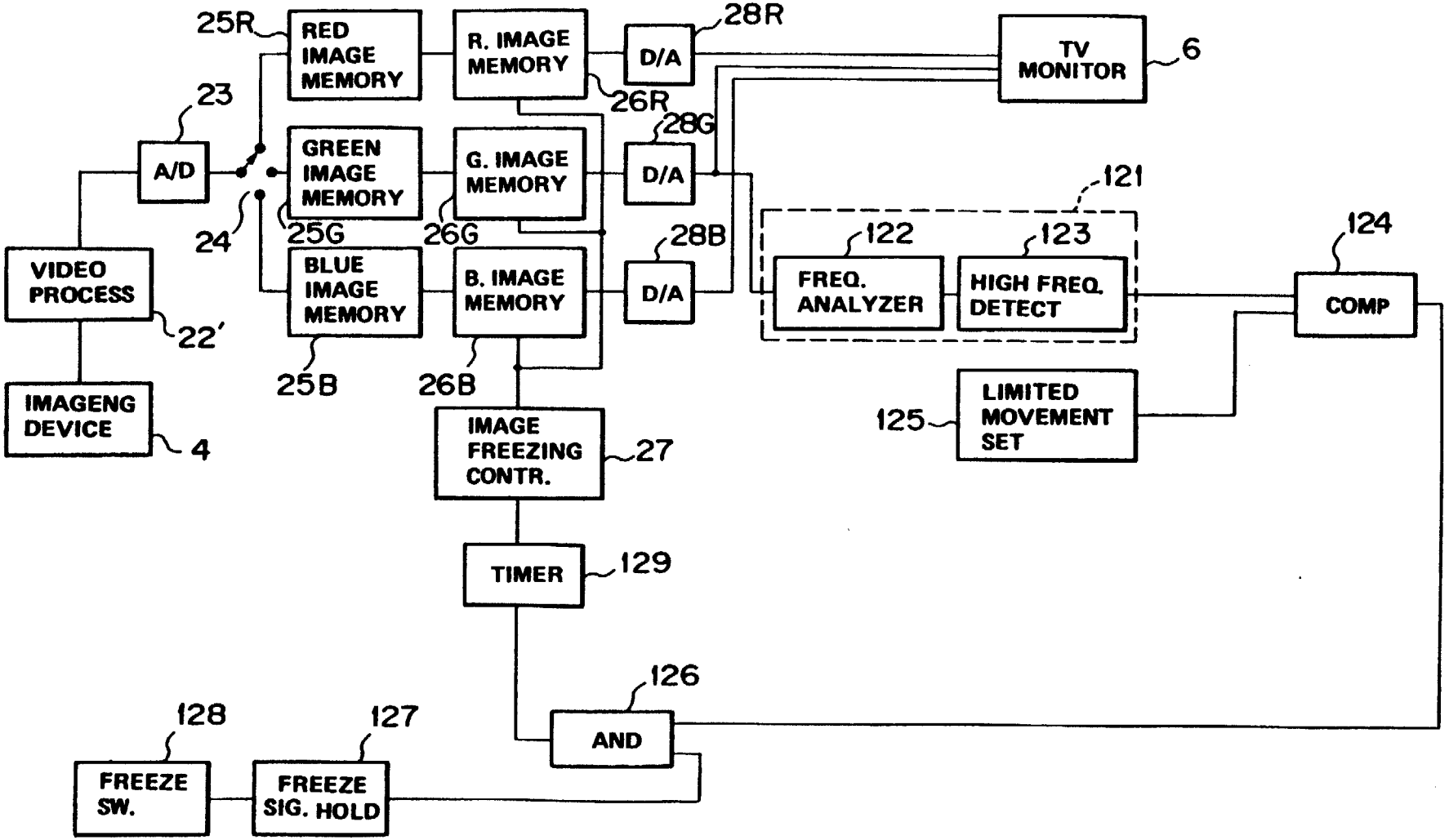
FIG. 19 is a block diagram showing the formation of an essential part of a system of the fourth embodiment of the present invention.

FIG. 19 shows an essential part of a system in which a movement amount sensing means 121 by sensing the high frequency part of a frequency is applied to the first embodiment.

For example, the output of the D/A converter 28G is input into a frequency analyzer 122 by which the frequency for the green picture image signal is analyzed and its output signal is input into a high frequency sensing circuit 123. The size of the high frequency component is sensed by this circuit 123, is input into a comparator 124 and is compared with the limit movement amount from a limit movement amount setter 125. When the size of the high frequency component amount output from the high frequency sensing circuit 123 becomes above the limit movement amount, the comparator 124 will output a true value to an AND circuit 126 in which the gate opening and closing can be controlled by a freezing signal holding circuit 127 and the freezing signal is input for a fixed time by the operation of the picture image freezing switch, that is, the freezing switch 128. When the true value is output from the comparator 124 during this freezing signal period, a signal holding the frozen picture for a fixed time will be input into a freezing signal holding circuit 127 by a timer circuit 129.

The [others] *other components of this embodiment* are of the same formation as of the above described embodiment.

Figure 20:
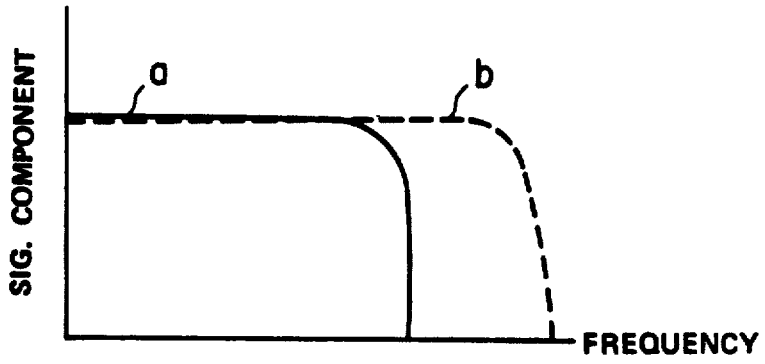
FIG. 20 is a view for explaining the operation of the fourth embodiment.

In this system, when the object is moving, as shown in a in FIG. 20, the high frequency components of the video signal will decrease. Therefore, for example, when the frequency components of the color signal G of the signal are analyzed and the high frequency components on the entire picture surface are found to be below a certain level, that is, the limit movement amount, the object will be judged to be moving. Therefore, even if the freezing switch 128 is operated, the picture image freezing operation will not be made.

On the other hand, in case the movement of the object stops or is small, as shown in b in FIG. 20, the high frequency components will increase and therefore, in case the limit movement amount is exceeded, the picture image freezing operation will be made by the output of the comparator 124.

Figure 21:
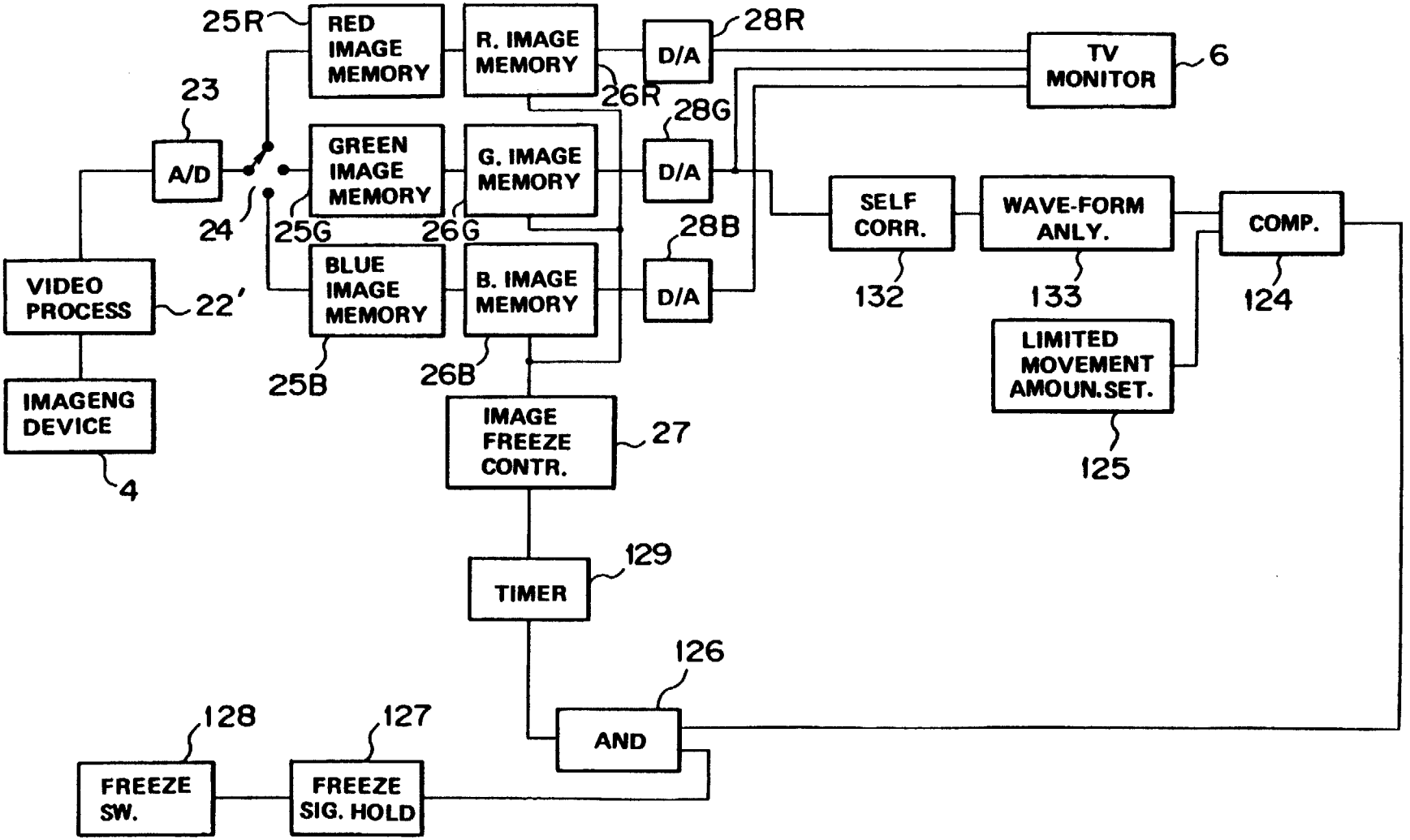
FIG. 21 is a block diagram showing the formation of an essential part of a modification of the fourth embodiment.

FIG. 21 shows a system wherein the movement amount is detected by a self-correlation.

As shown in FIG. 21, the output signal of the D/A converter 28G is input into a self-correlation circuit 132 detecting the self-correlation amount. The output of this circuit 132 is input into a waveform analyzer 133 and the feature of the waveform is extracted. The output of this waveform analyzer 133 is input into the comparator 124 and is compared with the limit movement amount from the limit movement amount setter 125. The [others] *other components* are of the same formation as in FIG. 19.

Figure 22A:
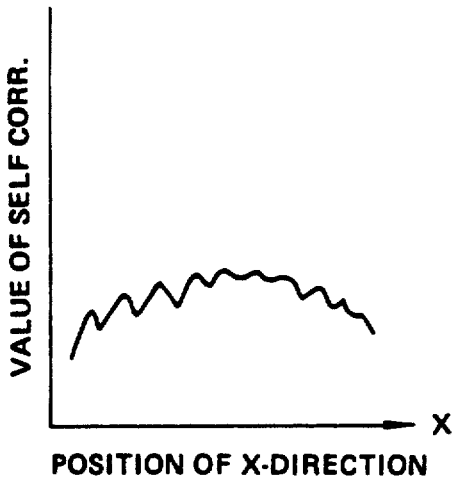
FIGS. 22 and 22b are views for explaining the operation of the modification shown in FIG. 21.
Figure 22B:
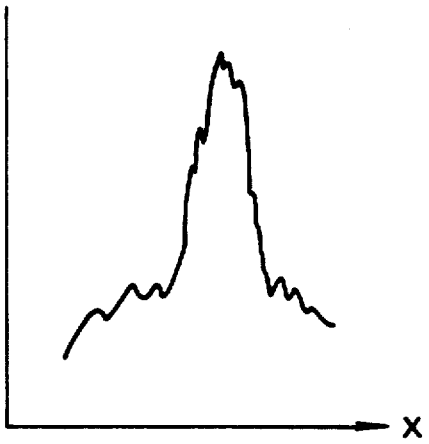

In this modification, as shown in FIGS. 22a and 22b, the self-correlation functions of the picture images will be different between the case that the object is moving and the case that it is stopped.

Therefore, when the self-correlation amount is detected by the self-correlation circuit 132, the waveform is analyzed by the waveform analyzer 133, for example, a waveform part having a peak is extracted and the extracted part is compared with the [limit] *limited* movement [part] *amount* by the comparator 124, *and* a control signal as to whether the picture image is to be frozen or not will be produced.

Figure 23:
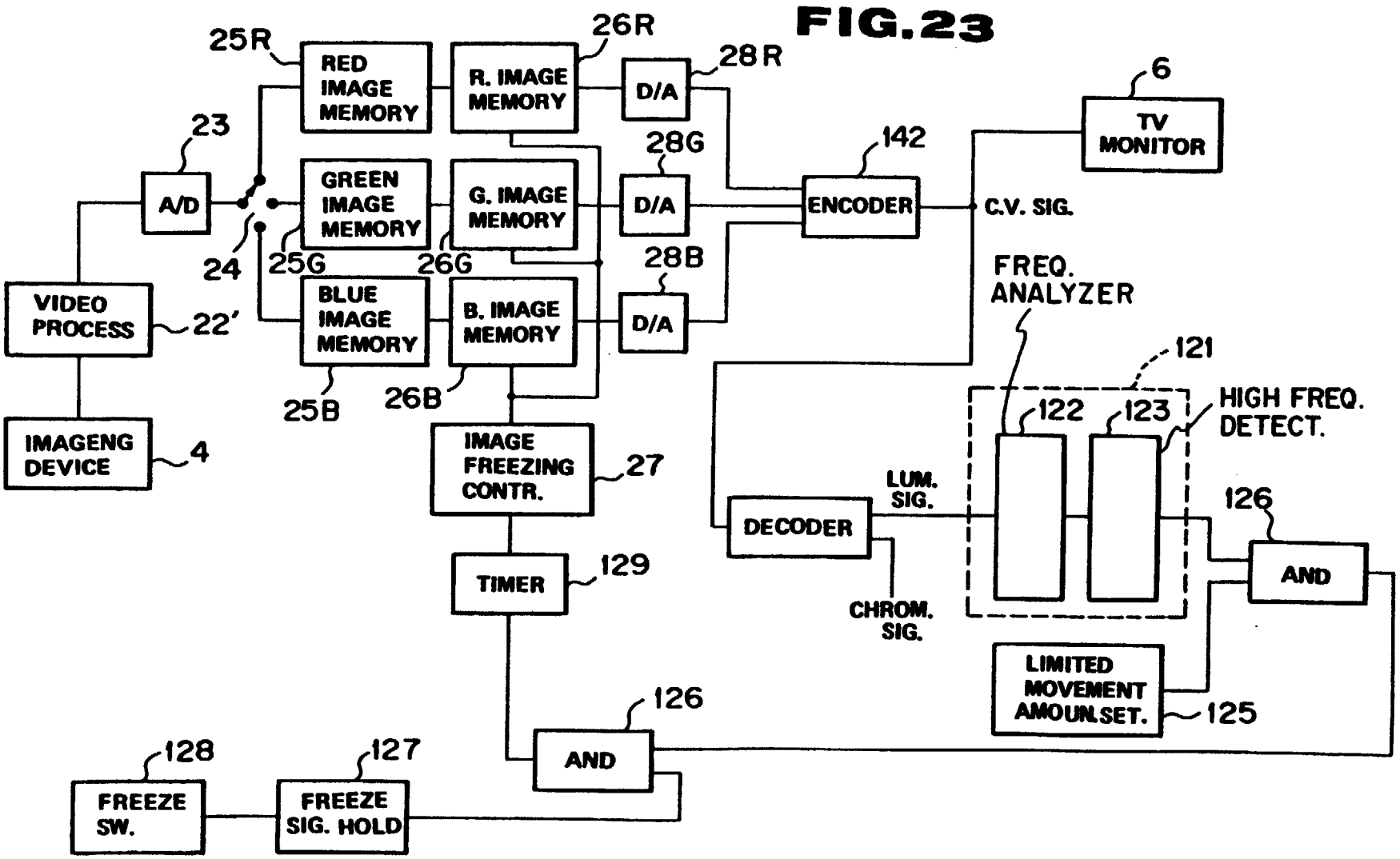
FIG. 23 is a block diagram showing an essential part of another modification of the fourth embodiment.

FIG. 23 shows another modification of the fourth embodiment. For example, in FIG. 19, the movement amount sensing the high frequency part is sensed for the color signal G. The same is sensed with a luminance signal.

That is to say, the output signals of the D/A converters 28R, 28G and 28B are input into an encoder 142. A composite video signal is produced in this encoder 142, is displayed in the TV monitor 6 and is input into a decoder 143.

A luminance signal Y and color difference signals are produced in this decoder 143. This luminance signal Y is input into the movement amount sensing means 121. The [others] *other components* are of the same formation as of the system shown in FIG. 19.

Figure 24A:
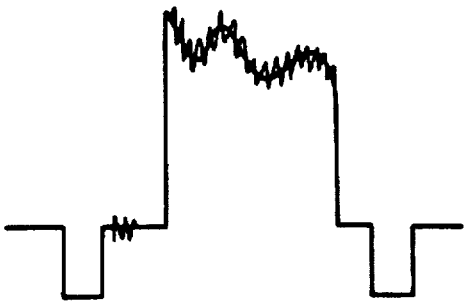
FIG. 24a and 24b are views for explaining the operation in FIG. 23.
Figure 24B:
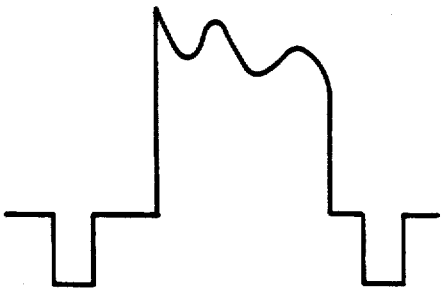

In this system, the luminance signal components shown in FIG. 24b are extracted from the composite video signal shown in FIG. 24a and the movement amount is detected for this luminance signal Y.

Figure 25:
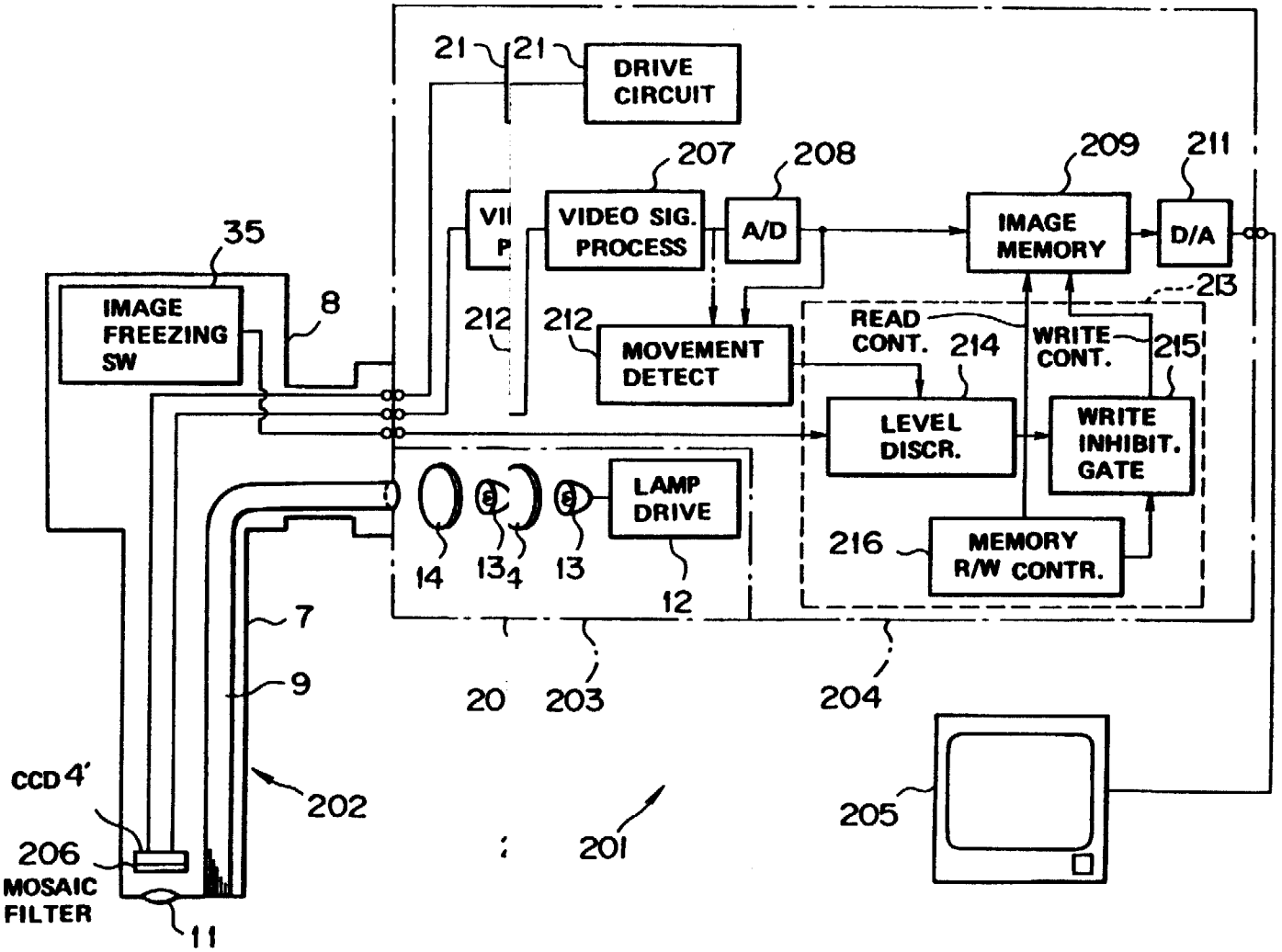
FIGS. 25 to 28 relate to the fifth embodiment of the present invention.

The frame sequential type system wherein color imaging signals are obtained by respectively imaging under illuminating lights different in the wavelength has been explained in the above described respective embodiments. Now, a simultaneous type system wherein color imaging is made under a white color light shall be explained in the following:

FIG. 25 shows a system of the fifth embodiment of the present invention. This system 201 comprises a simultaneous type electronic scope 202, a light source unit 203 feeding an illuminating light to this scope 202, a video processor 204 processing a signal for the scope 202 and a color monitor 205.

The above mentioned electronic scope 202 is the electronic scope 2 shown in FIG. 1 and provided with a color filter fitted with a color separating color mosaic filter 206 in front of the imaging surface of the imaging device 4 (CCD 4' in FIG. 25).

The light source unit 203 is the light source unit 3 shown in FIG. 1, having no motor 15 and rotary filter 16 in the motor driving circuit 18 and outputting a white color light.

The signal read out of the CCD 4' by the driving signal output from the driving circuit 21 is input into the signal processing circuit 207 and a reference video signal, for example, a composite video signal is produced. This signal is converted to a digital signal by an A/D converter 208 and is input into a picture image memory 209.

When the picture image data written into this picture image memory 209 are read out, they will be returned to an analogue signal by a D/A converter 211 and will be color displayed by a color monitor 205.

The output signal of the above mentioned A/D converter is input into a movement detecting circuit 212, the movement amount is detected, the output signal is input into a level discriminating circuit 214 within a WRITE/READ controlling circuit 213 and is compared with a threshold value. In case the output of this level discriminating circuit 213 is input into a writing-in inhibiting gate circuit 215 and is judged to be of a true value, the writing signal output to this writing prohibiting gate circuit from a memory R/W controlling circuit 216 will be inhibited from being output to the picture image memory 209 and an operation of memorizing a frozen picture will be made. By the way, the memory R/W controlling circuit 216 outputs to the picture image memory 209 a WRITE signal memorizing picture image data and a READ signal reading out the memorized picture image data. In this case, the READ signal will be able to be always output to the picture image memory 209.

Figure 26:
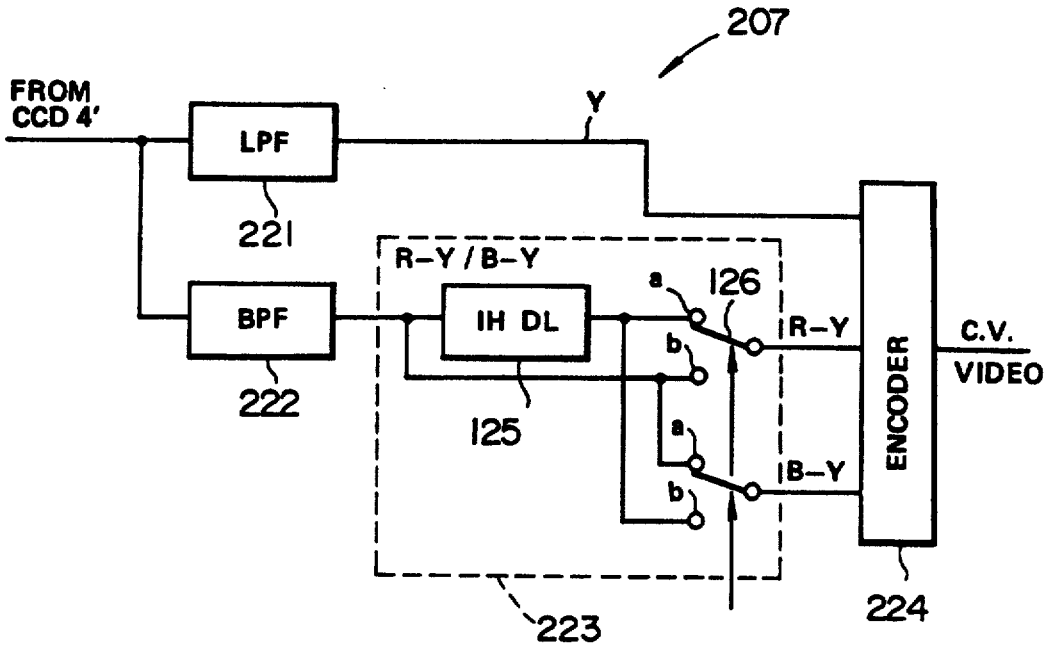

Now, the formation of the above mentioned video signal processing circuit 207 is shown in FIG. 26.

The output signal from the CCD 4' is input into an LPF 221 and BPF 222 and a frequency signal Y and line sequential color difference signal R-Y/B-Y are respectively produced. This line sequential color difference signal R-Y/B-Y is synchronized by a synchronizing circuit 223. These synchronized color difference signals R-Y and B-Y are input into an encoder 224 together with a luminance signal Y and are converted to a composite video signal 1 to be output.

The above mentioned synchronizing circuit 223 comprises a delaying circuit 125 delaying by 1H (one horizontal period) and operatively connected switches 126 and 127 in which contacts a and b are alternately switched by a switching signal $f_H/2$ having 2H as a period.

Figure 27:
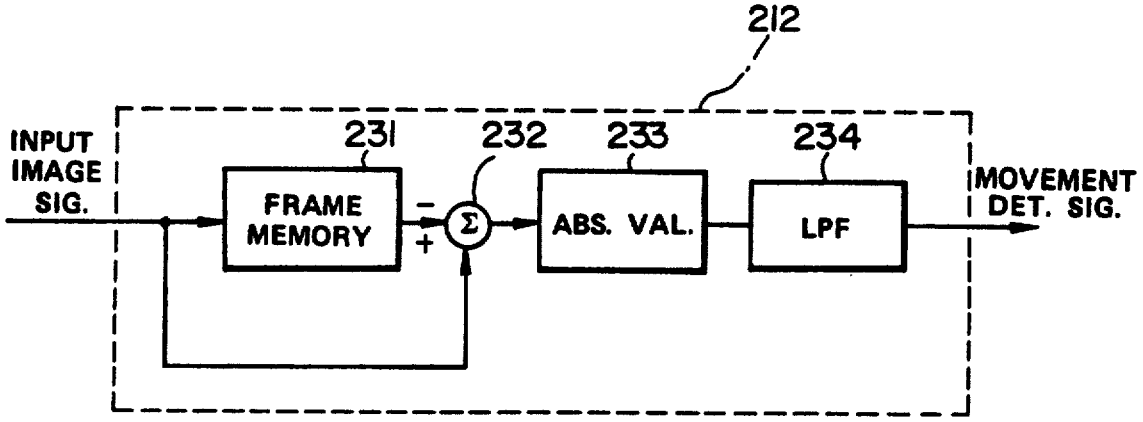

An example of the above mentioned movement detecting circuit 212 is shown in FIG. 27.

In this example, the input picture image signal is led by the + (added) input of a frame memory 231 and subtracting circuit 232. The picture image signal before 1 frame period read out of the above mentioned frame memory 231 is led to the − (subtracted) input of the above mentioned subtracting circuit 232 and is subtracted from the input picture image signal led to the added input. The output signal of this subtracting circuit 232 is made an absolute value by an absolute value circuit 233 and is output as a movement detected amount through a low pass filter (LPF) 234. In this example, the larger the movement of the object, the larger the movement detected amount. By the way, the above mentioned frame memory 231 is used to detect the movement by comparing the picture image by 1 frame unit but may be formed by using instead a field memory or line memory.

Figure 28:
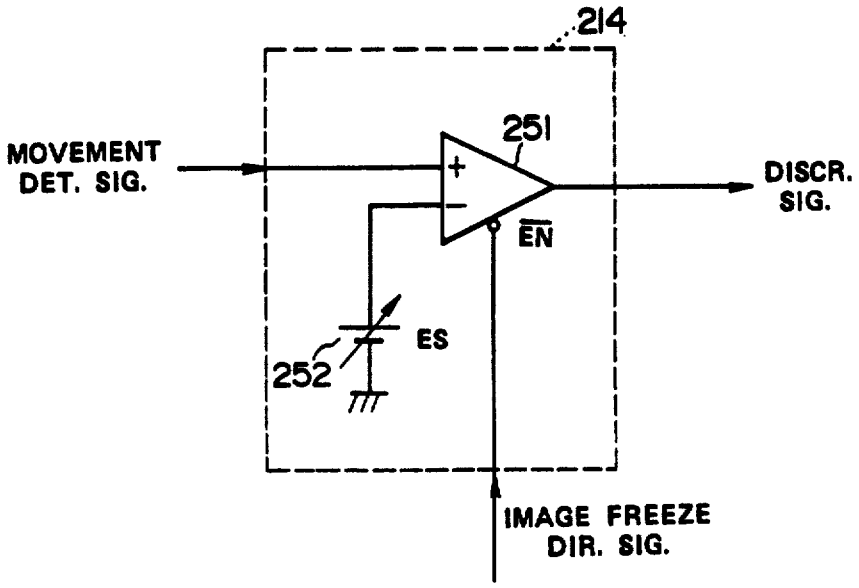

Also, an example of the above mentioned level discriminating circuit 214 is shown in FIG. 28.

The lever] *level* discriminating circuit 214 can be formed by using a comparator 251 fitted with an enabling terminal EN. In this example, the movement detected amount from the above mentioned movement detecting circuit 212 is applied to the (non-inverted) input end of a comparator 251, the reference value Es preset by a reference value (threshold value) setting means 252 is applied to the inverted input end and the picture image freezing directing signal from a freezing directing switch 35 is applied to the enabling terminal EN of the comparator 251. In this example, only when the picture image freezing directing signal is issued, the above mentioned movement detected amount and reference value Es will be compared with each other and whether there is a movement of the object will be judged by the size and will be output in the later step. In case the movement detecting circuit 212 is formed as shown in FIG. 27, when the movement detected amount is below the reference value Es, a control signal will be generated so as to operate a writing-in inhibiting gate in the later step to freeze the picture image. Here, the comparator 251 may compare the digital data as they are and the reference value setting means 252 setting the reference value Es may be of a digital type.

If the operation of the writing-in inhibiting gate 215 is controlled as synchronized with a frame signal showing the section of the input picture image, freezing by one picture surface unit will be possible.

Thus, according to this embodiment, as the movement of the object is detected by the movement detecting means 212 and, when the object moves little, the writing into the picture image memory 209 will be prohibited to freeze the picture image, a frozen picture in which the picture image is [little] deteriorated *only slightly* by the movement of the object can be memorized with a simple formation.

In the system shown in FIG. 25, the movement amount detecting circuit 212 is [of] the digital system shown in FIG. 27 but [those] *the systems* shown in FIGS. 19, 21 and 23 may be used. In such case, as shown by the two-point chain line in FIG. 25, the system will be of an analogue type in which the output signal of the video processing circuit 207 is input into the movement detecting circuit 212.

Figure 29:
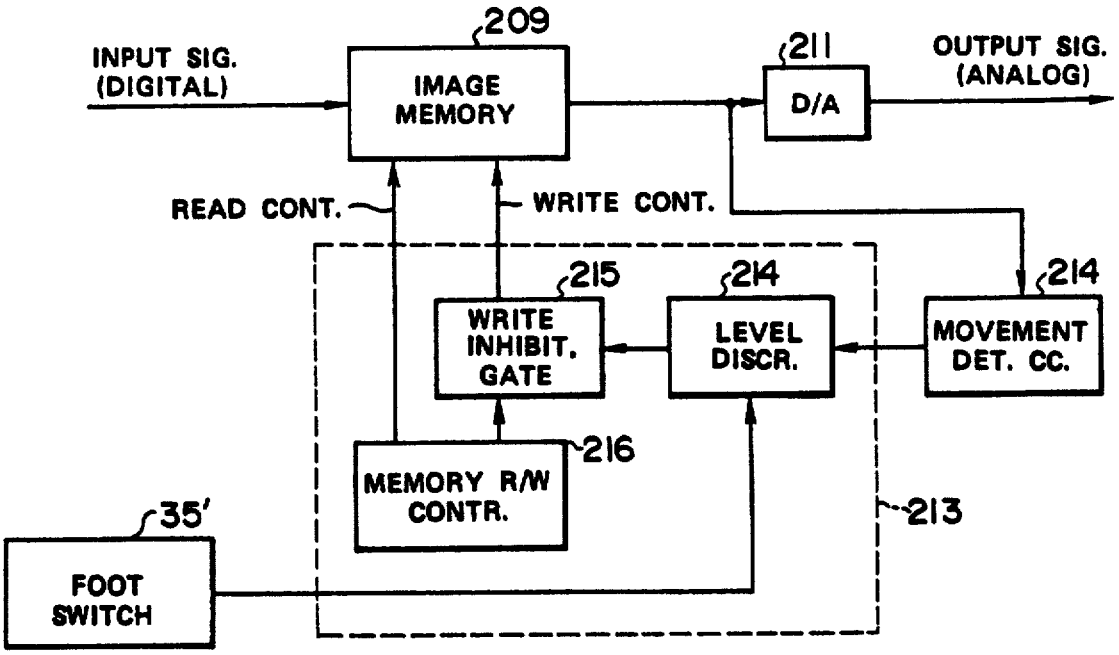
FIG. 29 is a block diagram showing the formation of an essential part of a modification of the fifth embodiment.

FIG. 29 shows an essential part of a modification of the fifth embodiment. That is to say, in FIG. 25, the output signal of the picture image memory 209 is input into the movement detecting circuit 212. By the way, in this modification, the freezing switch is formed of a foot switch 35'.

The operation and effect are the same as of the fifth embodiment.

Figure 30:
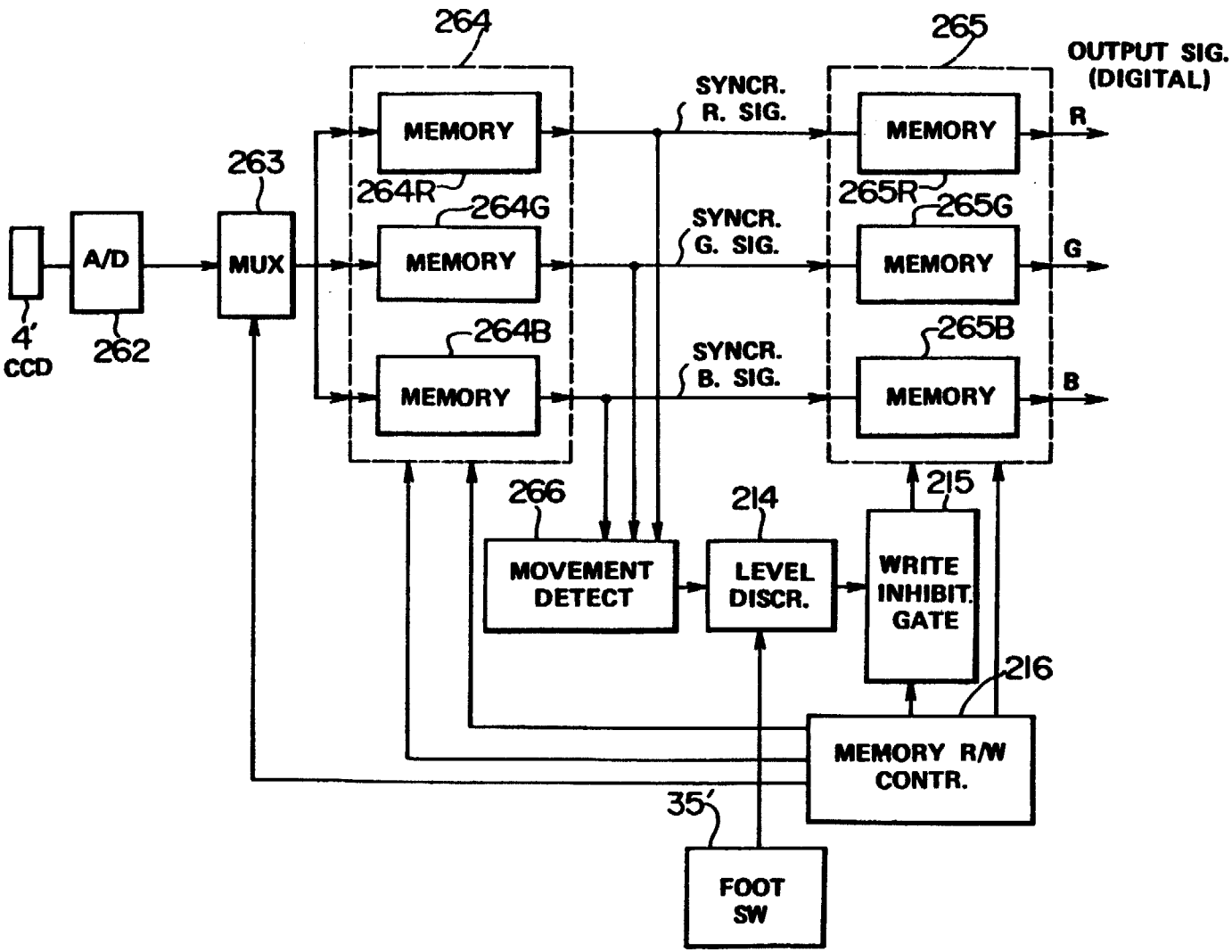
FIG. 30 is a block diagram showing an essential part of the sixth embodiment of the present invention.

FIG. 30 shows an essential part of the system of the sixth embodiment of the present invention.

This system is of a frame sequential type in the case of using the CCD 4' having no color filter. The illuminating means not illustrated is assumed to be, for example, the light source unit 3 shown in FIG. 1.

The output signal of the CCD 4' is converted to a digital signal by an A/D converter 262, is switched by a multiplexer (MUX) 263 and is written into synchronizing memories 264R, 264G and 264B (represented by the reference numeral 264) corresponding to the respective colors. At the time of reading out of the above mentioned synchronizing memories 264, the respective primary color picture images will be simultaneously read out and will be sequentially written as color frame simultaneous signal data into freezing memories 265R, 265G and 265B (represented by the reference numeral 265). The R, G and B picture image signal data written into the above mentioned freezing memories 265 are sequentially read out and output as synchronized with the synchronized signals of a displaying apparatus or processing apparatus not illustrated connected to the later step.

The color frame simultaneous signal data read out of the above mentioned respective memories 264R, 264G and 264B are simultaneously led also to a movement detecting circuit 266 and the movement detected amount of the object output from this movement detecting circuit 266 is output to the level discriminating circuit 214. Now, if a picture image freezing directing signal is issued from the foot switch 35' as a freezing directing switch, the output of the level discriminating circuit 214 will be able to be output to the writing-in inhibiting gate 215 and, in case the movement detected amount of the object is smaller than the preset value, the writing into the freezing memories 265 will be inhibited by this writing-in inhibiting gate 215 and the picture image just before this prohibition will be frozen.

Figure 31:
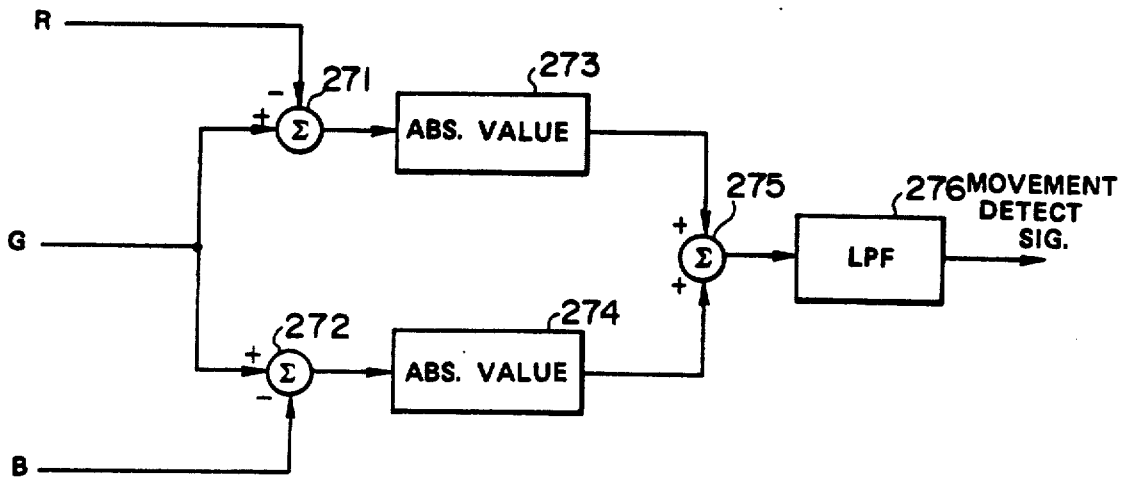
FIG. 31 is a [formation] *schematic* view of a movement detecting circuit in the sixth embodiment.

An example of the movement detecting circuit 266 in this embodiment is shown in FIG. 31.

As the respective R, G and B primary color picture images imaged by the R, G and B color frame sequential imaging system are generated in time series, for example, in the order of R, G and B in the system, the movement of the object will appear as the difference between the respective picture images of R and G, G and B and B and R. Therefore, the difference between the picture images is determined on at least one of between R and G, G and B and B and R and, by using it, the movement detected amount can be operated.

In the example shown in FIG. 31, the difference between the picture images is determined on both between R and G and between G and B. That is to say, the color signal R synchronized by the memory 264 is applied to the subtraction input end of a subtracting circuit 271, the synchronized color signal B is applied to the subtraction input end of a subtracting circuit 272 and the synchronized color signal G is applied to the respective addition input ends of the above mentioned subtracting circuits 271 and 272. The difference between the R and G picture image signals and the difference between the G and B picture image signals are determined respectively in the above mentioned subtracting circuits 271 and 272, are respectively made absolute values in absolute value circuits 273 and 274, are then added in an adding circuit 275 and are output as movement detected amounts of the object through an LPF 276.

By the way, the electronic scope 2 shown in FIG. 1 or the television camera 63 fitted to the eyepiece part 64 of the fiber scope 60 shown in FIG. 8 can be used as an example of the imaging means using a color frame sequential system.

The operation and effect of this sixth embodiment are the same as of the fifth embodiment shown in FIG. 25.

Figure 32:
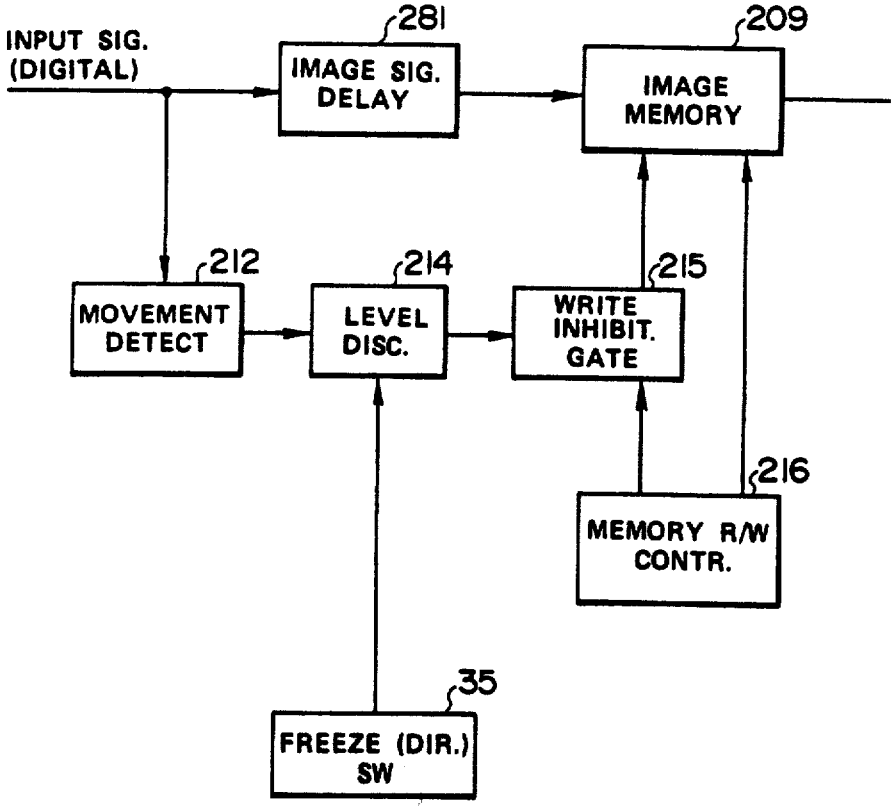
FIG. 32 is a block diagram showing the formation of an essential part of another modification of the fifth embodiment.

FIG. 32 shows an essential part of another modification of the fifth embodiment shown in FIG. 25.

That is to say, a picture image signal delaying means 281 is provided in front of the picture image *memory* 209 in FIG. 25 and delays the picture image signal data input into the picture image memory 209.

The reason why the above mentioned picture image signal delaying means 281 is provided shall be described in the following.

For example, in the embodiments shown in FIGS. 25 and 30, the movement amount of the object is detected from the sequentially input picture image signals and the freezing is controlled on the basis of its value but it is thought that, in case a delaying element is included in the movement detecting circuit (for example, 214), if picture images are continuously input, [when] whether the freezing is possible or not is judged by detecting the movement amount, a new picture image input will already start and a picture image at [the] *a* time [next] *subsequent* the picture image having *just* had the movement detected will be frozen. If the movement of the object is not so sharp, the object of the present invention will be well attained with the above mentioned formation but, in case it is not so, though the movement detecting circuit is correctly operating, an image having an image fogging or color smear will be frozen to disadvantage.

In this embodiment, such disadvantage as is described above is eliminated. As shown in FIG. 32, in the fifth embodiment, the picture image signal delaying means 281 is added to the input step of the picture image memory 209 and the delay amount of the movement detecting circuit 212 is corrected by this picture image signal delaying means 281 so that, in case the freezing operation is made with a signal judging that the movement amount of the object is below a predetermined value, the next picture image will not be written into the picture image memory 209. That is to say, the picture image signal having had the size of the movement amount investigated through the movement detecting circuit 212 is judged by the level discriminating circuit 214 to be small in the movement amount and coincides with the frozen picture actually held by the picture memory 209.

Figure 33:
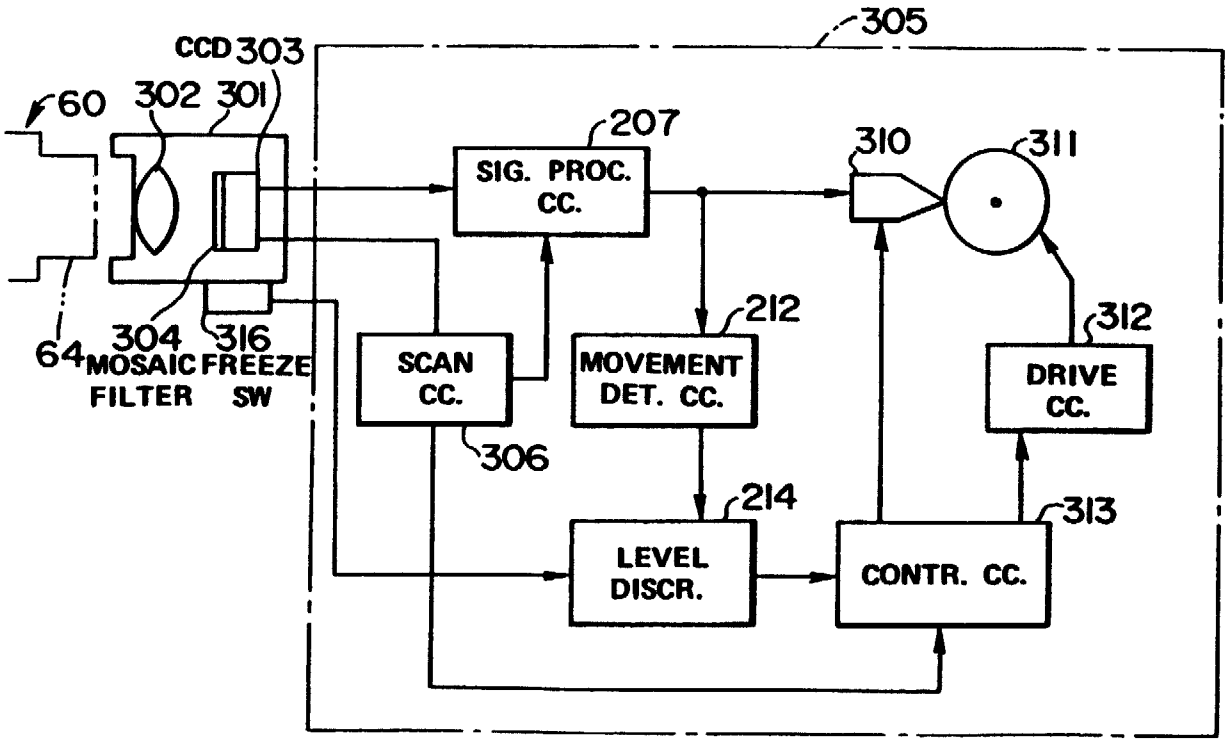
FIG. 33 is a formation view showing the seventh embodiment in the case that a recording medium is used in recording a frozen picture.

In the above described respective embodiments, the frozen picture memorizing means is explained to be formed of a semiconductor memory or the like but, in FIG. 33, an apparatus *wherein* memorizing *is performed* a recording medium is shown.

A television camera 301 fittable to the eyepiece part 64 of the fiber scope 60 shown in FIG. 8 contains an image forming lens 302 and CCD 303. A color separating mosaic color filter 304 is fitted to the front surface of this CCD 303.

A driving signal is applied to the above mentioned CCD 303 by a scanning circuit 306 of a recording apparatus 305 and the signal read out of this CCD 303 is input into the signal processing circuit 207.

The picture image signal variously processed by this signal processing circuit 207 is transmitted [to] *through* [header] *recording head* 310 [recording] to a recording medium 311. A driving circuit 312 driving the above mentioned header 310 and recording medium 311 is controlled by a control circuit 313.

The picture image signal from the above mentioned signal processing circuit 207 is simultaneously input also into a movement detecting circuit 212 and the movement amount of the object is detected by this movement detecting circuit 212. The output of the above mentioned movement detecting circuit 314 is input into a level discriminating circuit 214 started by a freezing switch 316 provided, for example, in the television camera 301 as a recording directing means. The discriminating signal output from this level discriminating circuit 214 becomes a picture image freezing controlling signal and is input into the control circuit 313.

When a recording directing signal is issued from the above mentioned freezing switch 316, in the level discriminating circuit 214, the output of the above mentioned movement detecting circuit 212 will be compared with a preset reference value and whether the picture image at that time is to be memorized or not is judged and is transmitted to the control circuit 313. If the movement amount of the object is below a predetermined value, the above mentioned control circuit 313 will control the [header] *recording head* 310 and driving circuit 312 and the picture image signal then will be recorded in the recording medium.

By the way, such various media as a magnetic tape, magnetic disc, photodisc and still video floppy are possible as the above mentioned recording medium 311.

In the above described respective embodiments, the above mentioned movement detecting circuit 212 may be of such analogue system as is shown, for example, in FIG. 19.

The other formation, operation and effect are the same as of the fifth embodiment.

Figure 34:
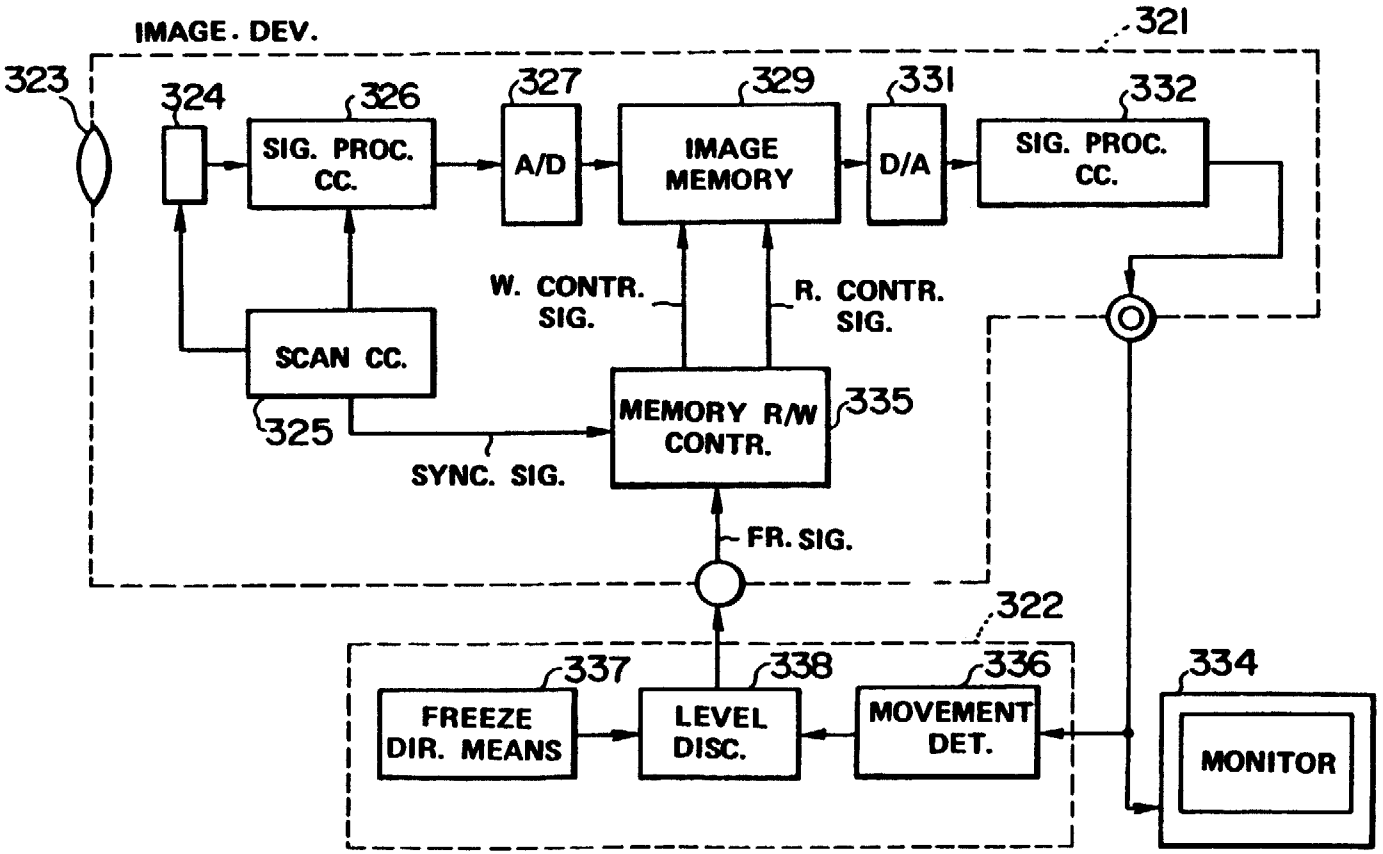
FIG. 34 is a block diagram showing the formation of an apparatus of the eighth embodiment of the present invention.

FIG. 34 shows the formation of an apparatus of the eighth embodiment wherein an imaging apparatus 321 in which an imaging means and signal processing means are made integral and a picture image freezing apparatus 322 as an apparatus attached to this apparatus 322 are made separate from each other.

The above mentioned imaging apparatus 321 is formed as follows. That is to say, the optical image of the object formed on the imaging surface of an imaging device 324 by an imaging optical system 323 is photoelectrically converted by the above mentioned imaging device 324, is scanned under the control of a scanning circuit 325 and is input as a video signal into a signal processing circuit 326 controlled by the above mentioned scanning circuit 325. The picture image signal variously processed by this signal processing circuit 326 is A/D-converted by an A/D converter 327 and is then written into a picture image memory 329. The picture image signal read out of the above mentioned picture image memory 329 is D/A-converted by a D/A converter 331, is then processed by the signal processing circuit 332 and is input into a monitor 334 provided [out] *externally* of the imaging apparatus 321. By the way, the above mentioned picture image memory 329 is controlled in the writing-in/reading-out by a memory R/W controller 335 provided within the imaging apparatus 321. The synchronized signal from the above mentioned scanning circuit 325 is input into this memory R/W controller 335 which is synchronized with the imaging device 324 and signal processing circuit 326.

On the other hand, the picture image freezing apparatus 322 as the above mentioned attached apparatus comprises a movement detecting means 336 detecting the movement of the object from the output picture image from the above mentioned signal processing circuit 332, a freezing directing means 337 and a threshold value circuit 338 started by this freezing directing means 337 and judging whether the freezing is possible or not on the basis of the movement detected amount of the object detected by the above mentioned movement detecting means 336. The judging signal from the above mentioned threshold value circuit 338 is transmitted to the memory R/W controller 335 within the above mentioned imaging apparatus 321.

In this embodiment, when a freezing directing signal is issued from the freezing directing means 337, on the basis of the movement detected amount of the object detected by a movement detecting means 322 from the output picture image signal of the signal processing circuit 332 of the imaging apparatus 321, whether the freezing is possible or not is judged by the threshold value circuit 338 and is transmitted to the memory R/W controller 335 within the imaging apparatus 321. In case the movement amount of the object is judged by the above mentioned threshold value circuit 338 to be below a predetermined value, the picture image will be frozen.

Thus, according to this embodiment, the freezing can be controlled by a remote control. By the way, the signal transmission between the threshold value circuit 338 and the memory R/W controller 335 may be by a wire, wireless or optical method.

The other formation, operation and effect are the same as of the fifth embodiment.

Either of the frame sequential type and simultaneous type can be applied to the above mentioned apparatus in FIG. 34. (In the case of the frame sequential type, the imaging may be made under a frame sequential illuminating light. In the case of the simultaneous type, a mosaic color filter may be provided on the front surface of the imaging device 324.)

Figure 35:
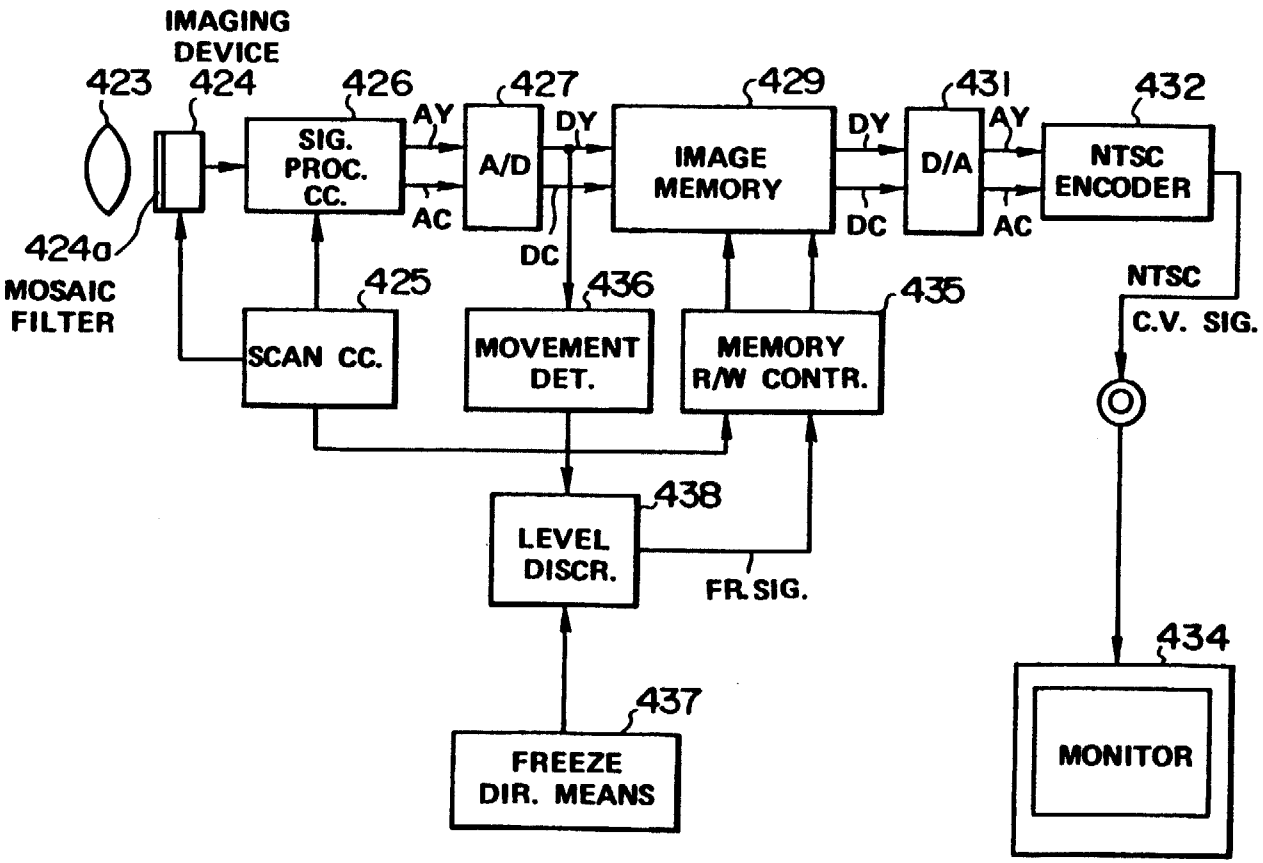
FIG. 35 is a block diagram showing the formation of a concrete example of the eighth embodiment of the present invention.

FIG. 35 shows a simultaneous type apparatus. An object image is formed on an imaging device 424 by an imaging optical system 423. A color mosaic filter 424a for separating colors is provided on the front surface of the imaging surface of this imaging device 424.

A driving signal is applied to this imaging device 424 from a scanning circuit 425. The signal read out of the imaging device 424 by the application of this driving signal is input into a signal processing circuit 426. An analogue luminance signal AY and line sequential analogue color signal AC are produced by this signal processing circuit 426, are converted respectively to a digital luminance signal DY and line sequential digital color signal DC by an AD converter 427 and are then written into a picture image memory 429. The digital luminance signal DY and line sequential color signal DC read out of the above mentioned picture image memory 429 are converted to an analogue luminance signal AY and line sequential color signal AC by a D/A converter 431 and are then converted by an NTSC encoder 432 to an NTSC signal which is input into an outside monitor 434 in which the object image is displayed. By the way, the above mentioned picture image memory 429 is controlled in the writing-in/reading-out by a memory R/W controller 435 into which a synchronized signal from the above mentioned scanning circuit 425 is input to be synchronized with the imaging device 424 and signal processing circuit 426.

The digital luminance signal DY from the above mentioned A/D converter 427 is input also into a movement detecting circuit 496 by which the object movement amount is detected. The output of the above mentioned movement detecting circuit [496] *436* is input into a threshold value circuit 438 started by a freezing directing means 437 and a judging signal is transmitted to the above mentioned R/W controller 435. When a freezing directing signal is issued from the freezing directing means 437, on the basis of the object movement detected amount detected by the movement detecting means 436, whether the freezing is possible or not will be judged by the threshold value circuit 438 and the judging signal will be sent to the memory R/W controller 435. In case the movement amount of the object is judged by the above mentioned threshold value circuit 438 to be below a predetermined value, the picture image will be frozen.

Thus, in this embodiment, the movement of the object is detected from the digital luminance signal DY and the freezing is controlled on the basis of the detected amount. This formation is to detect the movement from the luminance signal DY in consideration of the visibility of the human eye. In case the movement is wanted to be detected by noting particularly the color of the object, the movement may be detected by using the digital color signal DC.

The other formation, operation and effect are the same as of the fifth embodiment.

By the way, the above mentioned respective embodiments are not limited to those shown in the drawings and can be applied, for example, also to a monitor picture image photographing apparatus.

Now, as in the above mentioned respective embodiments (for example, in FIG. 25 or 29), in case the movement amount becomes below the reference value by the level discriminating circuit 214, if a frozen picture is to be obtained, due to a time lag for obtaining the frozen picture, in some case, the timing of imaging will be likely to be missed.

Therefore, in the following respective embodiments, a frozen picture imaging apparatus is formed so that a frozen picture having no time lag or little image fogging may be selected by the user.

Figure 36:
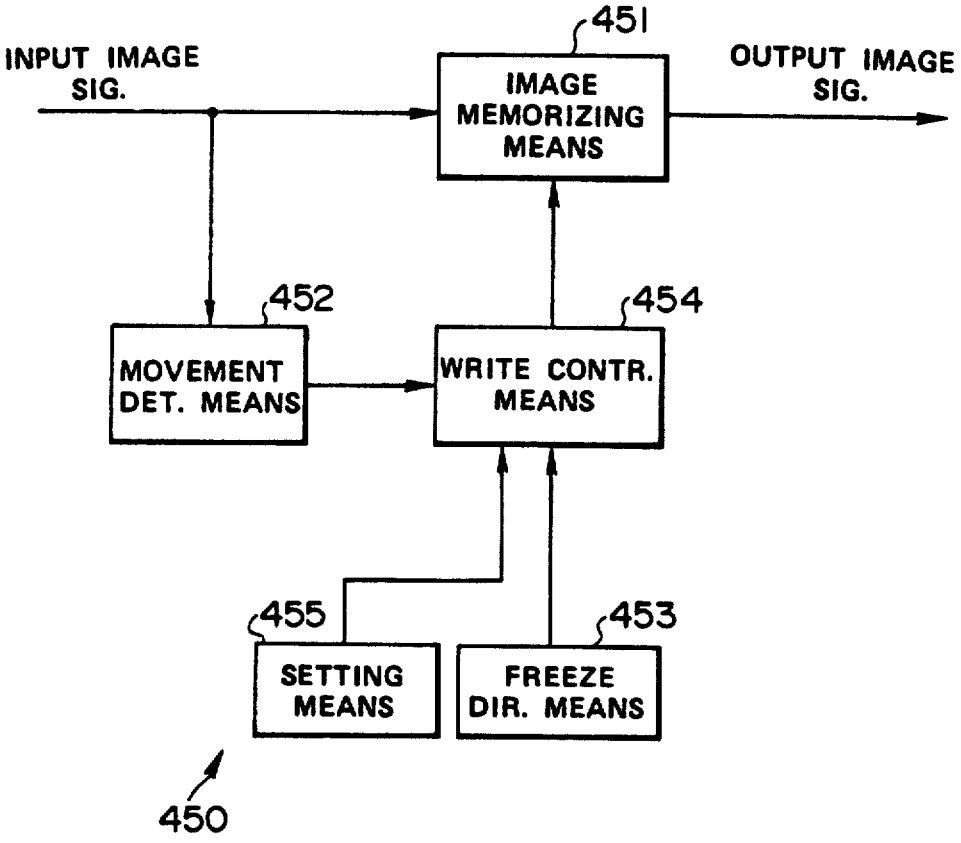
FIG. 36 is a block diagram showing the fundamental formation of an essential part of the ninth embodiment of the present invention.

FIG. 36 shows the fundamental formation of a frozen picture imaging apparatus. This apparatus 450 comprises a picture image memorizing (recording) means 451 memorizing or recording an input picture image signal from a photoelectric converting means, a movement detecting means 452 detecting the movement of an object from the above mentioned picture image signal, a frozen picture directing means 453 directing to memorize or record a frozen picture in the above mentioned picture image memorizing means 451, a writing-in (recording) controlling means 454 started by a frozen picture directing signal from this directing means 453 and controlling the operation of writing or recording the input picture image signal into the above mentioned picture image memorizing means 451 and a setting means 455 setting the control on this writing-in controlling means 454 on or not on the basis of the output of the above mentioned movement detecting means 452.

By the above mentioned formation, [when] whether the picture image memorizing means is to be controlled by the controlling means 454 in response to the movement detecting signal output from the movement detecting means 452 or by neglecting this movement detecting signal is directed by the setting means 455 and it is directed to memorize or record the frozen picture, the writing-in controlling means 454 will be started by the frozen picture directing signal from the frozen picture directing means 453 and will control the operation of writing or recording the input picture image signal into the picture image memorizing means 451 in response to or by neglecting the movement detecting signal output from the above mentioned movement detecting means 452 in accordance with the setting of the above mentioned setting means 453. Thereby, a frozen picture will be memorized or recorded in the above mentioned picture image memorizing means 451.

Figure 37:
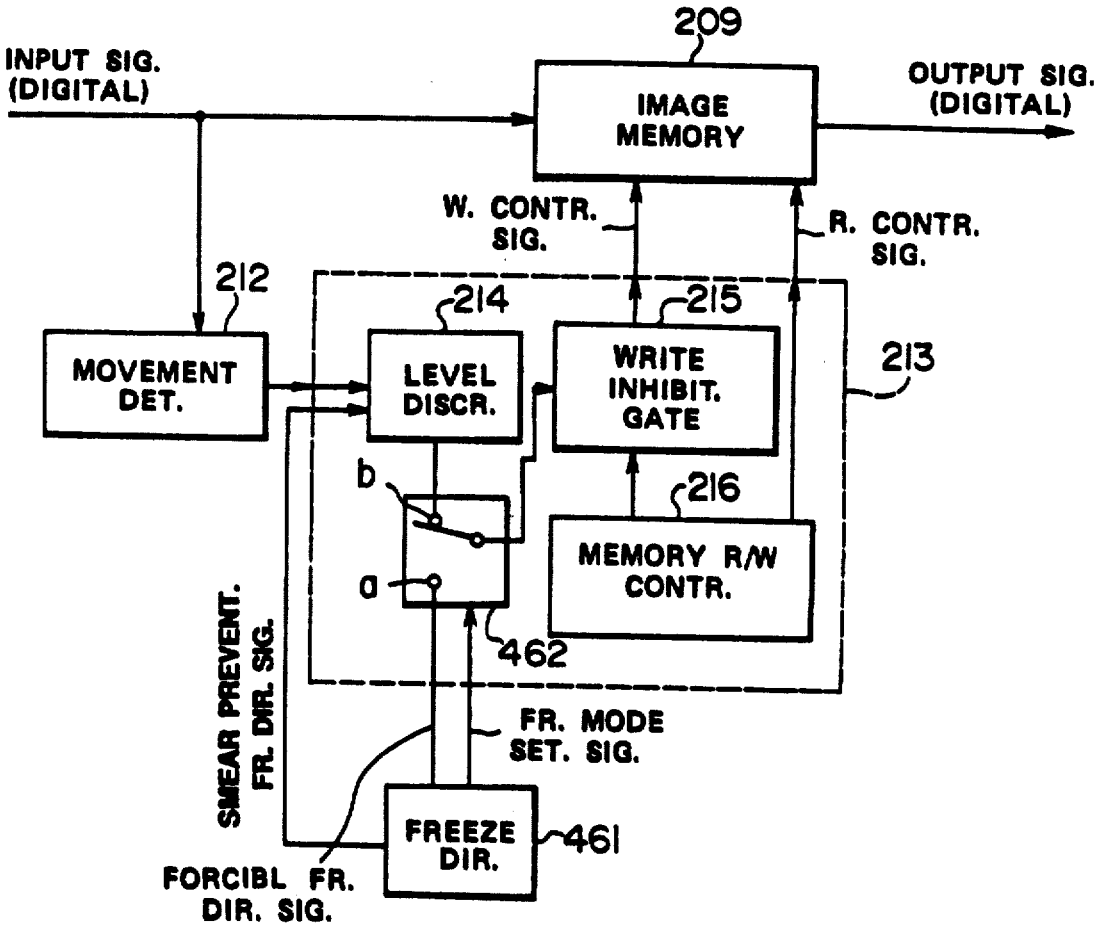
FIG. 37 is a block diagram showing an essential part of a modification of the fifth embodiment shown in FIG. 25.

FIG. 37 shows the formation of an essential part in case *the apparatus* FIG. 36 is applied to *the imaging system shown in* FIG. 25.

In FIG. 37, in the WRITE/READ controlling circuit 213 in FIG. 25, a freezing directing switch 461 corresponding to the picture image freezing switch 35 is provided so that the selection of a freezing mode switching circuit 462 may be controlled by this directing switch 461 and a forcible freezing directing signal may be output through a line connected to one contact a of the freezing mode switching circuit 462 which is connected at the other contact b to the output end of the level discriminating circuit 214.

The same as in the case of FIG. 25, the above mentioned directing switch 461 can output to the level discriminating circuit 214 a freezing directing signal, that is, a directing signal directing a frozen picture image having few smears.

The [others] *other components* are the same as of the embodiment in FIG. 25.

The operation of this embodiment shall be explained in the following:

The input picture image signal is led to the picture image memory 209 and movement detecting means 212. The movement detected amount corresponding to the movement of the object is determined from the input picture image signal in the movement detecting means 212 and the value is output to the level discriminating circuit 214 provided within the WRITE/READ controlling means 213. On the other hand, the picture image signal input into the picture image memory 209 is controlled in the writing-in/reading-out by the memory R/W controller 216 provided within the WRITE/-READ controlling means 216 so that, at the normal time, sequentially input picture images may be sequentially output as they are and moving pictures may be displayed in an [outside] *external* displaying apparatus not illustrated. By the way, in this case, the above mentioned level discriminating circuit 214 will not be started and the writing-in inhibiting gate 215 will not prohibit the writing-in.

On the other hand, in the case of memorizing a frozen picture, either forcible or smear preventing freezing mode is set in advance by the freezing directing means 461 and the freezing operation is started on the basis of the picture image freezing signal output from the above mentioned freezing directing means 461. In the smear preventing freezing mode in this embodiment, the freezing mode switching circuit 462 in FIG. 37 is switched to the level discriminating circuit 214 side. In this mode, the picture image freezing directing signal from the above mentioned freezing directing means 461 is transmitted to the level discriminating circuit 214, the output of this level discriminating circuit 214 is made enable, the output of the movement detecting means 212 is compared with a preset reference value, the size of the object movement is judged and a judging signal showing it is transmitted to the writing-in inhibiting gate 215. In this writing-in inhibiting gate 215, when the movement of the object is large, the writing-in will not be inhibited and the moving picture display will be continued as it is but, when the movement of the object is judged to be small, the writing into the picture image memory [1] *209* will be inhibited and the picture image will be frozen.

On the other hand, when the forcible freezing mode is selected, the above mentioned freezing mode switching circuit 462 shown in FIG. 37 will be switched to the freezing directing means 461 side and the forcible freezing directing signal from this freezing directing means 461 will be transmitted to the writing-in inhibiting gate 215. In this mode, a forcible freezing directing signal is issued from the above mentioned freezing directing means [416] *461* and is transmitted to the writing-in inhibiting gate 215 through the freezing mode switching circuit 462. In this writing-in inhibiting gate 215, in response to this forcible freezing directing signal, the writing into the picture image memory 209 is immediately prohibited and the picture image is frozen.

Figure 38:
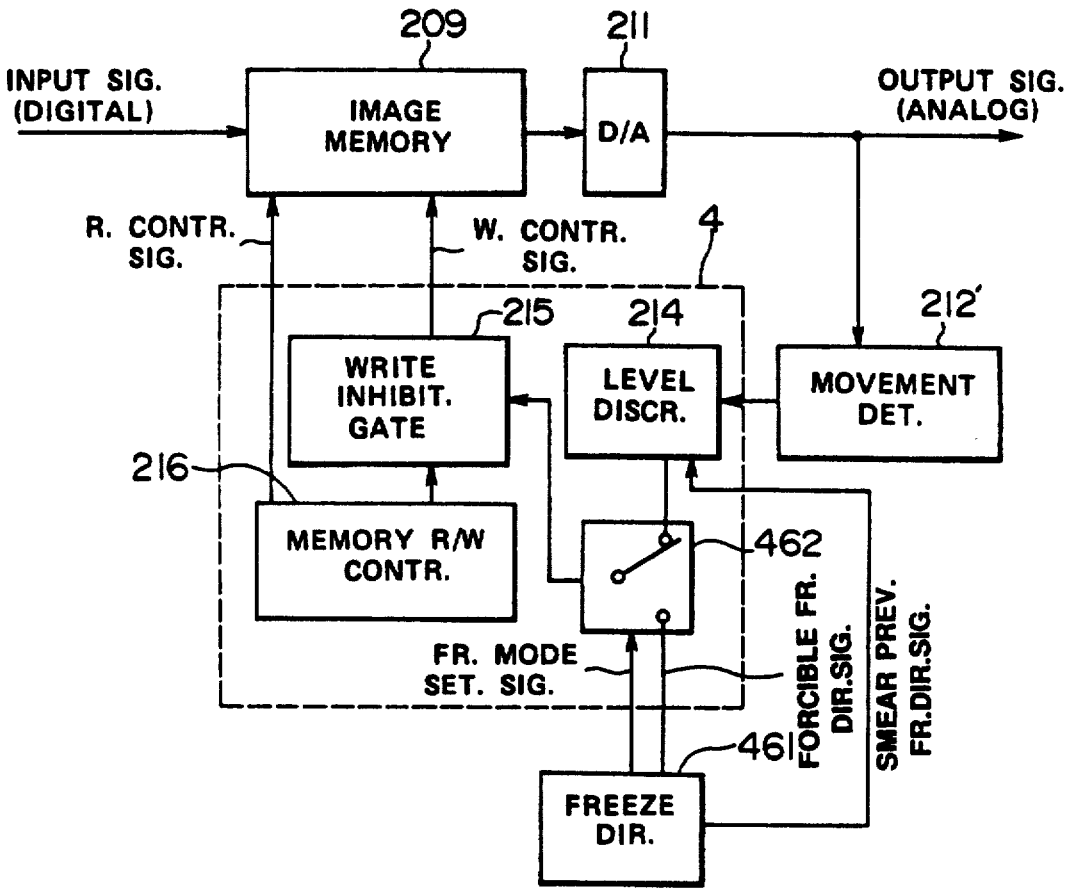
FIG. 38 is a block diagram in the case that the modification in FIG. 29 is provided with a freezing mode switching means.

In FIG. 38, the freezing mode switching circuit 462 is provided in the modification shown in FIG. 29. The same as in FIG. 37, the forcible freezing as well as the smear preventing freezing can be directed.

Figure 39:
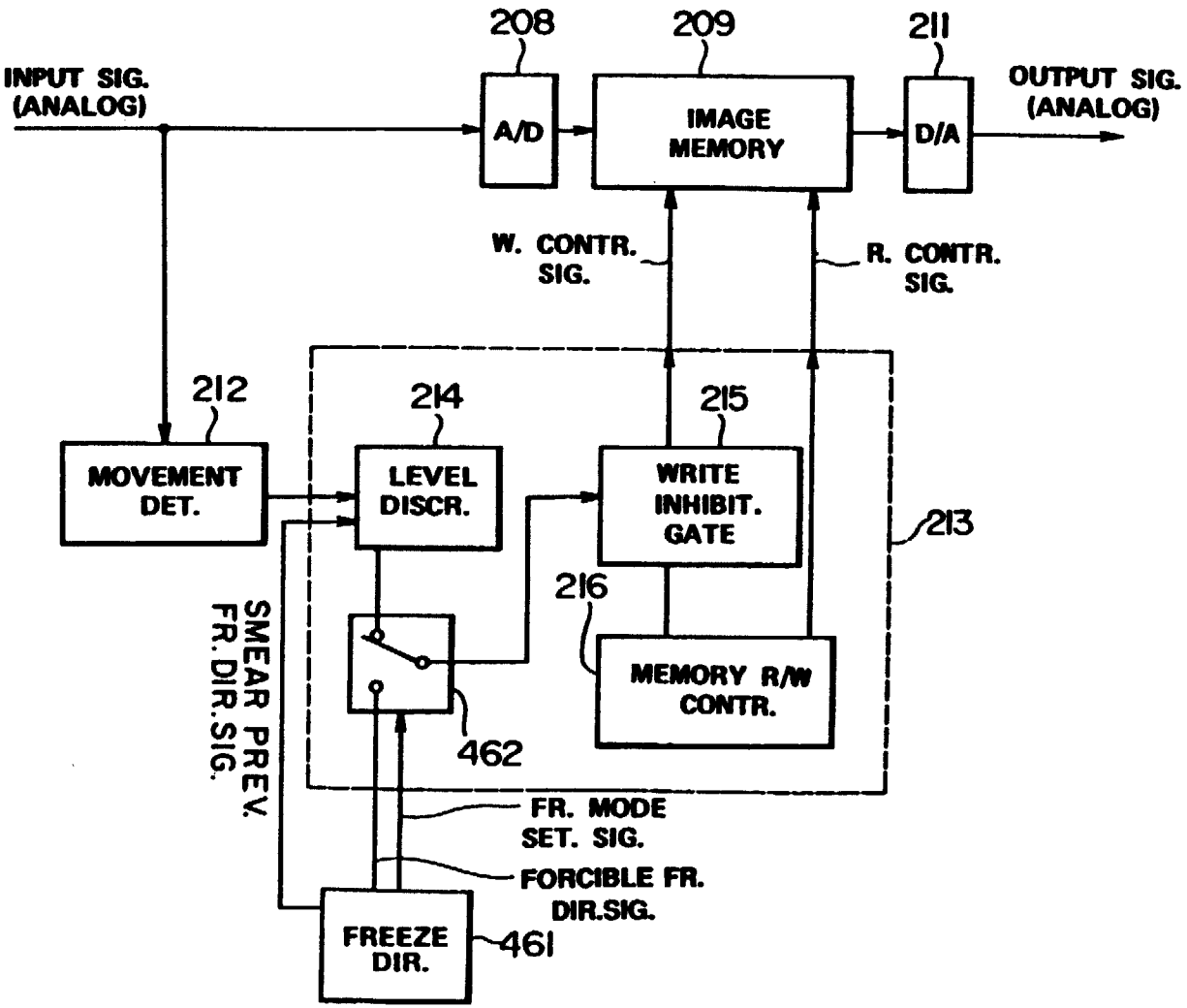
FIG. 39 is a block diagram in the case that the movement detecting means is made to be of an analogue type in FIG. 38.

In FIG. 39, the analogue type movement detecting circuit 212' is used in *place of the digital detecting circuit shown in* FIG. 37.

Figure 40:
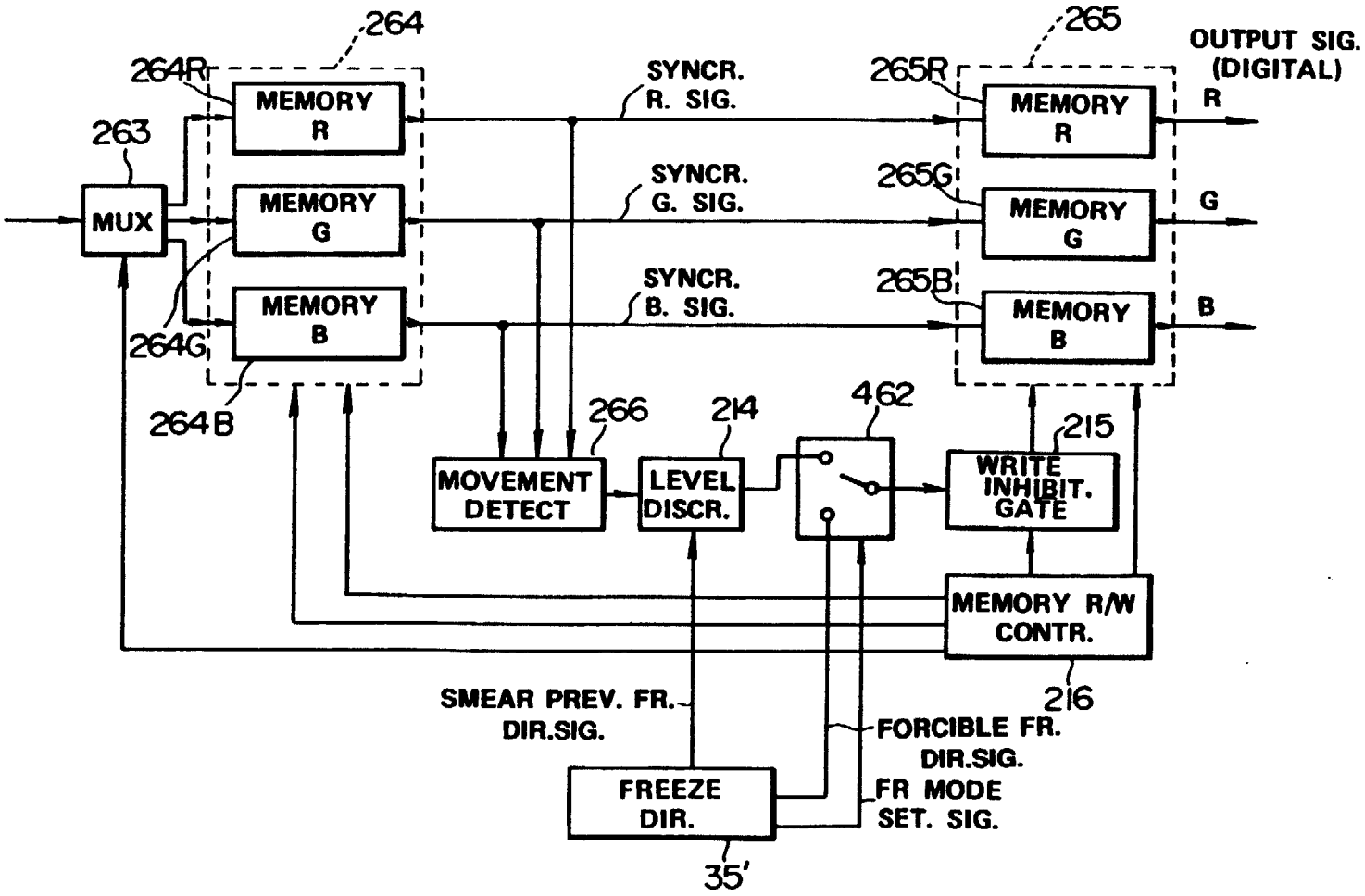
FIG. 40 is a block diagram in which the embodiment shown in FIG. 30 is provided with a freezing mode switching means.
Figure 41:
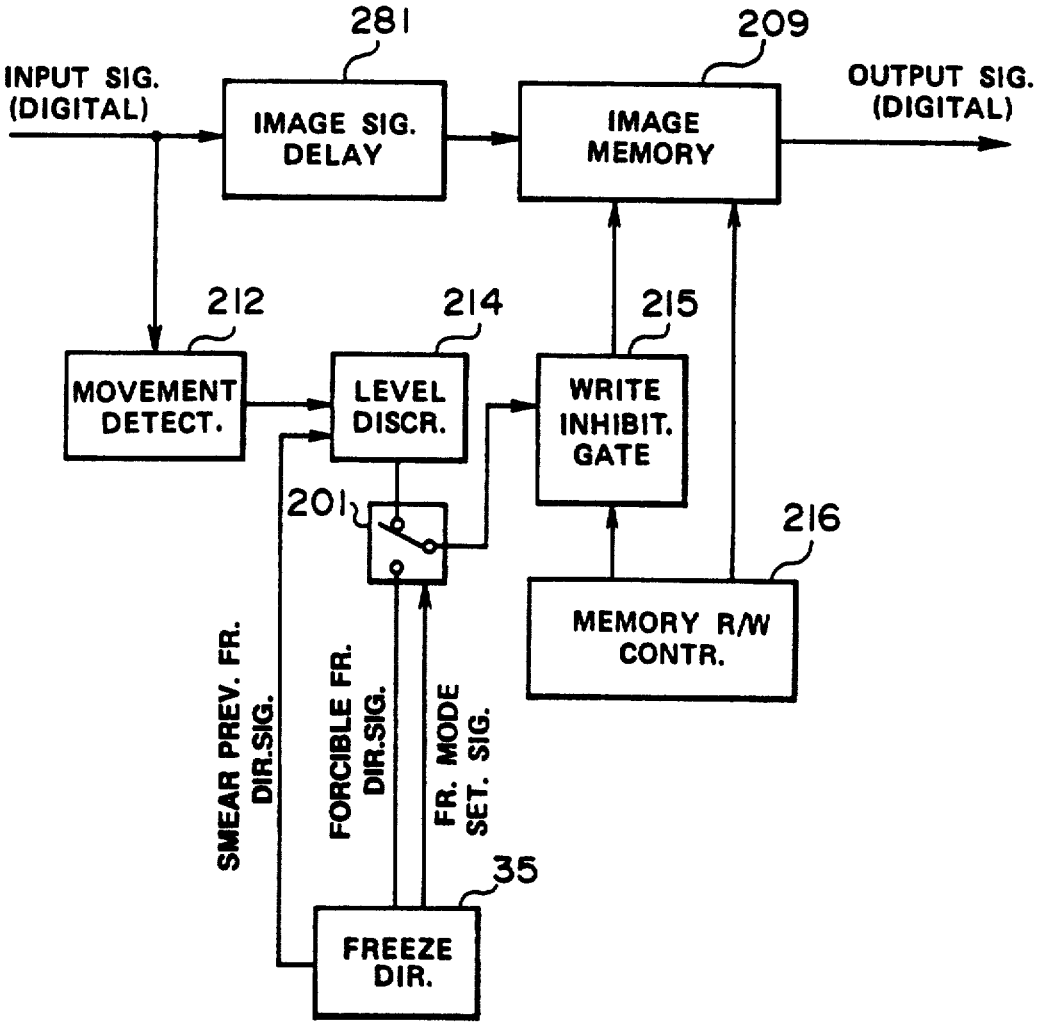
FIG. 41 is a block diagram in which the embodiment shown in FIG. 32 is provided with a freezing mode switching means.

In FIG. 40, the system in FIG. 30 is provided with the freezing mode switching circuit 462 so that the color smear preventing freezing and forcible freezing may be selectively directed.

Figure 42:
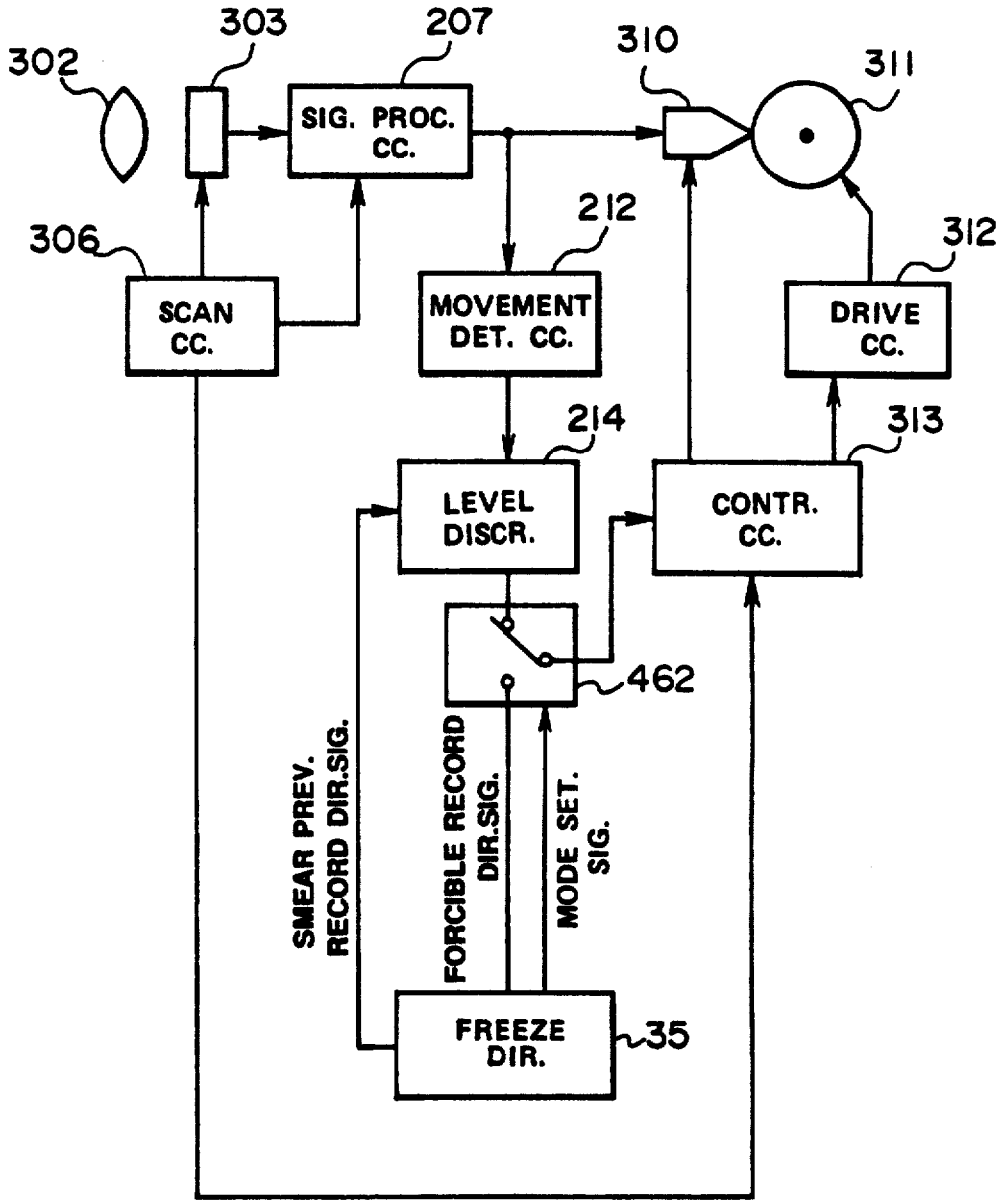
FIGS. 42, 43 and 44 are block diagrams of modifications provided with freezing mode switching means in the embodiments shown respectively in FIGS. 33, 34 and 35.

In FIG. 42, the apparatus in FIG. 33 is provided with a freezing mode switching means.

Figure 43:
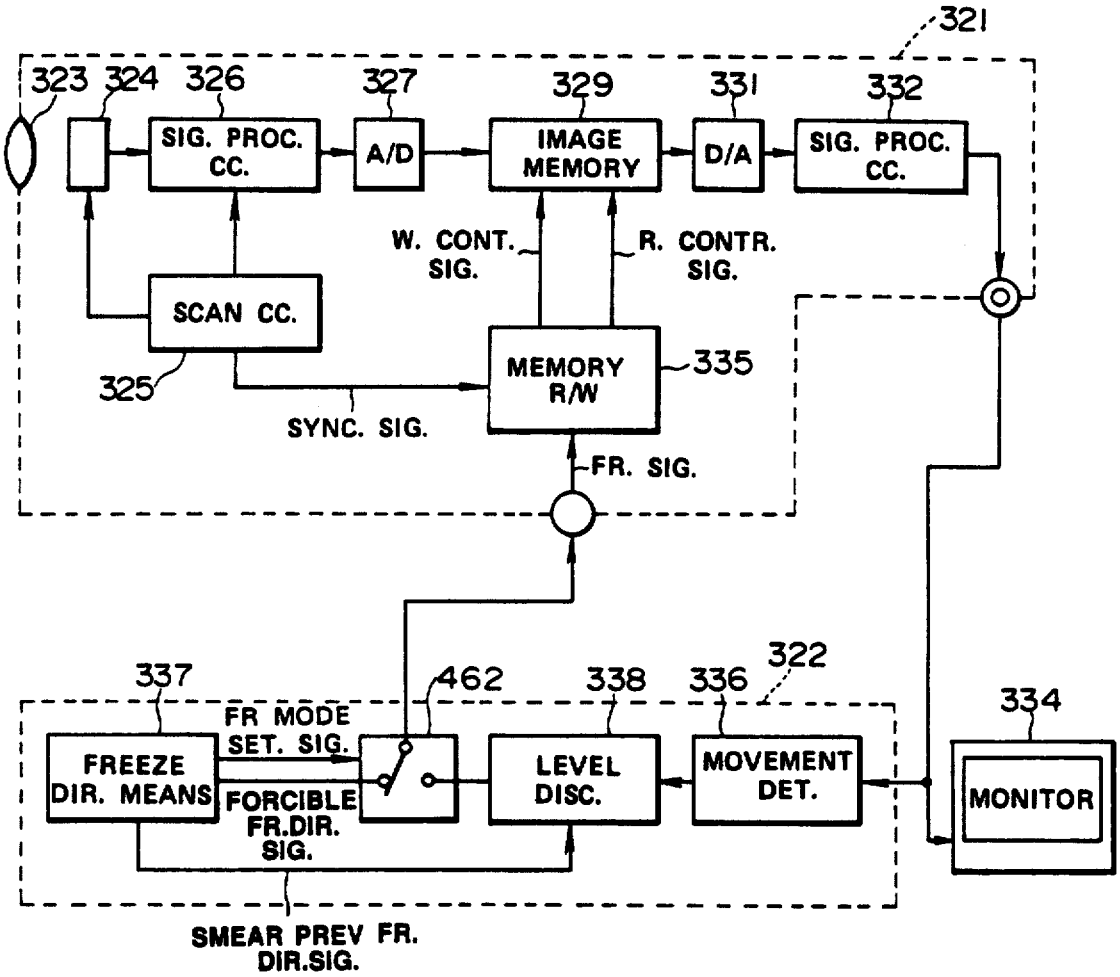
Figure 44:
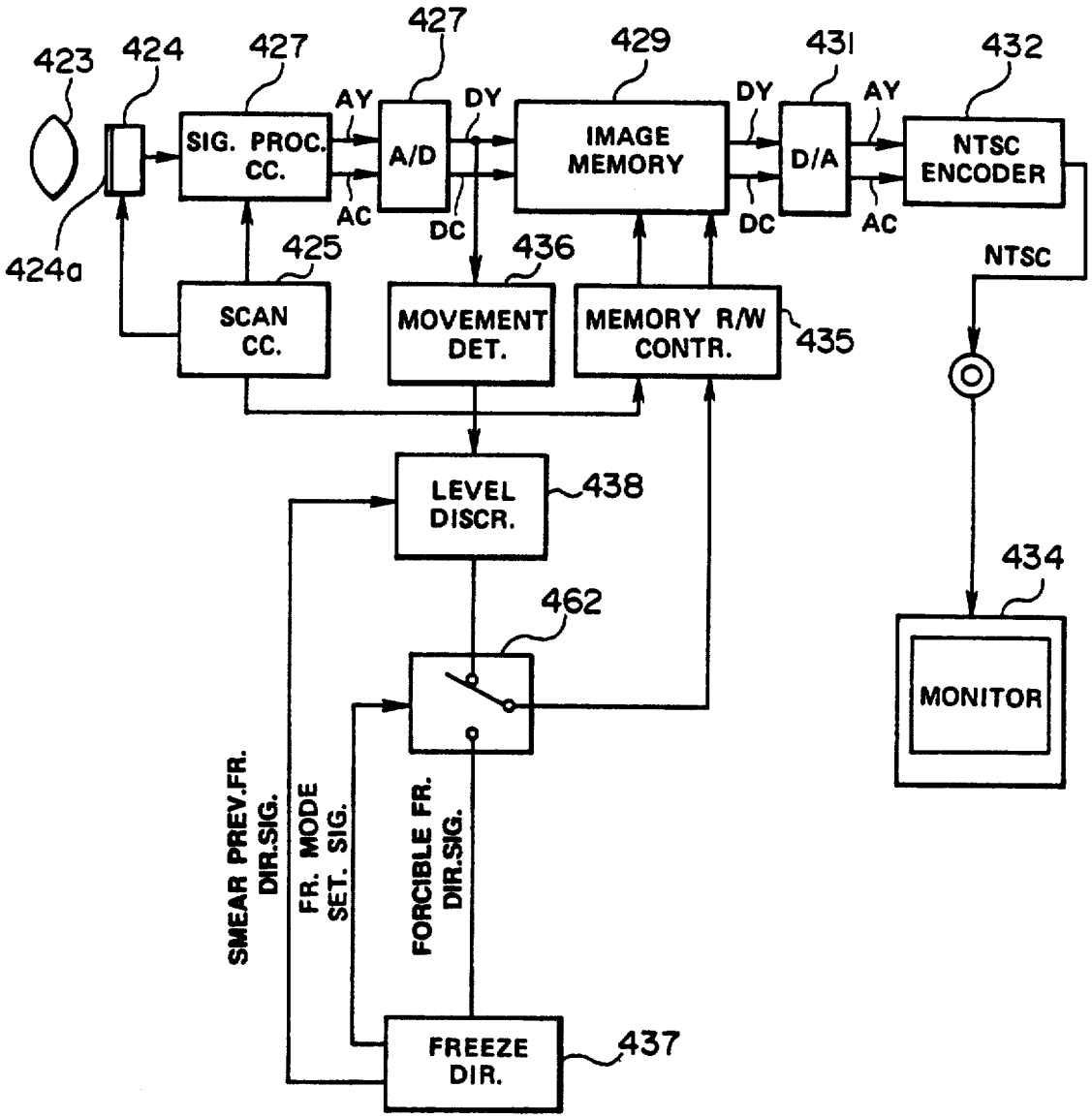

In FIGS. 43 and 44, the respective apparatus in FIGS. 34 and 35 are provided respectively with freezing mode switching means.

By the way, the above mentioned freezing mode switching means may be provided in such other embodiments as the first embodiment.

Figure 45:
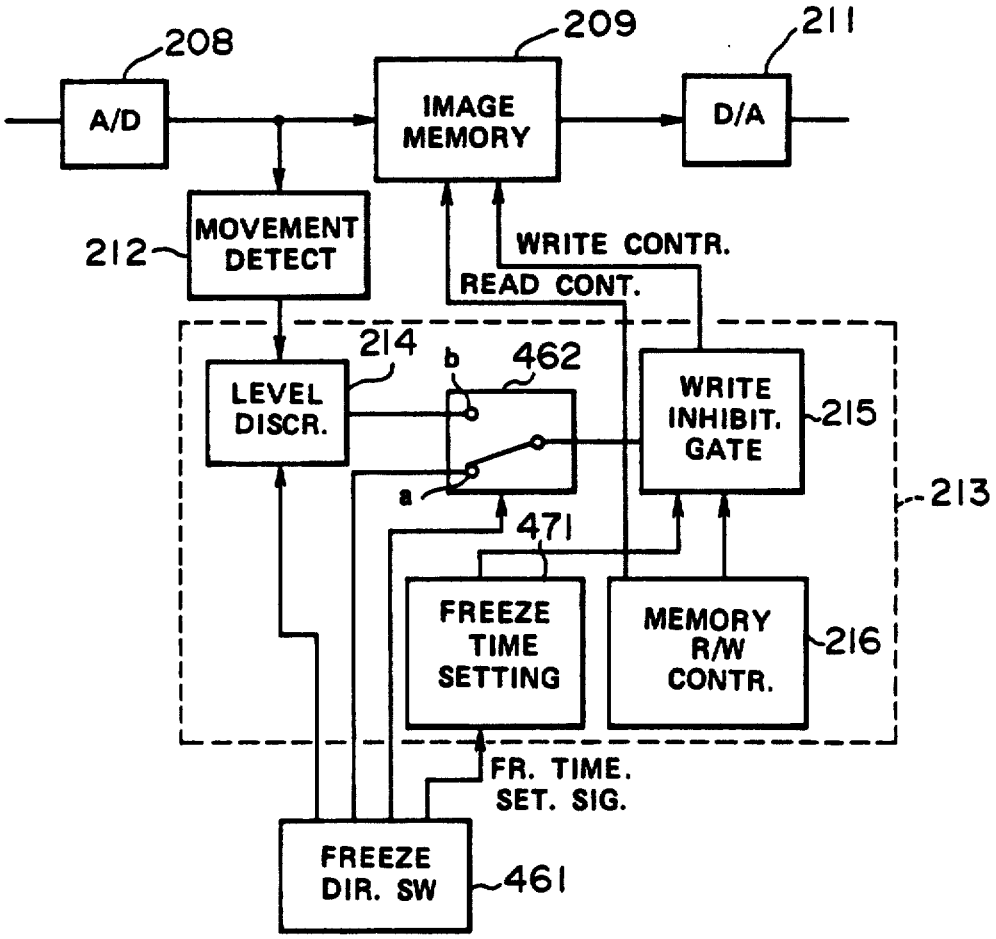
FIG. 45 is a block diagram in which the embodiment shown in FIG. 37 is further provided with a freezing time setting means.

FIG. 45 shows a WRITE/READ controlling circuit part provided with a time setting circuit whereby the freezing time can be selected [besides] *in addition showing* a freezing mode switching means, for example, in the embodiment in FIG. 25.

That is to say, as in FIG. 37, the freezing time setting circuit 471 is provided [besides] *in addition to* the freezing mode switching circuit 462.

The above mentioned freezing time setting circuit 471 can variably set the writing-in inhibiting time of the writing-in inhibiting gate 215 by the freezing directing switch 461 and is formed, for example, of a time settable timer or the like. In case it is formed of this timer, the set time of the timer will be able to be selectively set by the time selecting signal of the freezing directing switch 461.

Therefore, in the case of the forcible freezing mode, when the freezing directing switch 461 is operated, the freezing time setting circuit 471 will prohibit the writing-in for a set time T and will hold the picture image data of the picture image memory 209. On the other hand, in the case of the smear preventing freezing mode, the frozen picture holding time T will become shorter by the time lag by the level discriminating circuit 214.

Figure 46:
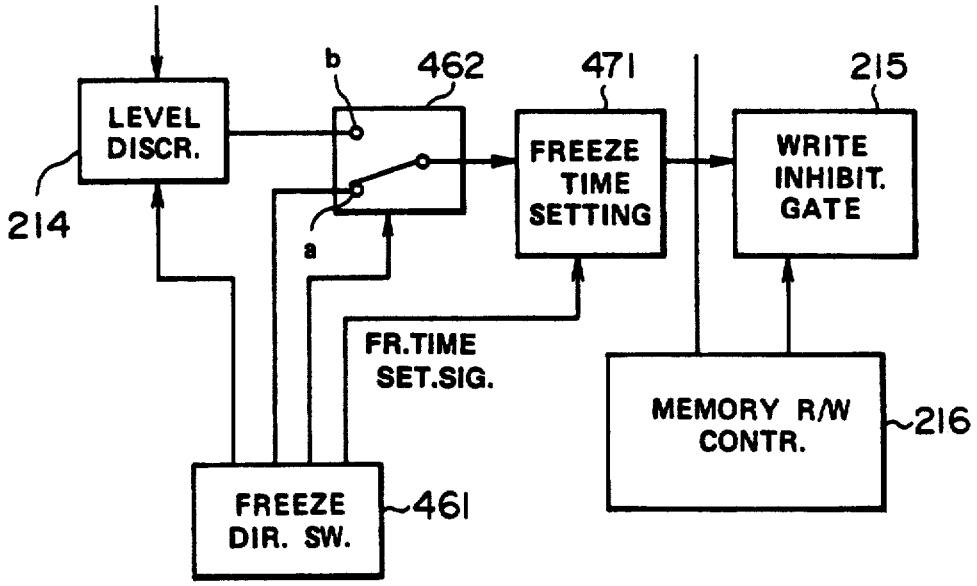
FIG. 46 is a block diagram showing a part of the modification in FIG. 45.

In order to make the freezing holding (freezing displaying) times of both modes coincide with each other, as shown in FIG. 46, the freezing time setting circuit 471 may be provided between the freezing mode switching circuit 462 and writing-in inhibiting gate 215.

The operation of this embodiment shall be explained in the following:

The input picture image signal is led to the picture image memory 209 and movement detecting means 212. In the above mentioned movement detecting means 212, a movement detected amount corresponding to the movement of the object is determined from this input picture image signal and is output to the level discriminating circuit 214 provided within the WRITE/READ controlling means 213. On the other hand, the picture image signal input into the picture image memory 209 is controlled in the writing-in/reading-out by the memory R/W controller 216 provided within the WRITE/-READ controlling means 213 so that, at the normal time, the sequentially input picture images may be sequentially output as they are and may be displayed as moving pictures in an [outside] *external* displaying apparatus not illustrated. By the way, in this case, the above mentioned level discriminating circuit 214 will not be started and the writing-in inhibiting gate 215 will not inhibit the writing-in.

On the other hand, in the case of memorizing frozen pictures, it will be directed by the freezing directing switch 461.

Even in this embodiment, the forcible freezing mode and smear preventing freezing mode described in FIG. 37 are provided. In setting them, the freezing mode setting signal from the freezing directing switch 461 is transmitted to the time setting circuit 471 and the writing-in inhibiting gate 215 is controlled for the period from the freezing direction to the freezing operation by this time setting circuit 471.

When a picture image freezing directing signal is issued from the above mentioned freezing directing means 461 and is transmitted to the level discriminating circuit 214, the output of this level discriminating circuit 214 will be enabled, the output of the movement detecting means 212 will be compared with a preset reference value, the size of the object movement will be judged and the judging signal will be transmitted to the writing-in inhibiting gate 215. In this writing-in inhibiting gate 215, when the movement of the object is large, the writing-in will not be prohibited and the moving picture displaying will be continued as it is but, on the other hand, when the movement of the object is judged to be small, the writing into the picture image memory 209 will be prohibited and the picture image will be frozen.

By the way, it is apparent that the freezing time setting means in FIG. 45 or 46 can be provided in the other embodiments.

Further, in this formation, both of the freezing mode setting signal and freezing directing signal are issued from the freezing directing means (or a recording directing means corresponding to it) but may be issued by respective separate means.

Figure 47:
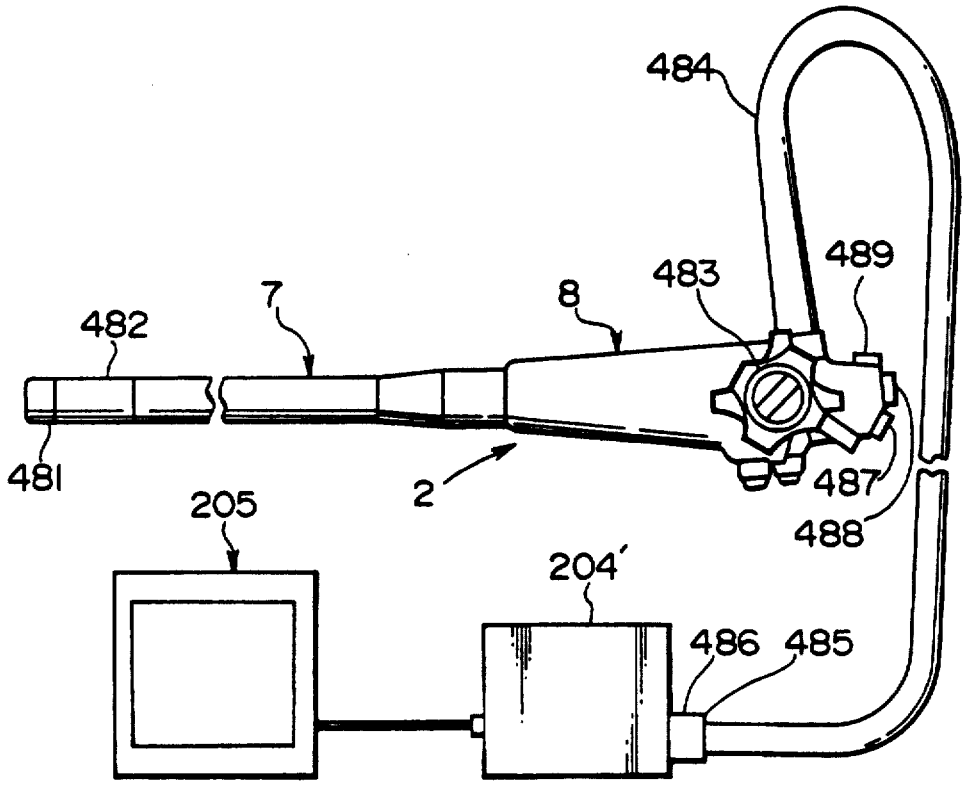
FIG. 47 is a contour view of an electronic scope.

The [contour] *general construction* of an electronic scope to which the above mentioned freezing directing means is fitted is shown in FIG. 47. [In the one] *The electronic scope shown in FIG. 47 is used with* a video processor 204' integrating the light source unit 203 and [divide] *video* processor 204 in FIG. 25.

The electronic scope 2 is provided with an elongate and, for example, flexible insertable part 7, a rigid tip part 481 on the tip side of this insertable part 7 and a [curvable] *flexible* part 482 of a proper length in the rear part adjacent to this tip part 481. This [curvable] *flexible* part 482 can be curved vertically and horizontally by rotating a [curving] *flexing* operation knob 483 provided in an operating part 8.

A universal cord 484 is extended from the side of the above mentioned operating part and a connector 485 fitted to the end of this universal cord 484 can be connected to a connector receptacle 486 of the video processor 204'.

Further, a freezing mode setting switch 487, freezing directing switch 488 and freezing time setting switch 489 are provided, for example, on the tip side of the operating part 8.

Figure 48:
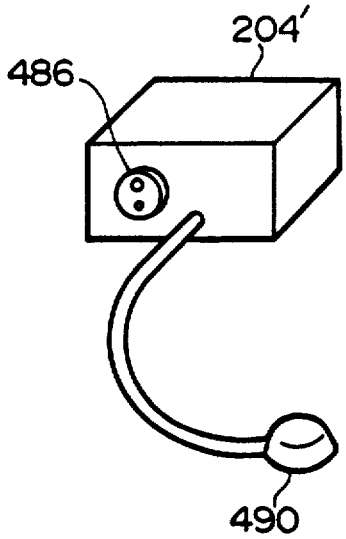
FIG. 48 is a view showing a foot switch provided on a video processor.

In FIG. 47, the freezing directing switch 488 is provided on the electronic scope 2. However, as shown in FIG. 48, it may be operated in the same manner also by a foot switch 490 extended from the video processor 204'.

Figure 49:
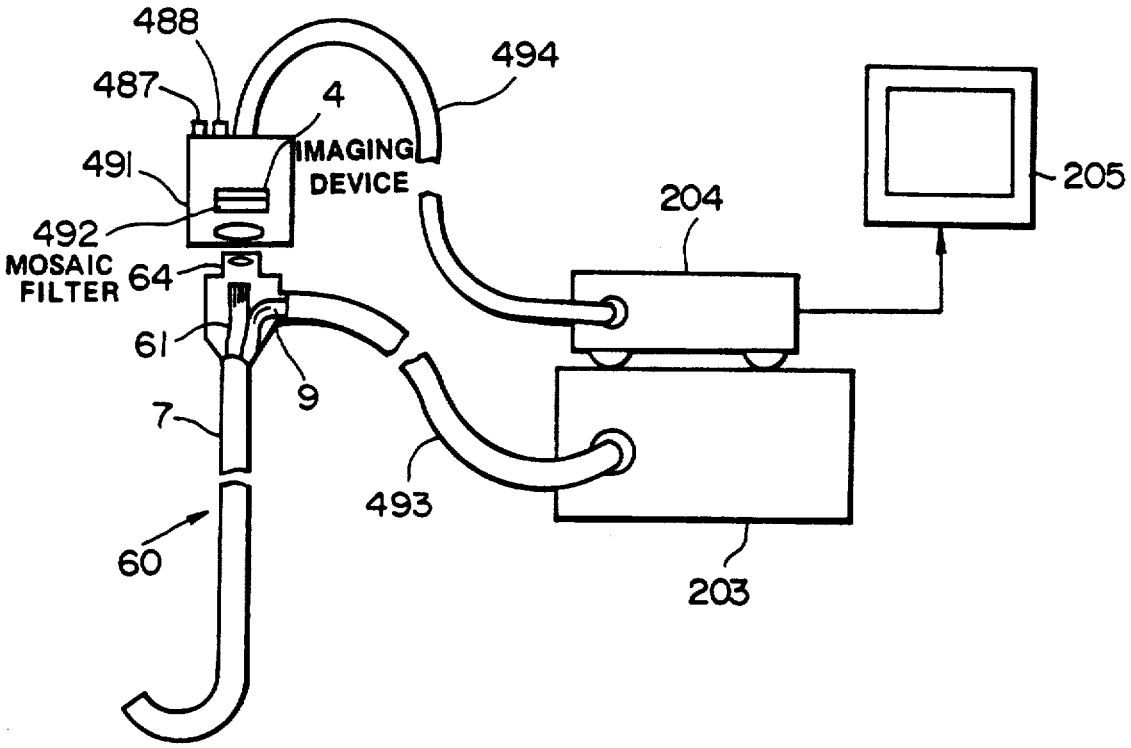
FIG. 49 is a contour view of a fiber scope and a television camera connectable to this fiber scope.

FIG. 49 shows the [contours] *general construction* of a fiber scope 60 usable instead of the electronic scope 2 and a television camera 491.

The formation of the above mentioned fiber scope 60 is shown in FIG. 8. This television camera 491 fitted to the eyepiece part 64 of this fiber scope 60 is provided with a freezing mode setting switch 487 and freezing directing switch 488 in the television camera 63 shown in FIG. 8. This television camera 491 is shown to be of a simultaneous type wherein a mosaic color filter 492 is fitted to the front surface of the imaging device 4.

Therefore, in this case, a light guide cable 493 extended out of the operating part 8 of the fiber scope 60 is connected to a light source unit 203 (for example, in FIG. 25) outputting a white light.

The signal cable 494 of the television camera 491 is connected to a simultaneous type video processor (for example, 204).

By the way, as shown in FIG. 48, the picture image freezing directing means may be provided on the video processor 204 side.

The respective embodiments of a system of memorizing as a frozen picture the picture image of the least movement amount within a set time after the freezing direction shall be explained in the following:

First of all, the fundamental formation and operation shall be explained with reference to FIGS. 50 and 51.

As shown in the conceptional view in FIG. [36] *50*, a picture image freezing apparatus comprises a movement detecting means 501 detecting the movement of an object from an input picture image signal, a least value detecting means 504 started by a picture . At freezing directing means 502 and detecting from the output of the above mentioned movement detecting means 501 the least value of the movement amount of the object at least within a predetermined time set, for example, by a set time detecting means 503 and a controlling means 506 controlling the operation of writing or recording the above mentioned input picture image signal into a picture image signal memorizing or recording means 505 in response to the output of the above mentioned least value detecting means 504.

In the above mentioned formation, the movement of the object is detected as movement amounts from sequentially input picture image signals by the movement detecting means 501 and the respective movement amounts are input into the least value detecting means 504 started by the picture image freezing directing means 502. As shown in FIG. 51, the started least value detecting means 504 compares the sequentially input respective movement amounts within the time ($t_2$—$t_1$) set by the set time detecting means 503. For example, when the least value of the movement is detected, the detecting signal will be sent to the controlling means 506 controlling the operation of writing or recording the picture image signal. When this controlling means 506 receives the detecting signal from the least value detecting means 504, it will control the operation of writing or recording the input picture image signal into the picture image signal memorizing or recording means 505 and will make a freezing operation. By the above operation, as shown in FIG. 51, the picture image signal of the least movement among the respective picture image signals input within the set time is operated to be frozen.

Figure 51:
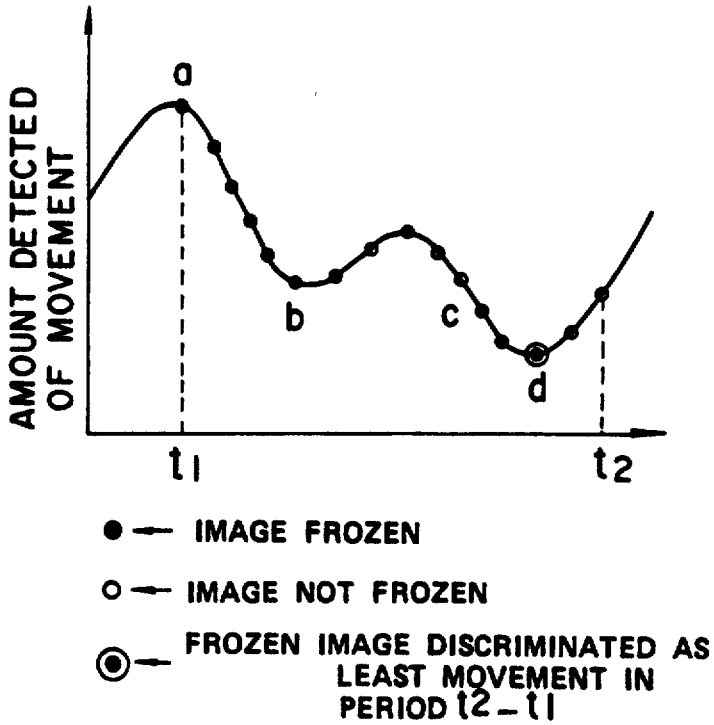
FIG. 51 is a view for explaining the operation in FIG. 50.

By the way, in FIG. 51, the black circle represents a frozen picture image, the white circle represents a non-frozen picture image and the double circle with the black circle inside represents a frozen picture image judged to be of the least movement within the ($t_2$—$t_1$) period. In the example in this graph, the picture image of the movement amount a at the time $t_1$ is frozen, the movement amount sequentially becomes smaller thereafter and therefore the picture image until the movement amount becomes the minimum value b is frozen. Thereafter, between the picture images before the picture image of the movement amount c, the movement amount is above b and therefore the picture image is not frozen. As the movement amount is again below b from the picture image of the movement amount c, finally the picture image of the least movement amount d within the ($t_2$—$t_1$) period is frozen.

Figure 52:
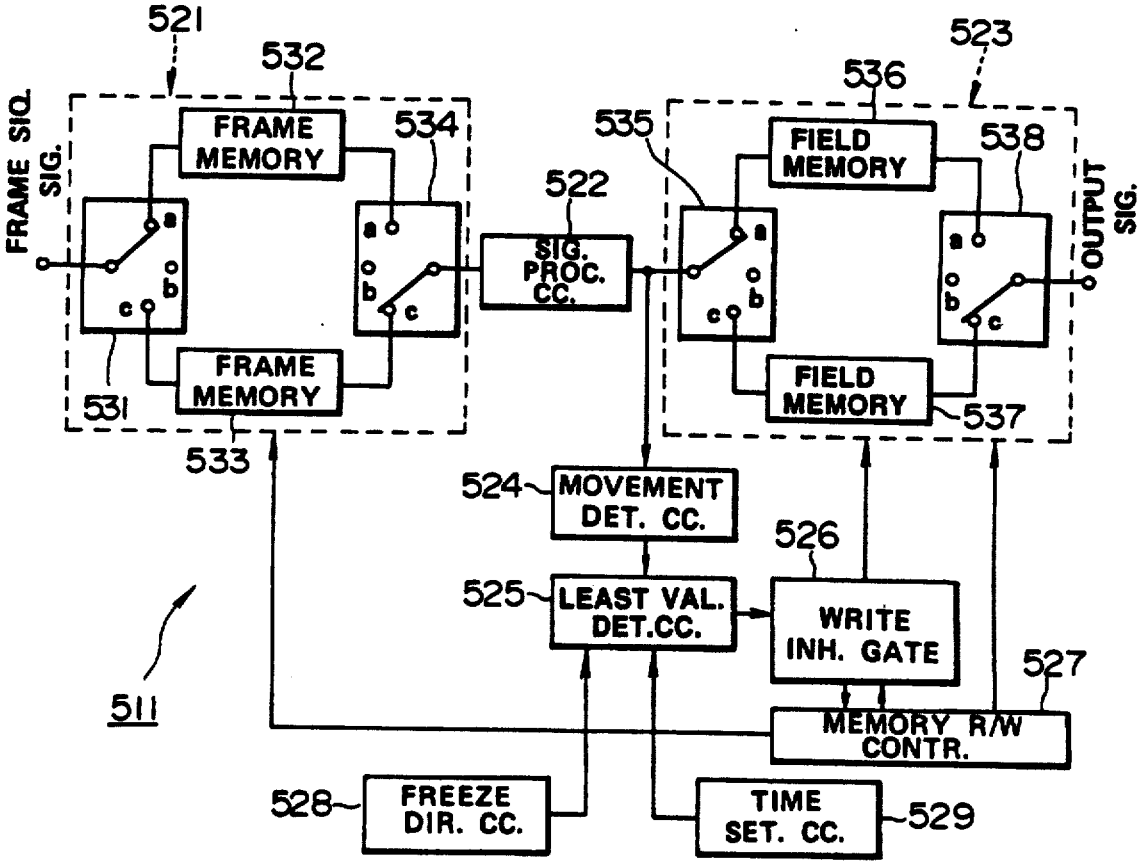
FIG. 52 is a block diagram showing the concrete formation of the tenth embodiment.

The tenth embodiment in FIG. 52 shall be explained in the following:

As shown in FIG. 52, a picture image freezing apparatus 511 comprises a synchronizing memory 521 synchronizing a digital color frame sequential signal, that is, a primary color signal of a picture image input in time series, a signal processing circuit 522 expanding and interpolating the picture image of the output picture image signal of this synchronizing memory 521 and a freezing memory 523 capable of freezing the output picture image of this signal processing circuit 522. The output picture image signal of the above mentioned freezing memory 523 is output to a displaying apparatus and processing apparatus in the later step.

The above mentioned synchronizing memory 521 is formed as follows. That is to say, a color frame sequential signal is applied to the input end of a switching switch of one input and three outputs. A first frame memory 532 is connected to the output end a of the three output ends a, b and c of this switching switch 531 and a second frame memory 533 is connected to the output end c. The output of the above mentioned first frame memory 532 is applied to the input end a of the three input ends a, b and c of a switching switch 534 of three inputs and one output and the output of the above mentioned second frame memory 533 is applied to the input end c of the above mentioned switching switch 534. The output end of this switching switch 534 is connected to the above mentioned signal processing circuit 522.

The above mentioned freezing memory 523 is formed as follows. That is to say, the output picture image signal of the above mentioned signal processing circuit is applied to the input end of a switching switch 535 of one input and three outputs. A first field memory 536 is connected to the output end a of the three output ends a, b and c of this switching switch 535. A second field memory 537 is connected to the output end c. The output of the above mentioned first field memory 536 is applied to the input end a of the three input ends a, b and c of a switching switch 538 of three inputs and one output. The output of the above mentioned second field memory 537 is applied to the input end c of the above mentioned switching switch 538. A digital picture image signal is output from the output end of this switching switch 538.

The above mentioned synchronizing memory 521 and freezing memory 523 are controlled in the writing-in and reading-out by a memory R/W controller (which shall be mentioned as a memory controller hereinafter) 527. By the way, the writing-in controlling signal from the memory controller 527 to the above mentioned freezing memory 523 is transmitted to the freezing memory 523 through a writing-in inhibiting gate circuit 526.

By the way, the respective memories 532, 533, 536, and 537 in the memories 521 and 523 are represented by representing the three memories of R, G and B.

The picture image freezing apparatus 511 in this embodiment further comprises a movement detecting circuit 524 detecting the movement of the object from the output signal of the above mentioned signal processing circuit 522, a least value detecting circuit 525 detecting the least value of the movement amount within a predetermined time, a freezing directing circuit 528 starting this least value detecting circuit 525 and a setting time detecting circuit 529 setting the time when the above mentioned least value detecting circuit 525 detects the least value. The above mentioned writing-in inhibiting gate circuit 526 is controlled by the above mentioned least value detecting circuit 525.

The synchronized primary color signal from the above mentioned signal processing circuit 522 is transmitted also to the movement detecting circuit 524 in which the movement amount of the object is detected from the correlation of the respective primary color signals. This movement amount is detected, for example, by calculating the difference between the pixels corresponding to any two primary color signals of one frame or the difference between the pixels corresponding to the respective primary color signals multiplied by the coefficient and detecting as a movement amount the accumulated value of the absolute values of the respective differences.

When a picture image freezing directing signal is input into the least value detecting circuit 525 by the freezing directing circuit 528, this least value detecting circuit 525 will sequentially receive the movement amounts of the respective frames from the movement detecting circuit 524, will compare the sequentially input respective movement amounts within a time set by the set time detecting circuit 529 and will transmit, in response to the result, a control signal to the memory controller 527 through the writing-in inhibiting gate circuit 526.

The operation of this embodiment shall be explained in the following with reference to FIG. 53.

First of all, at the normal time when the picture image is not frozen, the primary color signals of picture images input in time series will be sequentially written into one of the first frame memory 532 and second frame memory 533 alternately for each frame. For example, in some state, as shown in FIG. 52, the output end a of the switch [331] *531* will be made conductive by the control signal from the memory controller [327] *527*, the switch [334] *534* be made conductive at the input end c and the primary color signals of the picture images input in time series will be sequentially written into the first frame memory [332] *532*At this time, in the second frame memory [333] *533*, the respective primary color signals already written in will be simultaneously read out. These picture image signals are processed to have the picture images expanded or interpolated in the signal processing circuit [322] *522* and are then transmitted to the freezing memory [323] *523*.

In this freezing memory [323] *523*, by the control signal from the memory controller [327] *527*, the switch [335] *535* is made conductive at the output end a, the switch [338] *538* is made conductive at the input end c and the picture image signal of the first field transmitted from the above mentioned signal processing circuit [322] *532* is written into the first field memory [336] *536*. At this time, in the second field memory [337] *537*, the picture image signal of the second field of the front frame already written in will be read out.

Next, in the above mentioned freezing memory 523, by the control signal from the memory controller 527, the switch 535 is switched to be conductive at the output end c, the switch 538 is switched to be conductive at the input end a and the picture image signal of the second field transmitted from the above mentioned signal processing circuit 522 is written into the second field memory 537. At this time, in the first field memory 536, the picture image signal of the first field written in by the above mentioned operation will be read out.

Thus, in the color frame sequential system, the sequentially transmitted primary color signal of the picture image is synchronized by the synchronizing memory 521 and is made an output picture image signal through the freezing memory 523.

Now, the case of freezing a picture image shall be explained.

The synchronized primary color signal transmitted to the freezing memory 523 is transmitted also to the movement detecting circuit 524 in which the movement amount of the object is detected by the correlation of the respective primary color signals.

When the picture image freezing directing signal is input into the least value detecting circuit 525 by the freezing directing circuit 528, this least value detecting circuit 525 will receive from the above mentioned movement detecting circuit 524 sequentially the movement amounts of the respective frames.

The movement amount transmitted to the above mentioned least value detecting circuit 525 and the picture image signal written into the freezing memory 523 shall be explained in the following.

Figure 53:
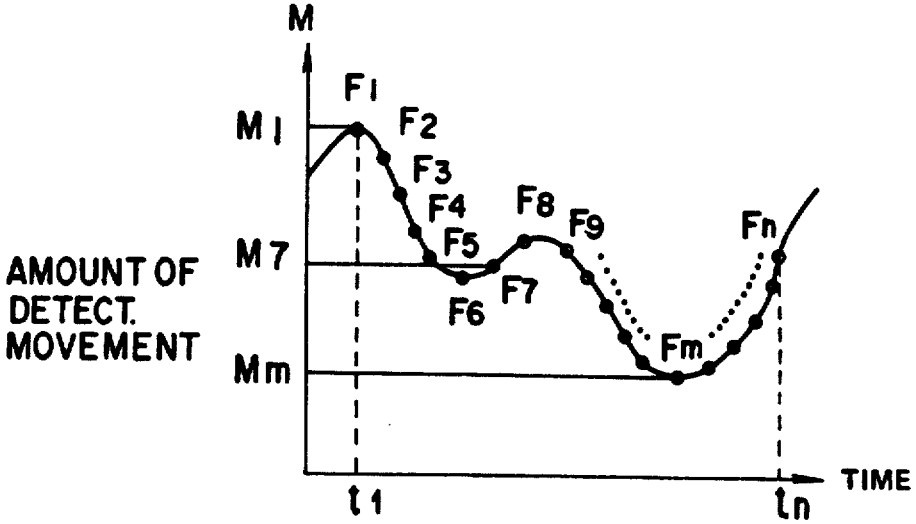
FIG. 53 is an operation explaining view of the tenth embodiment.

As shown in FIG. 53, the time when the least value detecting circuit 525 is started by the picture image freezing signal is represented by $t_1$ and the time when the set time set by the set time detecting circuit 529 ends is represented by $t_n$ ($t_1 < t_n$). The picture image signals of the respective frames read out of the synchronizing memory 521 since the picture image freezing directing signal is output are represented by $F_1$, $F_2$, . . . and $F_n$ and the movement amounts corresponding to them are represented by $M_1$, $M_2$, . . . and $M_n$.

Now, at the time $t_1$, the picture image signal written into the first frame memory 532 of the synchronizing memory 521 shall be $F_2$ and the picture image signal read out of the second frame memory 533 shall be $F_1$. At this time $t_1$, if the picture image freezing directing signal is output, the switch 535 will be made conductive at the output end b by the writing-in inhibiting gate circuit [26] *526* and the writing into the freezing memory 523 will be inhibited. The movement amount $M_1$ of the picture image signal $F_1$ read out by the synchronizing memory 521 is detected by the movement detecting circuit 524.

By the least value detecting circuit 525, the movement amount $M_1$ transmitted from the above mentioned movement detecting circuit 524 is set as an initial value of the least value and a control signal is transmitted to the memory controller 527 through the writing-in inhibiting gate circuit 526 so that the picture image signal $F_1$ written in the second frame memory 533 of the synchronizing memory 521 may be read out once again and may be written into the respective field memories 536 and 537 of the freezing memory 523. At this time, the first frame memory 532 of the synchronizing memory 521 will be writing in and therefore the picture image signal $F_3$ coming next the picture image signal $F_2$ will be written in.

Then, by the memory controller 527, the respective switches 531 and 534 of the synchronizing memory 521 are switched, the first frame memory 532 is made to be reading out and the second frame memory 533 is made to be writing in the picture image signal $F_4$. The switch 535 of the freezing memory 523 is made conductive at the output end b and only the writing into the respective field memories 536 and 537 of the freezing memory 523 is inhibited. By the way, instead of switching to the terminal b, a writing inhibiting signal may be applied to the memories 536 and 537.

On the basis of the picture image signal $F_3$ read out of the synchronizing memory 521, the movement amount $M_3$ is determined by the movement detecting circuit 524 and is compared with the set value $M_1$ by the least value detecting circuit 525. Here, as shown in FIG. 39, if $M_3 < M_1$, the memory controller 527 will be controlled so as to write the picture image signal $F_3$ into the freezing memory 523. In the above mentioned least value detecting circuit 525, instead of $M_1$, the movement amount $M_3$ is set as the least value.

Thus, in case the movement amount renews the least value, the above mentioned operation will be repeated.

Now, the case that the movement amount is larger than the least value shall be explained, for example, with the case of the picture image signal $F_9$. When the picture image signal $F_7$ is written into the freezing memory 523, the picture image signal $F_9$ is written into the frame memory of the synchronizing memory 521 in which the picture image signal $F_8$ is written and the picture image signal $F_9$ written in the synchronizing memory 521 is read out by the memory controller 527, then the movement amount $M_9$ will be determined by the movement detecting circuit 524 and will be compared with the set value $M_7$ by the least value detecting circuit 525. In this case, as shown in FIG. 53, $M_7 < M_9$ and therefore, by the least value detecting circuit 525, a control signal will be transmitted to the memory controller 527 through the writing-in inhibiting gate circuit 526 so that the writing into the freezing memory 523 may be inhibited and the movement amount of the picture image signal $F_{10}$ already written in the synchronizing memory 521 may be determined.

The operation in the case of freezing the picture image as in the above shall be reviewed. In case the movement amount $M_j$ detected by the movement detecting circuit 524 is below the set value of the least value detecting circuit 525, the picture image signal $F_j$ corresponding to the detected movement amount will be once again read out of the synchronizing memory 521 and will be written into the respective field memories 536 and 537 of the freezing memory 523. In this case, the next picture image signal $F_{j+1}$ will be canceled and the movement amount for the next picture image signal will be determined. On the other hand, in case the movement amount $M_j$ detected by the movement detecting circuit 524 is above the set value of the least value detecting circuit 525, the writing into the freezing memory 523 will be inhibited and the movement amount for the next picture image signal $F_{j+1}$ will be determined as different from the above case.

By such operation, the picture image signal $F_m$ corresponding to the least value $M_m$ of the movement amount detected within the set time $(t_n - t_1)$ is written into the freezing memory 523.

By the way, the black circle represents a frozen picture image and the white circle represents a nonfrozen picture image.

Thus, according to this embodiment, the picture image at the time when the movement of the object is the least can be frozen and a frozen picture in which such deterioration of the picture image as the color smear and image fogging is little caused by the movement of the object can be memorized.

Figure 54:
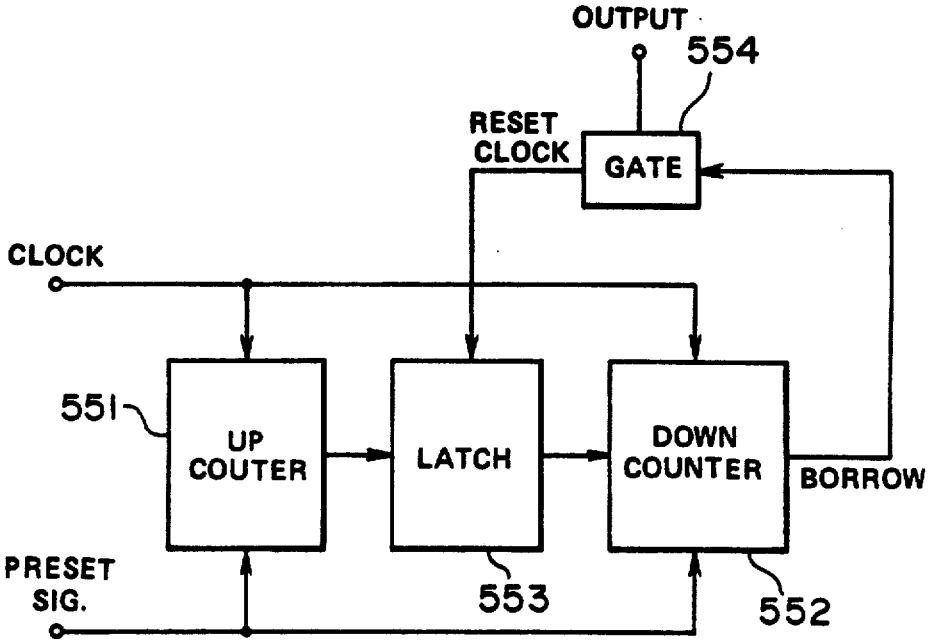
FIG. 54 is a block diagram showing the formation of a digital type least value detecting means in the tenth embodiment.
Figure 55:
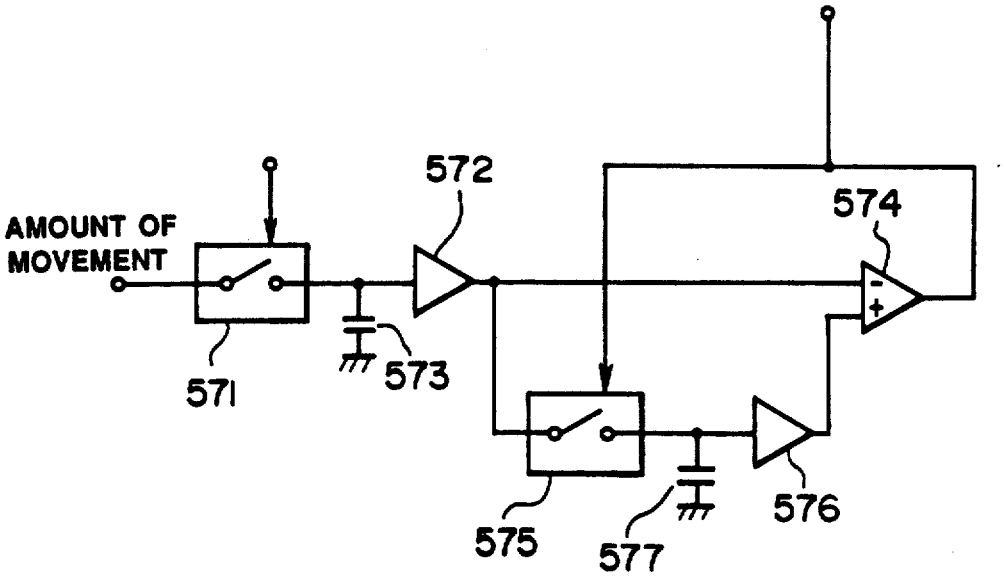
FIG. 55 is a block diagram showing the formation of an analogue type least value detecting means in the tenth embodiment.

Now, the above mentioned least value detecting circuit 525 is formed as shown, for example, in FIG. 54 or 55.

FIG. 54 shows a digital least value detecting circuit. This least value detecting circuit comprises an up counter 551 and down counter 552 preset by a presetting signal and counting [counter clocks] *reverse clock pulses* by the movement amount, a latch 553 holding the output of the above mentioned up counter 551 and a gate circuit 554 transmitting a renewed clock *pulse* to the above mentioned latch 553 and outputting to the writing-in inhibiting gate circuit 526 a control signal for freezing the picture image. When a borrow generated from the down counter 552 is input, the above mentioned gate circuit 554 will not output a renewed clock *pulse*.

When a picture image freezing directing signal is output from the freezing directing circuit 528, the respective counters 551 and 552 of the least value detecting circuit will be set by a presetting signal so that the upper counter will be all Low (0) and the down counter will be all Hi (1) and the number of the movement amounts will be counted.

The respective counters can count the numbers larger than the largest value of the movement amount. Therefore, even if the counting ends, no carry or borrow will be generated from the respective counters 551 and 552. As no borrow is generated from the down counter 552, the gate circuit 554 will transmit a renewed clock to the latch 553 to latch the output of the up counter 551 and will transmit a control signal also to the writing-in inhibiting gate circuit 526 so as to freeze the initial value picture image.

When the next movement amount is detected, by the preset signal, the up counter 551 will be Low (0) and the down counter 552 will receive the output value of the up counter 551 from the latch 553 and will make it a preset value. When the respective counters 551 and 552 are counted by the number of the movement amount and the movement amount is larger than the previous movement amount, the down counter 552 will generate a borrow, the gate circuit 554 will not output a renewed clock and therefore the previous value will become the preset value of the next down counter 552.

On the other hand, when the movement amount is smaller than the previous movement amount, the down counter 552 will not generate a borrow, a renewed clock will be output by the gate circuit 554 and the value of the up counter 551 will be held by the latch 553 and will become the preset value of the next down counter 552.

By the above operation, the least value of the movement amount will be held by the output of the latch 552.

FIG. 55 shows an analogue least value detecting circuit. In this least value detecting circuit, the input end of a buffer 572 is connected to the input end of the movement amount through a switch 571 and is earthed through a condenser 573. The output end of the above mentioned buffer 572 is connected to the inverted input end of a comparator 574 of the TTL output and to the input end of a buffer 576 through a switch 575. The input end of the above mentioned buffer 576 is earthed through a condenser 577. The output end of the above mentioned buffer 576 is connected to the noninverted input end of the above mentioned comparator 574. The output end of the above mentioned comparator 574 is connected to a control input end inputting a signal controlling the opening and closing of the above mentioned switch 575. A control signal from the freezing directing circuit 528 is applied to the respective control input ends of the above mentioned switches 571 and 575.

When a picture image freezing directing signal is output by the freezing directing circuit 528, the condenser 577 of the least value detecting circuit will be fully charged and the value of converting the movement amount to a voltage will be held as a movement amount voltage in the condenser 573 by switching on the switch 571. By the way, at this time, the switch 575 will be OFF. The voltages held in the condensers 573 and 577 by the buffers 572 and 576 are compared by the comparator 574 of the TTL output. At this time, the output voltage of the buffer 576 will be higher than the voltage of the buffer 572, therefore the switch 575 will be switched on by the output of the comparator 574 and the voltage of the buffer 572 will be held in the condenser 577.

When the next movement amount is input by the switch 571, the movement amount will be held by the condenser 573 and will be compared with the previous movement amount held in the condenser 577 by the comparator 574. At this time, if the movement amount held in the condenser 573 is smaller than the movement amount held in the condenser 577, the comparator 574 will output, for example, +5 V, the switch 575 will be ON, he voltage of the condenser 573 will be held in the condenser 577 and the picture image signal of the input movement amount will be written into the freezing memory. On the other hand, if the movement amount held in the condenser 573 is larger than the movement amount held in the condenser 577, the comparator 574 will output 0 volt, the switch 575 will be OFF and the voltage of the condenser 577 will be held.

By the above operation, the least value of the movement amount will be held in the condenser 577.

Thus, according to the tenth embodiment, the picture image at the time when the movement of the object is the least can be frozen and a frozen picture having no deterioration of the picture image caused by the movement of the object can be memorized.

By the way, as examples of the imaging apparatus in which is used the color frame sequential system producing the color frame sequential signal input into the signal processing apparatus of this embodiment, there are an electronic endoscope wherein a monochromatic CCD is fitted to the tip part and the illuminating light is, for example, R, G and B sequential lights and an externally fitted television camera of a frame sequential system removably fitted to the eyepiece part of a fiber scope.

Figure 56:
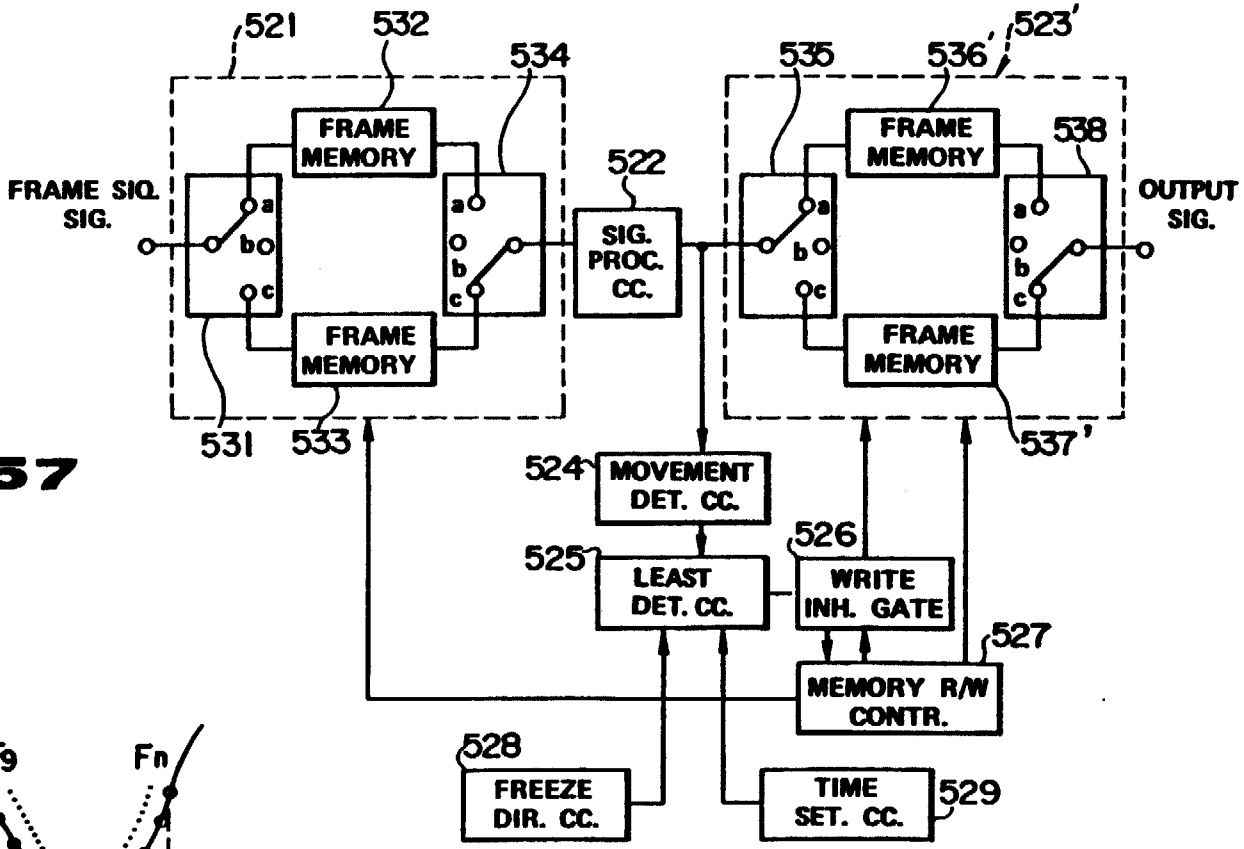
FIG. 56 is a block diagram showing the formation of an essential part of a modification of the tenth embodiment of the present invention.

FIG. 56 shows a modification of the tenth embodiment wherein, instead of the first and second field memories 536 and 537 forming the freezing memory 523 in FIG. 52, a freezing memory 523' formed of the first and second frame memories 536' and 537' is used.

The [others] *other components* are the same as in the tenth embodiment shown in FIG. 52.

The operation of this modification shall be explained in the following.

Picture image signals input in time series are sequentially written into one of the first frame memory 532 and second frame memory 533 alternately for each frame. For example, in some state, an input picture image signal is written into the first frame memory 532 of the synchronized memory 521 and, in the second frame memory 533, the picture image signal already written in is read out. The picture image signal read out of the above mentioned synchronizing memory 521 is transmitted to one frame memory of a freezing memory 536', for example, to the first frame memory 536'. In the second frame memory 537', the picture image signal already written in is read out to be an output picture image signal.

The picture image signal transmitted to the above mentioned freezing memory 523' is transmitted also to the movement detecting circuit 524 to determine the movement amount.

Now, the case of freezing a picture image shall be explained.

Figure 57:
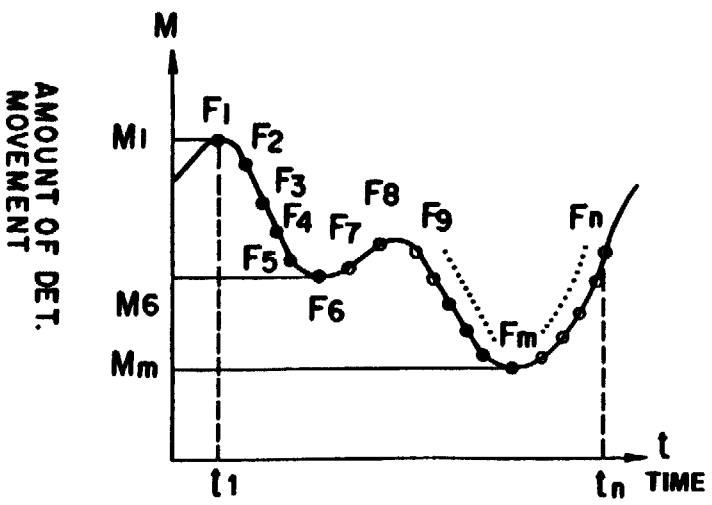
FIG. 57 is an operation explaining view of the modification shown in FIG. 56.

As shown in FIG. 57, the picture image signals of the respective frames read out of the synchronizing memory 521 from the time $t_1$ are represented by $F_1$, $F_2$. . . and $F_n$ and the movement amounts determined by the movement detecting circuit 524 in response to them are represented by $M_1$, $M_2$, . . . and $M_n$. The time when the set time set by the set time detecting circuit 529 ends is represented by $t_n$ ($t_1 < t_n$).

When a picture image freezing signal is output from the freezing directing circuit 528 at the time $t_1$, the picture image signal $F_1$ read out of the synchronizing memory 521 will be written into one frame memory of the freezing memory 523' and at the same time the movement amount $M_1$ will be detected and will be set as an initial value in the least value detecting circuit 525.

When the picture image signal $F_2$ is then read out of the synchronizing memory 521, this picture image signal $F_2$ will be written into the other frame memory (the frame memory other than the frame memory in which the picture image signal $F_1$ is written) of the freezing memory 523' and the movement amount $M_2$ will be detected by the movement detecting circuit 524.

The above mentioned movement amount $M_2$ is compared with the set value $M_1$ of the least value detecting circuit 525. If $M_2<M_1$ as in FIG. 57, the least value detecting circuit 535 will transmit a control signal to the memory controller 527 through the writing-in inhibiting gate 526 to switch the respective switches 535 and 538 of the freezing memory 523' so that the picture image signal $F_2$ may be an output picture image signal. Therefore, the picture image signal next input into the freezing memory 523' will be memorized in the frame memory which is not the frame memory in which the picture image signal of the least movement amount is memorized.

On the other hand, in case the movement amount is larger than the least value as in the picture image signal $F_7$ in FIG. 57, the least value detecting circuit 535 will transmit a control signal to the memory controller 527 through the writing-in inhibiting gate circuit 526 to switch the respective switches 535 and 538 of the freezing memory 523' so that the picture image signal of the least movement amount may be an output picture image signal. Therefore, the picture image signal next input into the freezing memory 523' will be memorized still in the frame memory which is not the frame memory in which the picture image signal of the least movement amount is memorized.

By the way, in FIG. 57, the black circle represents a frozen picture image and the white circle represents a nonfrozen picture image.

In this modification, by such operation as in the above, the movement amounts are detected for all the picture image signals taken into the synchronizing memory 521 and are once written into the freezing memory 523', therefore the detected movement amounts are compared in the least value detecting circuit 535, the picture image of a small movement amount can be read out of the freezing memory 523' and the picture image signal of the least movement can be frozen within the set time.

Figure 58:
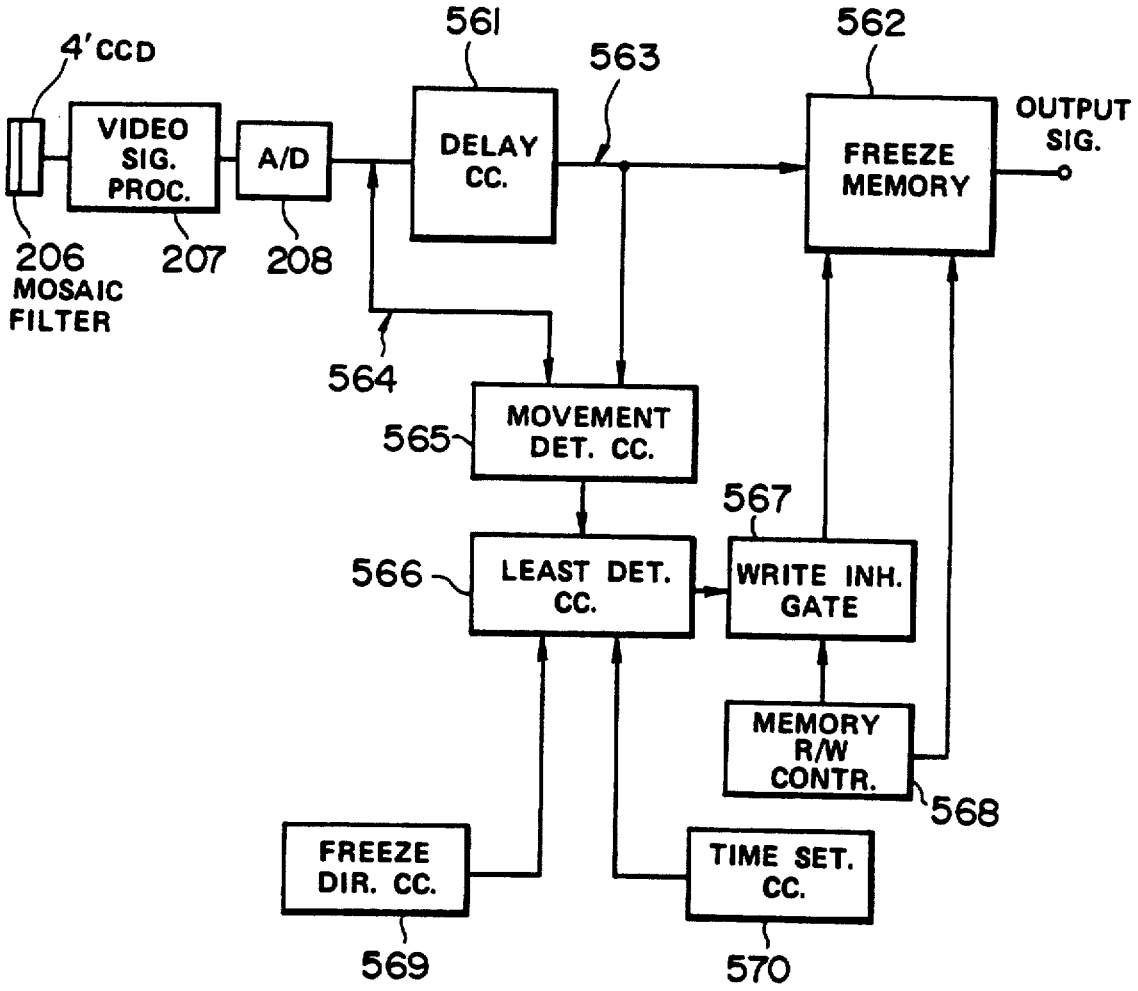
FIG. 58 is a block diagram showing the formation of the 11th embodiment of the present invention.

FIG. 58 shows the formation of an essential part of the 11th embodiment of the present invention.

Whereas FIGS. 52 and 56 show examples of the frame sequential type, this embodiment is an example of the simultaneous type.

For example, the output signal of the CCD 4' of the simultaneous type electronic scope 202 shown in FIG. 25 is converted to a composite video signal by the video signal processing circuit [209] *207*, is then converted to a digital signal by the A/D converter 208 and is transmitted to a delaying circuit 561 and movement detecting circuit 565. The picture image signal 563 delayed by one frame by the above mentioned delaying circuit 561 is transmitted to a freezing memory 562 and the above mentioned movement detecting circuit 565. The above mentioned movement detecting circuit 565 detects the movement amount by the correlation between the picture image signal 564 of the present frame and the picture image signal 563 of the previous frame delayed by one frame. In this movement amount detecting method, the difference between the pixels corresponding to the present frame and the previous frame is determined and the accumulated value of the absolute values of the respective differences is made a movement amount.

The above mentioned freezing memory 562 is controlled in the writing-in and reading-out by a memory R/W controller 568. By the way, the writing-in controlling signal from the memory controller 568 to the above mentioned freezing memory 562 is transmitted to the freezing memory 562 through a writing-in inhibiting gate circuit 567.

The signal processing apparatus of this embodiment comprises a least value detecting circuit 566 detecting the least value of the movement amount within a predetermined time from the output of the above mentioned movement detecting circuit 565, a freezing directing circuit 569 starting this least value detecting circuit 566 and a set time detecting circuit 570 setting the time when the above mentioned least value detecting circuit 566 detects the least value. The above mentioned writing-in inhibiting gate circuit 67 is controlled by the above mentioned least value detecting circuit 566.

When the picture image freezing directing signal is output by the above mentioned freezing directing circuit 569, the movement amounts of the respective picture image signals will be input into the least value detecting circuit 566 which will transmit a control signal to the writing-in inhibiting gate circuit 567 so that the sequentially transmitted picture image signals of small movement amounts may be written into the freezing memory 562.

Thus, according to this embodiment, while the movement amount is calculated and is compared with the least value (by about one frame), the picture image signal will be transmitted to the freezing memory 562 as delayed by one frame by the delaying circuit 561. Therefore, among the picture image signals input until the time set by the set time detecting circuit 570 since the picture image freezing directing signal is output, the picture image signal of the least movement will be written into the freezing memory 562.

Now, such operation as in the following may be made by the formation in FIG. 52.

Even when primary color signals transmitted in time series are written into the synchronizing memory 521 and a picture image freezing directing signal is output from the freezing directing circuit 528, picture image signals will be sequentially read out of the synchronizing memory 521. In case the movement amounts of the respective picture image signals are detected, until the time set by the set time detecting circuit 529 comes since the picture image freezing directing signal is output, the movement amounts of the picture image signals read out of the synchronizing memory 521 will be detected and the sequentially detected movement amounts will be compared by the least value detecting circuit 525 to newly set a value of a small movement amount. In case the detected movement amount is below the set value, a control signal will be transmitted to the memory controller 527 from the least value detecting circuit 525 through the writing-in inhibiting gate circuit 526 to write the picture image signal into the freezing memory 523. On the other hand, in case the detected movement amount is above the set value, a control signal will be transmitted not to write the picture image signal into the freezing memory 523.

Thus, in this embodiment, the movement amounts of all the picture image signals transmitted to the synchronizing memory 521 are detected and the picture image signals are written into the freezing memory 523. The picture image signal written into the freezing memory 523 is a picture image signal immediately after the picture image signal judged to be of the least value of the movement amount.

Figure 59:
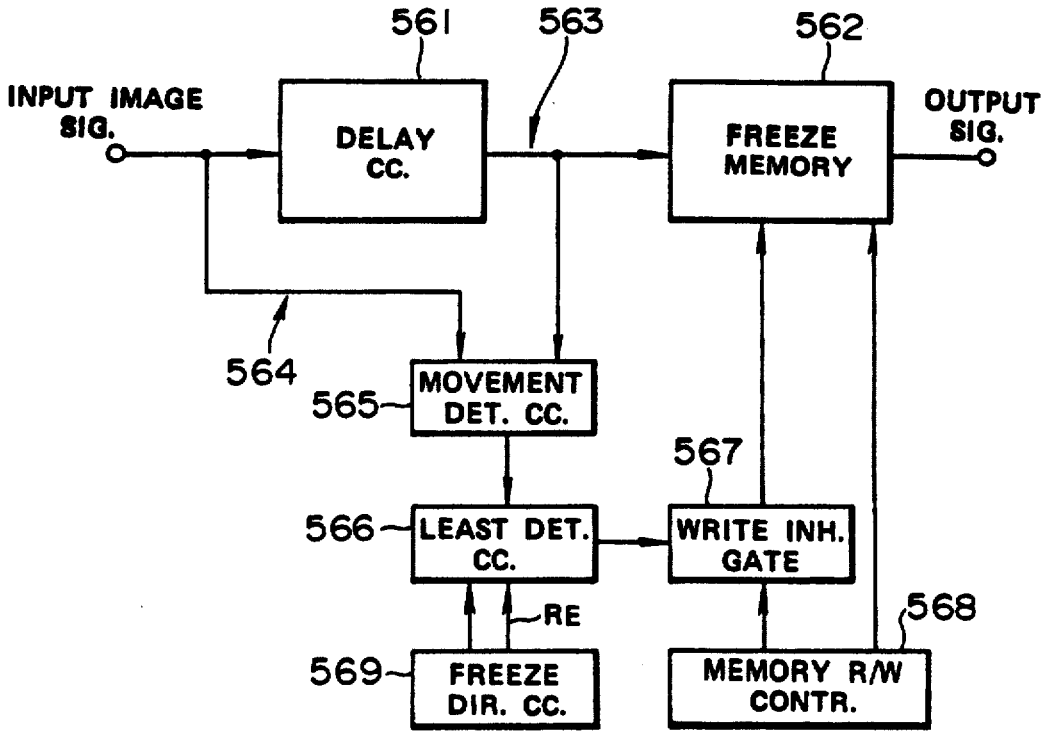
FIG. 59 is a block diagram showing the formation of a modification of the 11th embodiment.

FIG. 59 shows the formation of an essential part of a modification of the 11th embodiment. This embodiment is a formation wherein the set time detecting circuit 570 is not provided in FIG. 58.

Without providing the above mentioned set time detecting circuit, by the freezing directing circuit 569, the least value detecting circuit 566 operates to compare movement detecting signals sequentially input through the movement detecting circuit 565 with the movement amount of the previously input picture image and hold the picture image data of smaller movement amounts in the freezing memory 562.

In other words, *in contrast to the embodiment of FIG. 58* the least value detecting operation time is set to be infinite in the embodiment [in FIG. 58] *of FIG. 59.* the least value detection in this case, the same as in FIGS. 52, 56 and 58, the picture image data of the least movement amount before are held as a frozen picture in the freezing memory 562.

By the way, when the picture image data of the least value are held as a frozen picture in the freezing memory 562, the picture image data will be held forever and therefore the freezing directing circuit 569 will be able to renew the frozen picture to be a moving picture by transmitting a resetting signal RE to the least value detecting circuit 566.

The operation of this modification shall be explained in the following.

Figure 60:
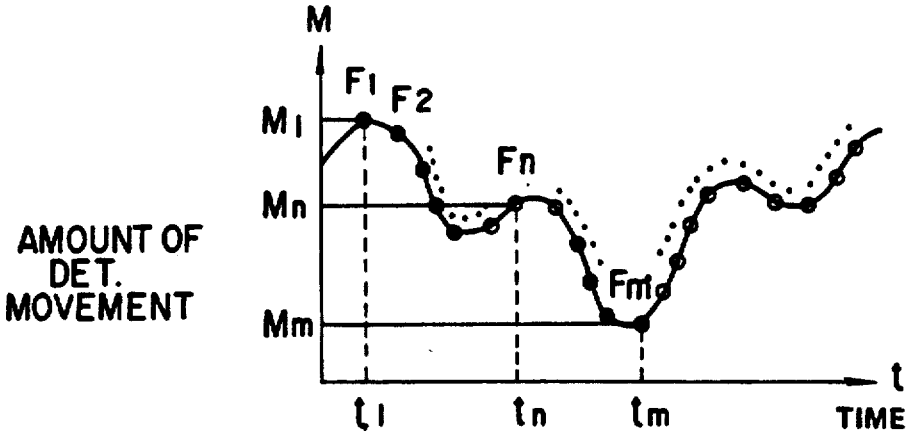
FIG. 60 is an operation explaining view of the modification in FIG. 59.

As shown in FIG. 60, at the time $t_1$, when a picture image freezing directing signal is output from the freezing directing circuit 569, the movement amount $M_1$ detected by the movement detecting circuit 565 will be set as an initial value of the least value detecting circuit 566 and the picture image signal $F_1$ delayed by one frame by the delaying circuit 561 will be written into the freezing memory 562.

Then, the movement amount $M_2$ is detected by the movement detecting circuit 567 into which the picture image signal $F_2$ is input and is compared with the set value $M_1$ by the least value detecting circuit 561 and, since $M_2<M_1$, the writing-in inhibiting gate circuit 567 is controlled so that the picture image signal $F_2$ transmitted to the freezing memory 562 may be written in. Thus, the least value detecting circuit 566 controls the writing-in inhibiting gate circuit 567 so that the sequentially transmitted picture image signals of small movement amounts may be written into the freezing memory 562.

By the way, in FIG. 60, the black circle represents a frozen picture image and the white circle represents a nonfrozen picture image.

Thus, according to this modification, the movement amounts are compared by the least value detecting circuit and the picture image signal of the least movement amount is always written into the freezing memory 562.

Figure 61:
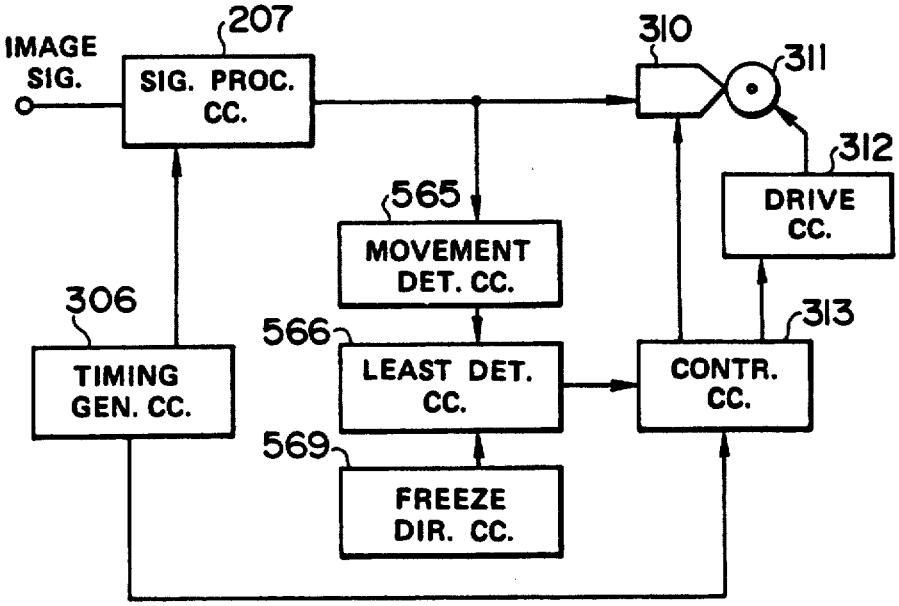
FIG. 61 is a block diagram showing an essential part of the 12th embodiment of the present invention.

FIG. 61 is a block diagram showing the formation of a picture image signal processing apparatus in the 12th embodiment of the present invention.

This embodiment is an example wherein such recording medium as a VTR magnetic tape, magnetic disc or photodisc is used instead of the freezing memory 562 formed of a semiconductor memory or the like.

Such recording medium has been explained in FIG. 33 and shall not be explained here.

By the way, the movement may be detected not only by one frame unit but also by one field unit, one line unit or a unit of a plurality of lines. Also, the movement may be detected in the region of a part of an endoscope picture image.

In the above mentioned 10th to 12th embodiments, in case the time is set, the picture image of the least movement amount will be frozen. However, as explained in the next 13th embodiment, the minimum value may be frozen.

Figure 62:
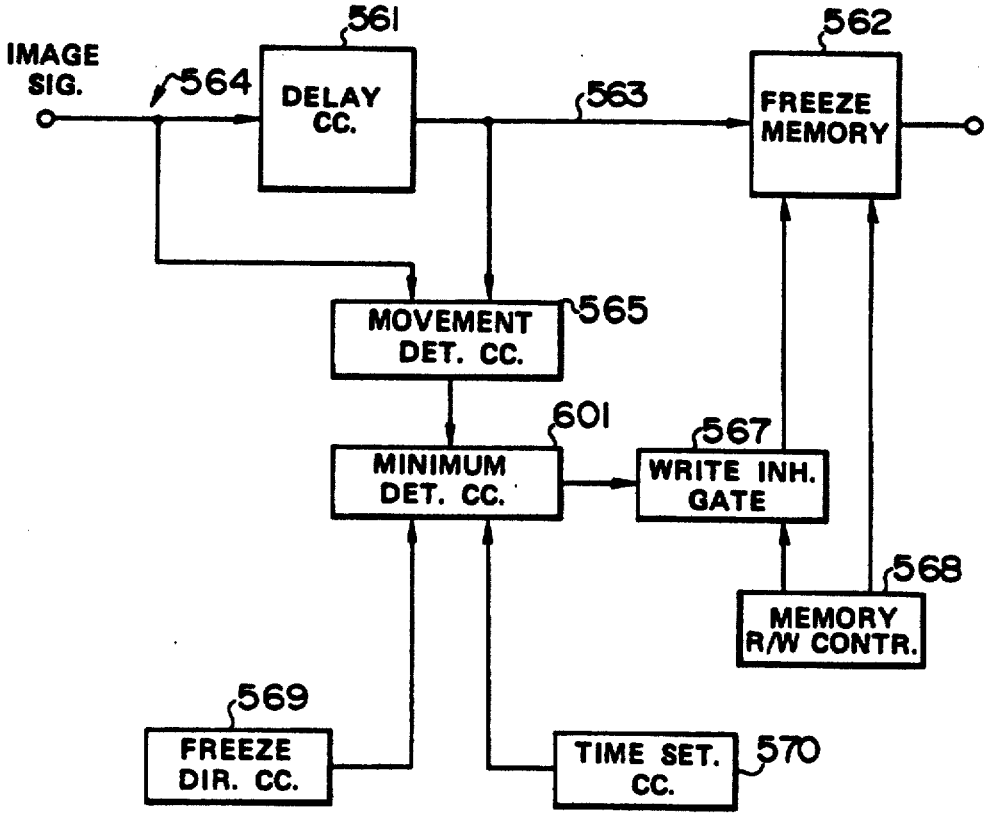
FIG. 62 is a block diagram showing an essential part of the 13th embodiment of the present invention.

FIG. 62 shows an essential part of the 13th embodiment of the present invention.

This embodiment is of a formation wherein a minimum value detecting circuit 601 is used instead of the least value detecting circuit 566, for example, in FIG. 58 and is otherwise of the same formation.

Figure 63A:
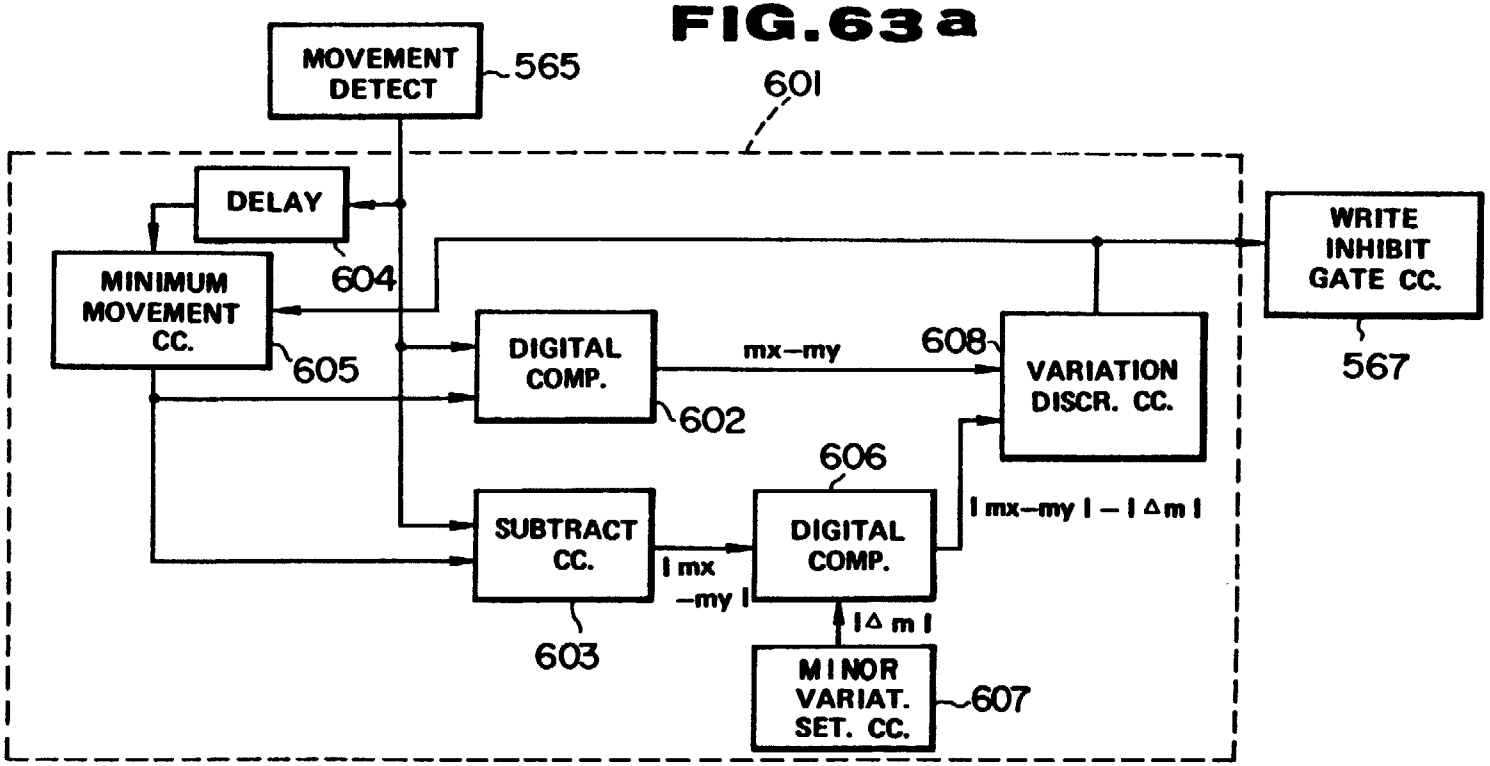
FIGS. 63a and 63b are block diagrams showing the formation of a minimum value detecting circuit in the 13th embodiment.

FIG. 63a shows an example of the above mentioned minimum value detecting circuit 601.

The movement amounts sequentially transmitted from the movement detecting circuit 565 are input into a minimum value memorizing circuit 606 through a first digital comparator 602, subtracting circuit 603 and delaying circuit 604. The movement amount alrelad judged to be of a minimum value is input into the first (digital) comparator 602 and subtracting circuit 603 from the minimum value memorizing circuit 605. In the first comparator 602, the movement amount transmitted from the movement detecting circuit 565 is compared to be larger or smaller than the movement amount of the minimum value transmitted from the minimum value memorizing circuit 605.

In the subtracting circuit 603, the difference between two movement amounts is calculated and its absolute value is transmitted to a second (digital) comparator 606 in which a minor variation $|\Delta m|$ which can be optionally set by a minor variation setting circuit 607 and an absolute value $|mx-my|$ of the difference of the movement amount from the subtracting circuit 603 are compared with each other and the size of the variation of the movement is compared.

The results of the comparison by the first and second comparators 602 and 606 are input into a variation discriminating circuit 608 which will transmit a control signal to the minimum value memorizing circuit 605 and writing-in inhibiting gate circuit 507 only in case the movement amount transmitted from the movement detecting circuit 565 is smaller than the movement amount transmitted from the minimum value memorizing circuit 606 and the absolute value of the difference between these two movement amounts is larger than the minor variation $|\Delta m|$. By this control signal, the minimum value memorizing circuit 605 moves and memorizes as a new minimum value the movement amount transmitted from the detecting circuit 565. By the way, a delaying device 604 is to delay the movement amount input into the minimum value memorizing circuit 605 until a control signal is output from the variation discriminating circuit 608.

When the above mentioned control signal is output, the writing-in inhibiting gate circuit 567 will output a writing-in inhibiting signal to the freezing memory 562 and will hold the picture image data of the minimum value as a frozen picture.

As shown in FIG. 63a, the above mentioned minimum value detecting circuit 601 will output a control signal only in case both of the outputs $mx-my$ and $|mx-my|-|\Delta m|$ are positive (or "1"). That is to say, in the combination of

| | First comparator | |
|---|---|---|
| Second comparator | 1 | 0 |
| | 0 | 0 |

the control signal will be output only in the case of "1" but will not be output in any other case.

The operation of the 13th embodiment using this minimum value detecting circuit 601 shall be explained in the following.

Figure 64:
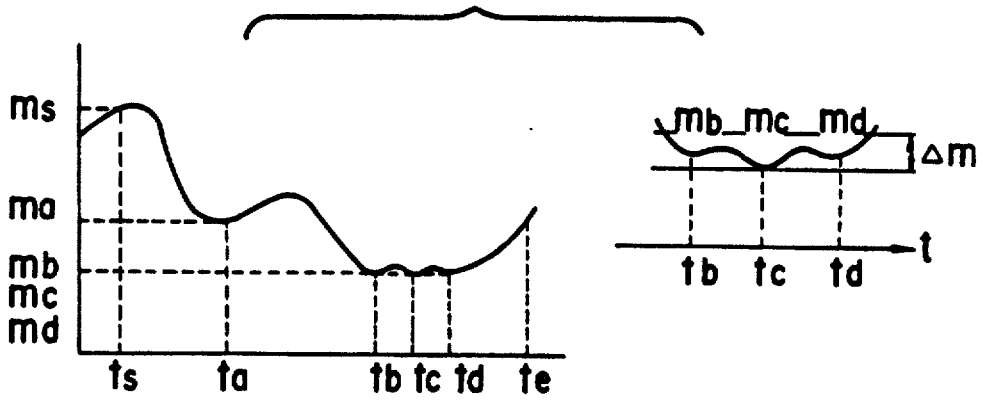

When a picture image freezing directing signal is output at the time $t_s$ as shown in FIG. 64 from the above mentioned freezing directing circuit 569, movement amounts $m_s$, $m_a$, $m_b$, $m_c$, $m_d$ and $m_e$ will be sequentially input by the above mentioned movement detecting circuit 565 into the minimum value detecting circuit 601 in which the sequentially transmitted movement amounts will be compared and at the same time, in case the variation of the movement amount is large, the picture image signal of a small movement amount will be written into the freezing memory 562. For example, in the period from the time $t_s$ to $t_b$, the operation of writing the picture image signal of the small movement amount into the freezing memory 562 will be made.

On the other hand, in case the variation of the movement amount is very small, nothing will be written into the freezing memory 562. For example, in the period from the time $t_b$ to $t_d$, if the picture image signal of the movement amount [$m_b$] $m_b$ is frozen, the movement amounts $m_c$ and $m_d$ of the subsequent picture image signals will be judged to be small in the variation from the movement amount $m_o$ and the writing-in inhibiting gate circuit 567 will be controlled to make no writing into the freezing memory 562.

Thus, in this embodiment, the movement amount is calculated and the picture image signals of small movement amounts among the movement amounts sequentially transmitted within a predetermined time are sequentially written into the freezing memory 562. In such case, the picture image signal judged to be small in the variation of the movement amount will not be written into the freezing memory 562 but the picture image signal of the movement amount of the minimum value will be written into the freezing memory 562.

Figure 63B:
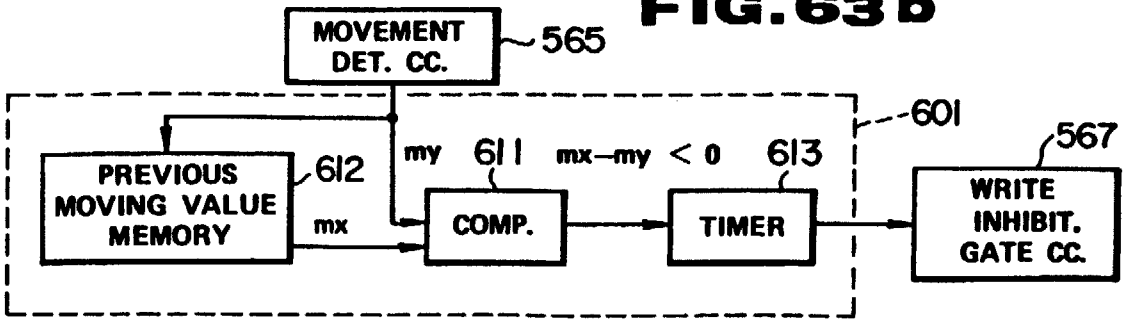

FIG. 63b shows another embodiment of the minimum value detecting circuit.

The output my of the movement detecting circuit 565 is input into a comparator 611 and is compared with the output mx from the previous movement amount memory 612 holding the previous movement amount. When the compared output mx - my is positive, this comparator 611 will start a timer 613 and will output to the writing-in inhibiting circuit 567 a control signal inhibiting the writing-in for a fixed period.

In this embodiment, in case the movement amount of the following picture image signal becomes larger than the movement amount in the preceding picture image signal, a control signal for holding the frozen picture will be output through the timer 613. That is to say, a frozen picture is obtained by the movement amount of the minimum value.

Figure 65:
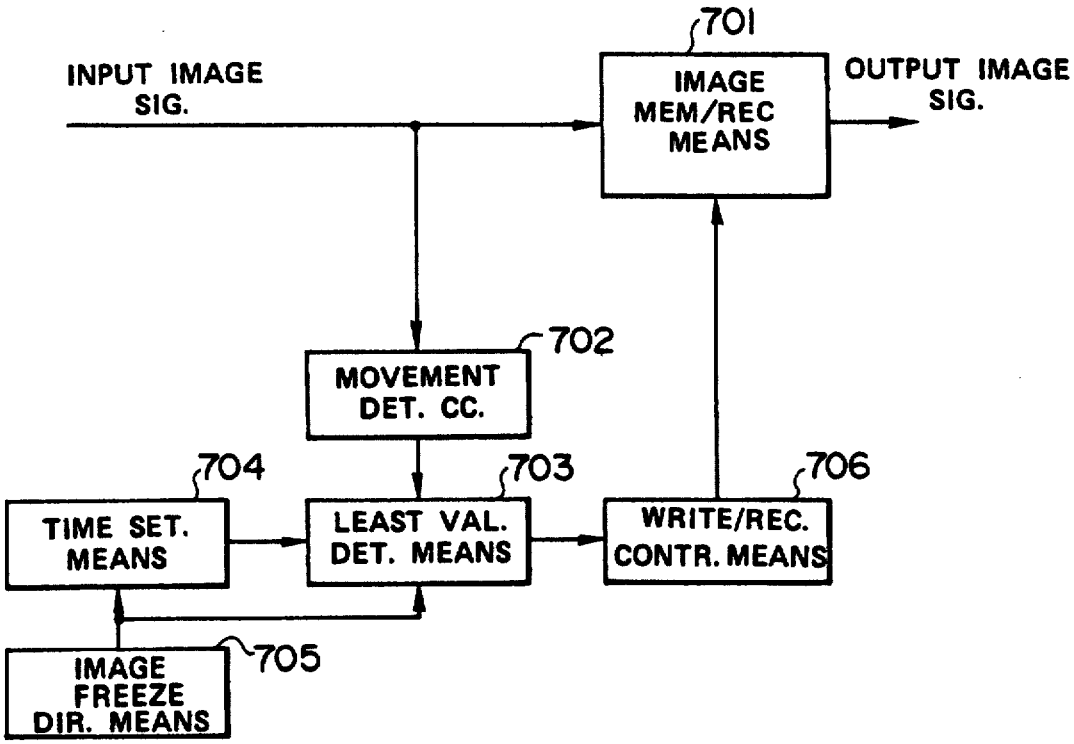
FIG. 65 is a block diagram showing the fundamental formation of an essential part of the 14th embodiment of the present invention.

Now, the fundamental formation of an essential part of the 14th embodiment of the present invention is shown in FIG. 65.

Figure 50:
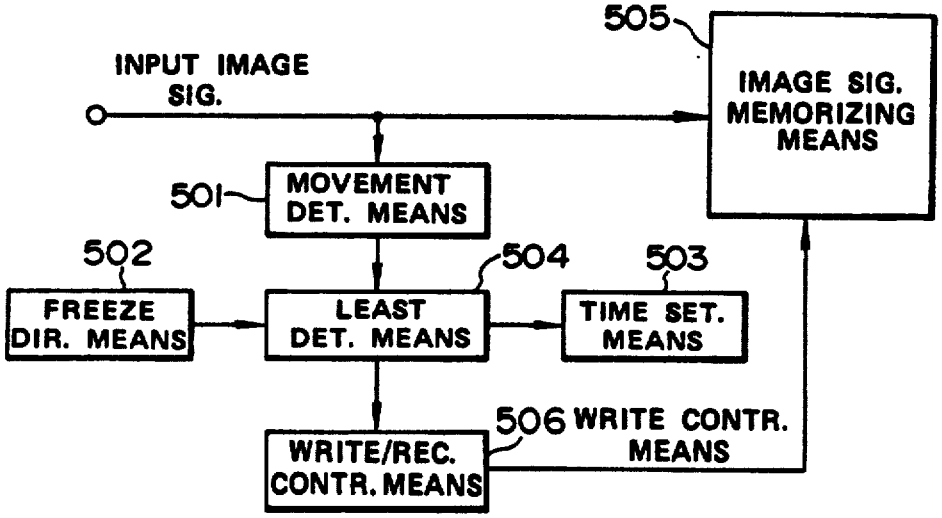
FIG. 50 is a block diagram showing the fundamental formation of an essential part of the tenth embodiment of the present invention.

In this embodiment, in FIG. 50, in the case of detecting the least value by the freezing directing means 502, the least value detecting time is variably controlled to form a picture image freezing signal processing apparatus.

This apparatus comprises a picture image memorizing/recording means 701 memorizing or recording an input picture image signal, a movement detecting means 702 detecting the movement of an object from the above mentioned picture image signal, a least value detecting means 703 detecting the least value of the movement amount of the object from the above mentioned movement detecting means 702, a time setting means [706] *704* optionally setting the operating time of the above mentioned least value detecting means, a picture image freezing directing means 705 directing to freeze a picture image by starting the above mentioned least value detecting means 703 and time setting means 704 and a writing/recording controlling means 706 controlling the above mentioned input picture image signal writing and recording operation for the above mentioned picture image recording/memorizing means 701 on the basis of the least value from the above mentioned least value detecting means 703.

The movement amount of the object is detected from the input picture image signal by the movement detecting means 702 and is transmitted to the least value detecting means 703. The above mentioned least value detecting means 703 and detecting time setting means 704 are started by a directing signal from the picture image freezing directing means 705, a detecting time corresponding to the input picture image signal is set by the above mentioned time setting means 704 and a picture image signal of the least movement amount is detected by the least value detecting means 703 within the range of the set time.

The least value detected by the least value detecting means 703 is applied to the writing/recording controlling means 706 and the writing and recording of the input picture image signal into the memorizing/recording means 701 is controlled by this writing/recording controlling means 706. By the above operation, the detecting time of the least value detecting means 703 is set in response to the input picture image signal and the picture image signal of the least movement amount within the set time is memorized or recorded.

An embodiment of the fundamental formation in FIG. 65 shall be explained in the following.

Figure 66:
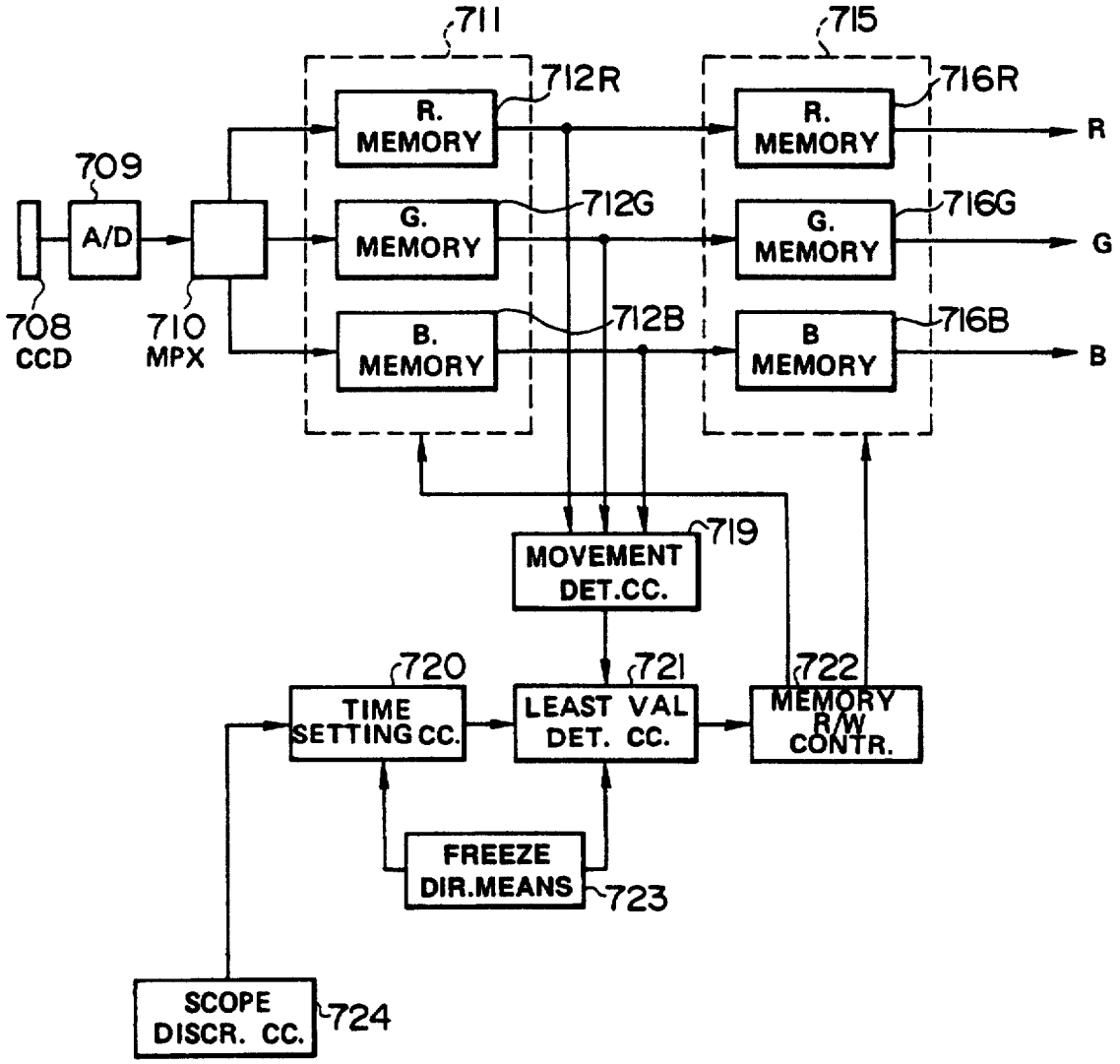
FIG. 66 is a block diagram showing the concrete formation of the 14th embodiment.

FIG. 66 shows the formation of the embodiment of FIG. 65.

The output signal of a CCD 708 is converted to digital data by an A/D converter 709. These digital data are memorized in response to the illuminating lights of the respective colors in an R memory 712R, G memory 712G and B memory 712B within a synchronizing memory part 711 through a multiplexer 710. The picture image signals memorized in the above mentioned R memory 712R, G memory 712G and B memory 712B are read out as synchronized in the respective color signals and are sequentially written as color frame synchronized signals respectively into an R memory 716R, G memory 716G and B memory 716B within a freezing memory 715. The R, G and B picture image signals written into the respective memories within this freezing memory 715 are sequentially read out as synchronized with the synchronized signal of a displaying apparatus or processing apparatus not illustrated connected to the rear step.

The color frame synchronized signals read out of the above mentioned synchronizing memory part 711 are transmitted simultaneously also to the movement detecting circuit 719 and the movement amount of the object is detected by this movement detecting circuit 719 and is transmitted to a least value detecting circuit 721.

Here, when a picture image freezing directing signal is issued by a picture image freezing circuit 723, a time setting circuit 720 and least value detecting circuit 721 will start. A scope discriminating signal corresponding to a scope connected to this apparatus is transmitted from a scope discriminating circuit 724 to this time setting circuit 720. The time for detecting the least value in response to the scope discriminating signal is set in this time setting circuit 720.

The above mentioned least value detecting circuit 721 transmits to a memory R/W controller 722 a detecting signal to detect the least value of the movement amount within the time set by the above mentioned time setting circuit 720 and to read data out of the freezing memory for the picture image signal judged to be of the least movement amount.

The movement detecting circuit 719 in this embodiment can be, for example, the movement detecting circuit 266 shown in FIG. 31.

Figure 67:
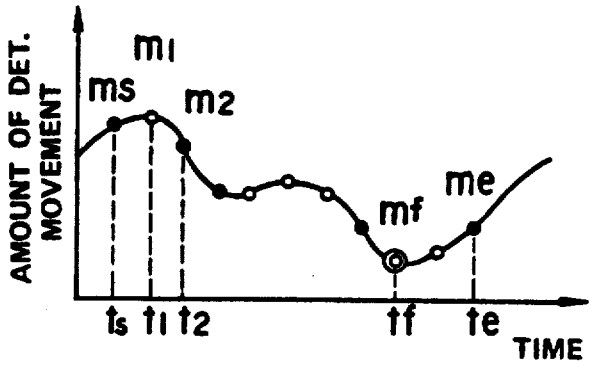
FIG. 67 is an operation explaining view of the 14th embodiment.

The freezing operation of the above mentioned least value detecting circuit 721 is shown in FIG. 67 in which the white circle represents a nonfrozen picture image, the black circle represents a frozen picture image and the double circle represents the [last] *least* frozen picture image. As shown in FIG. 67, the least value detecting circuit 721 transmits to the memory W/R controller 722 a detecting signal to first hold the movement amount $m_s$ at the time $t_s$ and to read the picture image signal out of the freezing memory 715. Then, the movement amount $m_1$ at the time $t_1$ is compared with the above mentioned $m_s$ and the picture image signal of the smaller value is read out. In such case, if $m_s < m_1$, the picture image signal of the movement amount $m_2$ will be read out of the freezing memory 715 and the value of the movement amount $m_2$ will be held.

Such operation as in the above is repeated until the time $t_e$ determined by the detecting time setting circuit 720 and the picture image signal of the least movement amount within the time $t_e - t_s$ is read out of the freezing memory 715.

Figure 68:
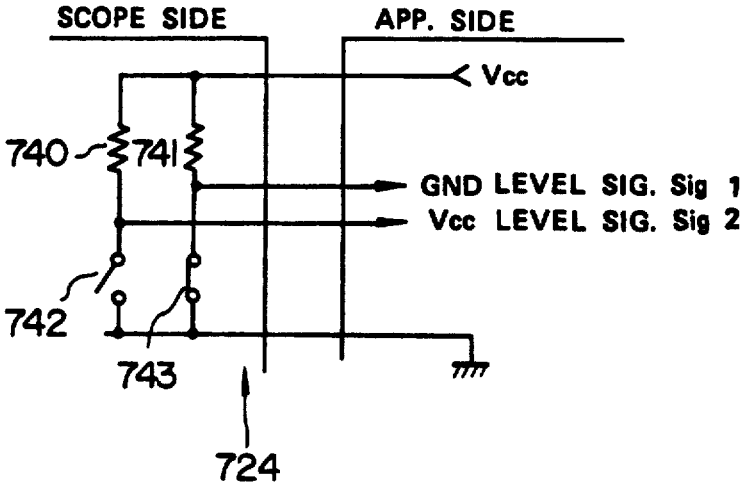
FIG. 68 is a circuit diagram of a scope discriminating circuit in the 14th embodiment.

An example of the scope discriminating circuit in this embodiment is shown in FIG. 68. In this scope discriminating circuit, resistances 740 and 741 provided within the scope are connected each at one end to a reference voltage end $V_{cc}$ of this apparatus and at the other end to a ground terminal GND of this apparatus through switches 742 and 743. The signal of the voltage level of the reference voltage end $V_{cc}$ or ground terminal GND is taken out by switching on and off the above mentioned switch 742 or 743 through a signal line pulled out of between the resistance and switch. Thereby four kinds of scopes can be discriminated and, by increasing the number n of resistances, $2^n$ kinds can be discriminated.

Figure 69:
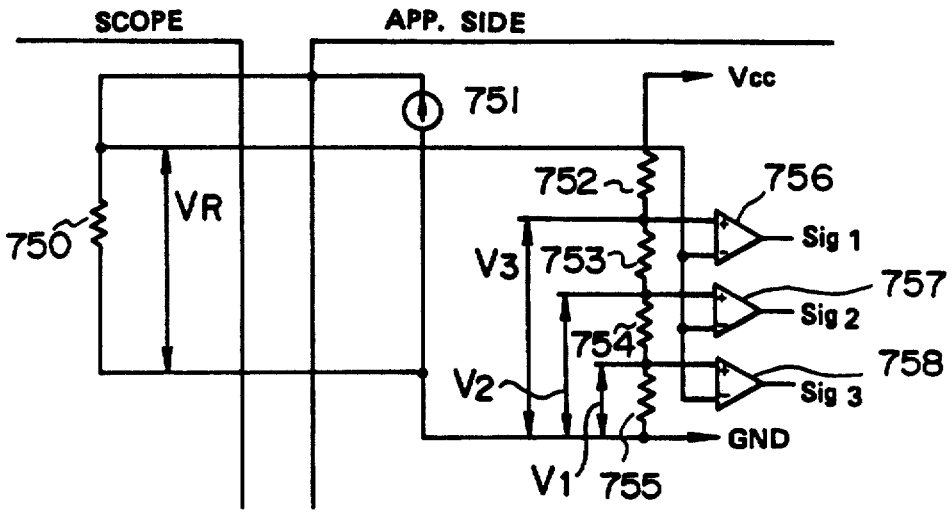
FIG. 69 is a circuit diagram showing another embodiment of the scope discriminating circuit.

Also, by providing a resistance 750 within the scope, the voltage value VR between a constant current power source outside the scope and the resistance is compared with the reference voltage divided by resistances 752, 753, 754 and 755 by comparators 756, 757 and 758 to determine the voltage value VR applied to the resistance 750. When the value of the resistance 750 is varied in response to the scope, the voltage value VR applied to the resistance 750 will vary and therefore the scope will be able to be discriminated. In the example shown in FIG. 69, the following four kinds of scopes can be discriminated:

(1) $VR < V_1$
(2) $V_1 \leqq VR < V_2$
(3) $V_2 \leqq VR < V_3$
(4) $V_3 \leqq VR$ According to this embodiment, the time of detecting the least value can be automatically set in response to the scope to be used.

Generally, in the case of observing the body cavity interior with an endoscope apparatus and recording the frozen picture of the observed picture image with the above mentioned apparatus, the scope now used will be adapted to the part into which the scope is to be inserted. For example, in the case of observing a large intestine, a large diameter scope will be used and in the case of a bronchus, a small diameter one will be used.

The observed picture image does not substantially move as in the large intestine, moves slowly forward and rearward at each breathing as in the bronchus (when observed with a straight viewing type endoscope) or moves quickly as in the stomach due to the movement (contracting motion) or in the esophagus due to the breathing or pulsation. The same observed part is different in the movement amount due to the difference between the picture angles of the respective endoscopes. Therefore, if the least value detecting time is fixed to be constant, the detecting time will be short for the fast moving picture image and will be excessive for the [not substantially moving] *substantially non-moving* picture image and the next operation will not be made until the set time ends to disadvantage.

On the other hand, in this embodiment, the time can be automatically set in response to the scope and therefore a frozen picture image having little fogging can be obtained within the set time adapted to the part to be used.

Figure 70:
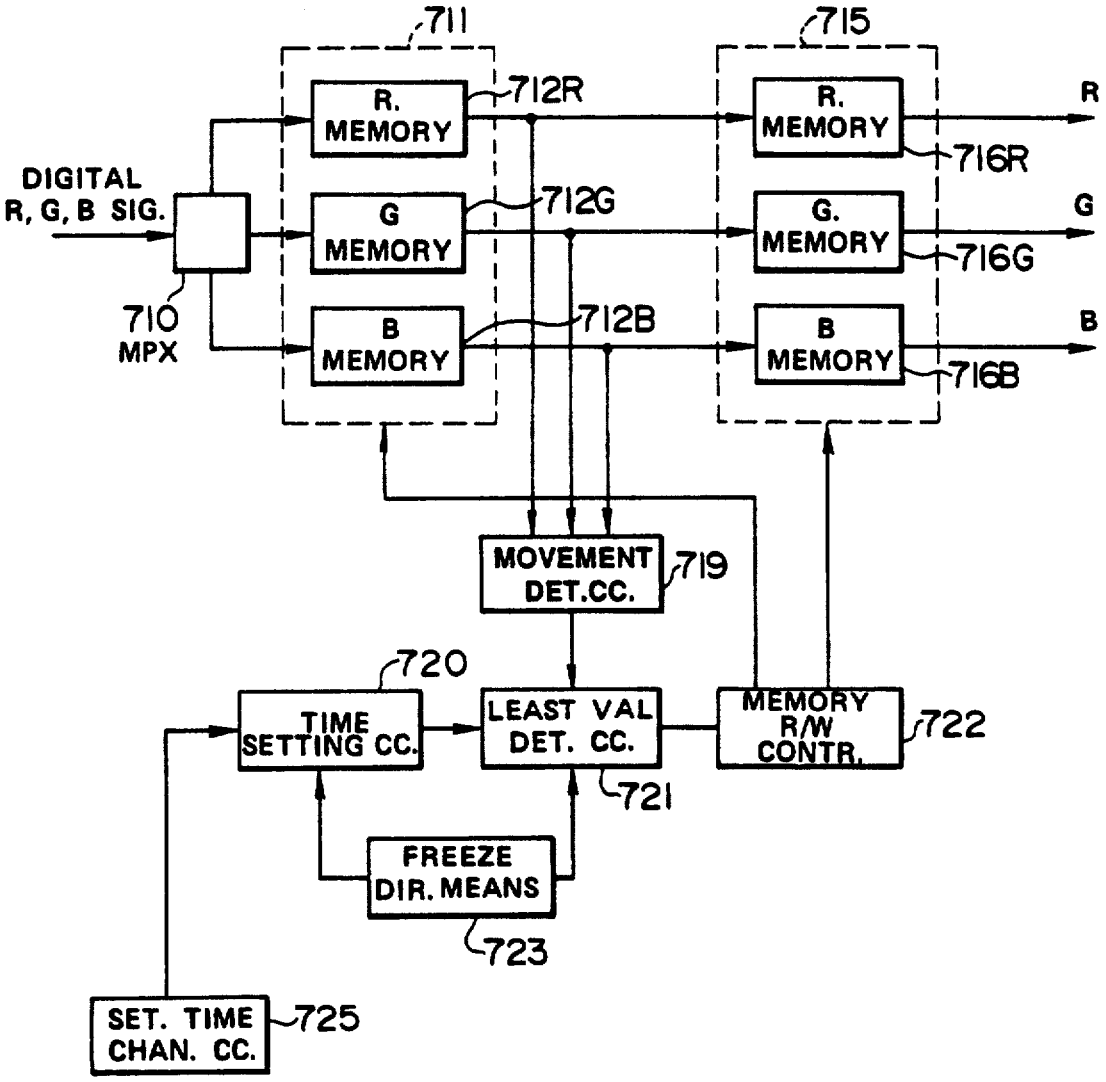
FIG. 70 is a block diagram of an essential part of a modification of the 14th embodiment of the present invention.

FIG. 70 shows a modification of the 14th embodiment.

In this modification, the time to sense the connected scope to determine the least value of the movement amount is set by a switching switch provided outside the scope in the 14th embodiment shown in FIG. 66.

Therefore, a set time switching circuit 725 is provided instead of the scope discriminating circuit 724 of the above mentioned 14th embodiment.

Figure 71:
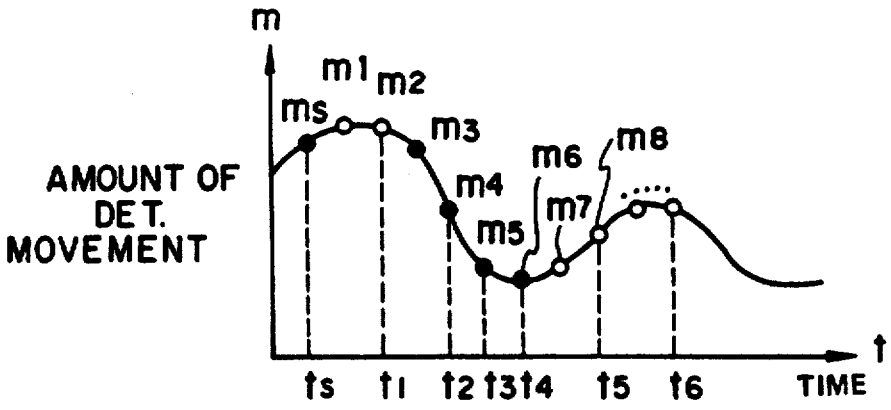
FIG. 71 is an operation explaining view of this modification.

An example of setting the time by this set time changing circuit 725 is shown in FIG. 71. Here, $t_s$ represents the time when the freezing switch is pushed to start of the operation of the least value detecting circuit 721. In this example, the time when the detecting operation of the least value detecting circuit ends can be optionally set within the range of $t_l$ to $t_n$ by the switching switch. The least value of the movement amount at respective times is:

$t_1 \rightarrow m_s$ $t_2 \rightarrow m_4$ $t_3 \rightarrow m_5$ $t_4 \rightarrow m_6$. . . The set time is switched in response to the movement amount of the object and the picture image signal of the least movement amount can be read out of the freezing memory 715 and displayed by a monitor 796.

Figure 72:
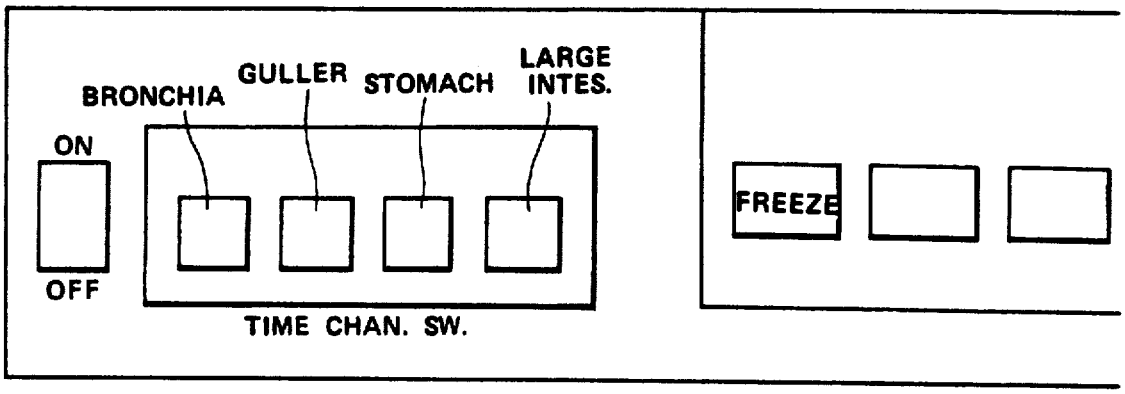
FIG. 72 is a view showing a switch for setting time in this modification.
Figure 74:
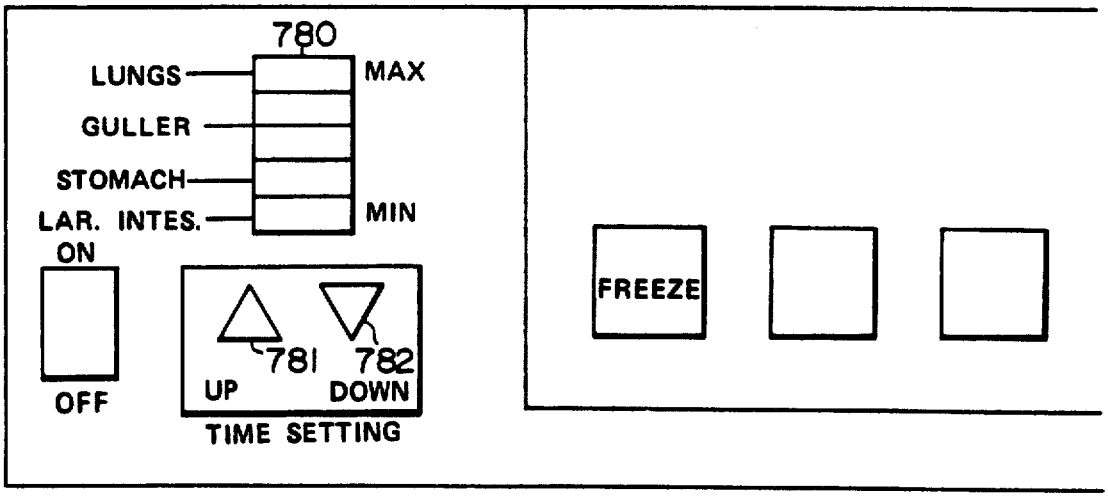
FIG. 74 is a view showing a time setting means in the 15th embodiment.

For example, the above mentioned switching switch can be provided on the panel of the apparatus as shown in FIG. 72 so that the respective switches may be switched depending on the part to be observed to set the detecting time of the least value.

The other formation, operation and effect of this modification are the same as of the above mentioned 14th embodiment.

Figure 73:
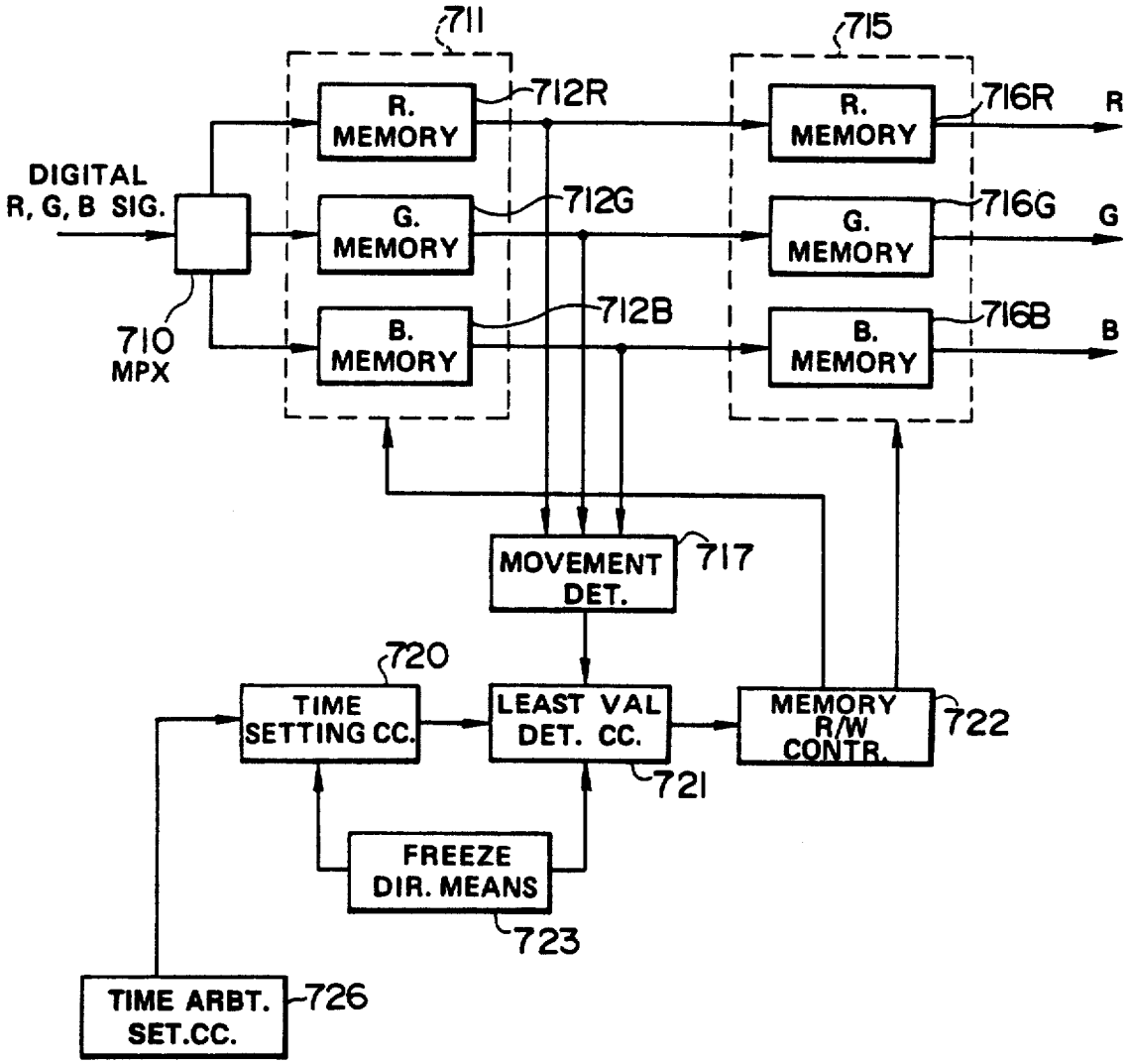
FIG. 73 is a block diagram showing an essential part of the 15th embodiment of the present invention.

FIG. 73 shows the 15th embodiment of the present invention. In this 15th embodiment, the detecting time for determining the least value set in response to the scope to be connected to this apparatus in the above mentioned 14th embodiment can be optionally set [from outside] *externally* outside and therefore a time optionally setting circuit 726 is provided instead of the scope discriminating circuit 724 of the above mentioned 14th embodiment.

The setting signal to this time optionally setting circuit 726 is made by switches 781 and 782 provided on the panel of this apparatus as shown, for example, in FIG. 71 so that the observer may optionally set the detecting time of the least value and the set time may be displayed in a graph displaying part 780 by an LED or the like.

The other formation, operation and effect of this 15th embodiment are the same as of the above mentioned 14th embodiment.

Figure 75:
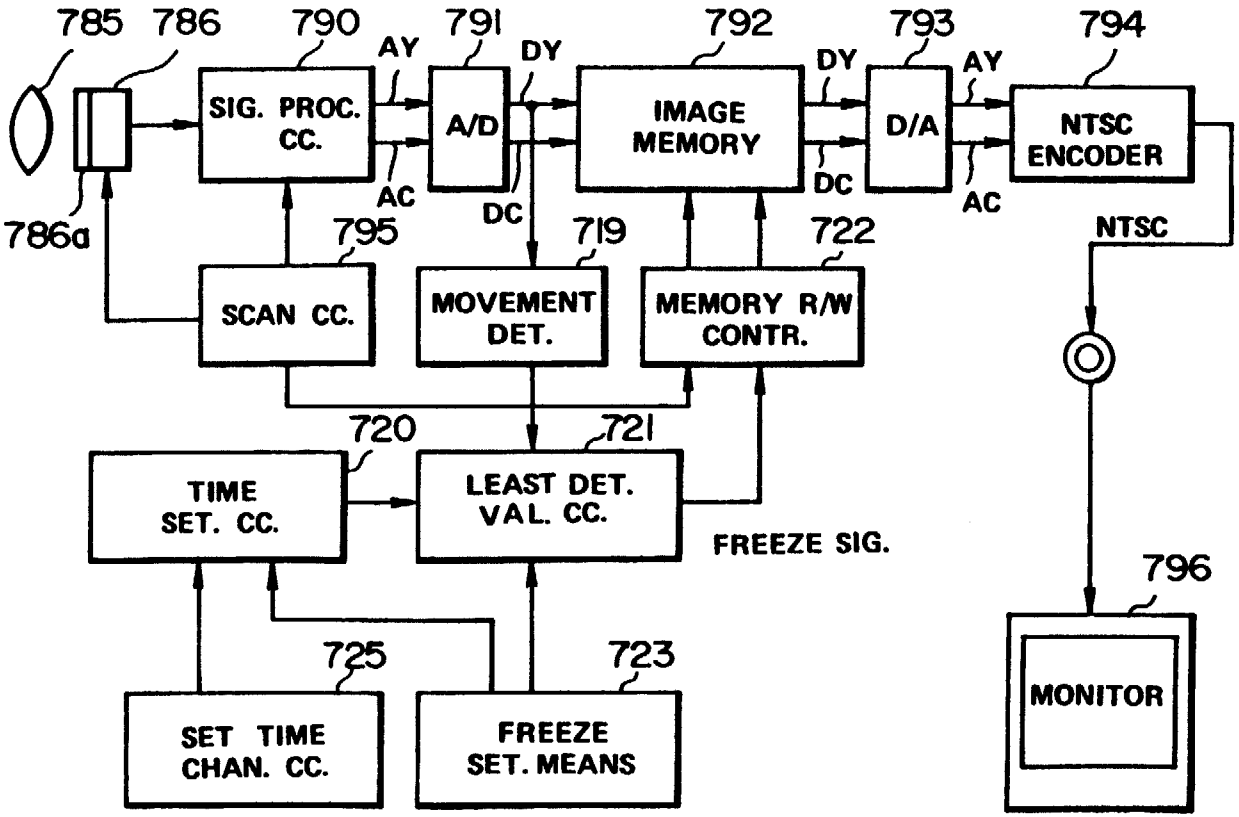
FIG. 75 is a block diagram of the 16th embodiment of the present invention.

FIG. 75 shows the 16th embodiment of the present invention. The above mentioned 14th and 15th embodiments are applied to an imaging apparatus of an R, G and B frame sequential system. This 16th embodiment is applied to an apparatus of a color simultaneous imaging system using a mosaic filter type device as an imaging device.

In this 16th embodiment, an object is imaged by an imaging optical system 785 and the object image is formed on the imaging surface of an imaging device 786. A color separating mosaic filter 786a is fitted to the front surface of the imaging surface of this imaging device 786.

The optical image of the object formed on the above mentioned imaging surface is photoelectrically converted, is processed to be a signal by a signal processing circuit 790 under the control of a scanning circuit 795, is input into an A/D converter 791 as an analogue luminance signal Ay and an analogue color line sequential signal AC, is converted to a digital signal by this A/D converter 791 and is written into a picture image memory 792. The signal read out of this picture image memory 792 is converted to an analogue signal by a D/A converter 793, is then converted to an NTSC signal by an NTSC encoder 794 and is displayed in an external monitor 796. The formation of the other [part is] *parts of this embodiment are* is the same as in the above mentioned FIG. 70 and the same reference numerals are attached to the same devices. In this embodiment, in the above mentioned formation, a movement amount is detected from a luminance digital signal DY and the freezing is controlled on the basis of the detected amount in consideration of the visibility of the human eye. In case the movement is desired to be detected by noting particularly the color of the object, the movement may be detected by using a digital color signal DC.

The movement amount detected by the movement detecting circuit 719 has the least value of the movement amount within the set time detected by the least value detecting circuit 721 and the picture image signal judged to be of the least value is displayed in the monitor 796.

By the way, the least value detecting time can be set by the system shown in the above mentioned 14th and 15th embodiments.

The other formation, operation and effect of this 16th embodiment are the same as of the modification of the above mentioned 13th embodiment.

Figure 76:
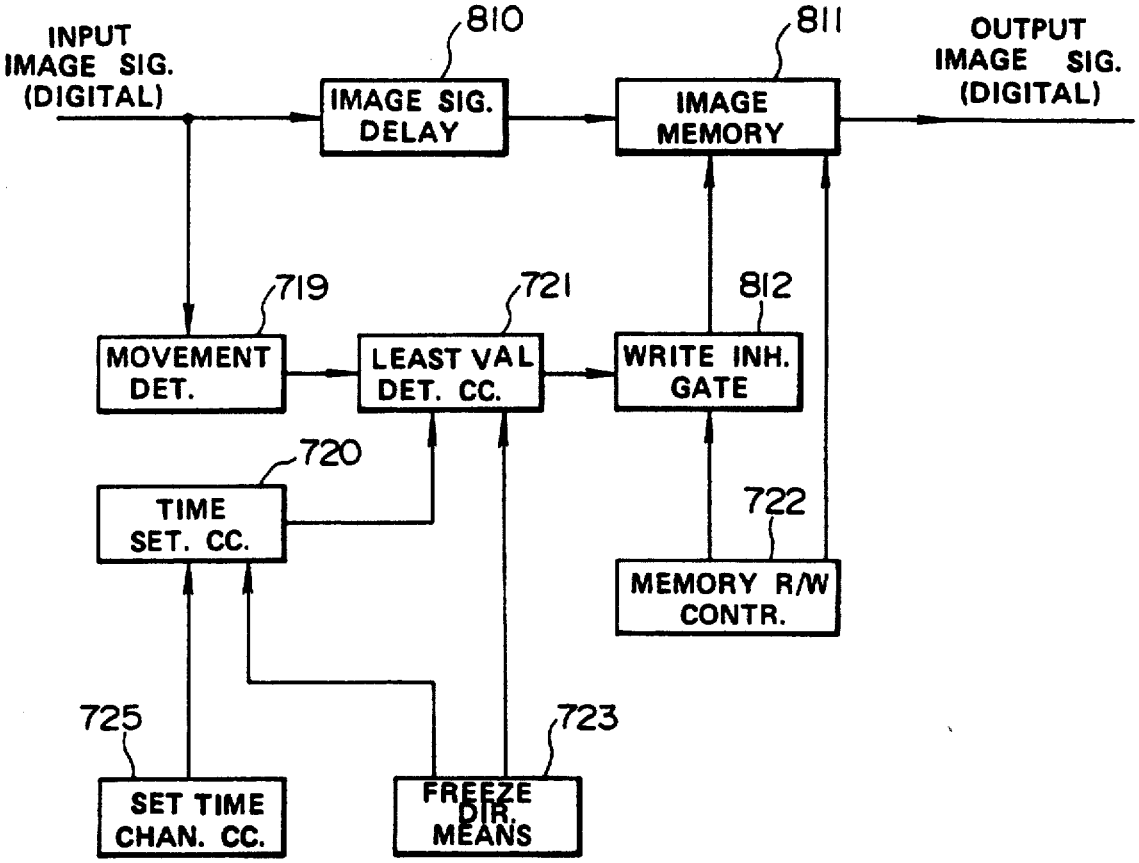
FIG. 76 is a block diagram of the 17th embodiment of the present invention.

FIG. 76 shows the 17th embodiment of the present invention. In the case of detecting the movement amount from sequentially input picture image signals and controlling the freezing on the basis of the value, in case a delaying means is included in the movement detecting means, if the picture images are continuously input, when the movement amount is detected and whether the freezing is possible or not is judged, a new picture image input will already begin and the picture image at the next time of the picture image having had the movement detected will be thought to be frozen. If the movement of the object is not so quick, the object of the present invention will be able to be well attained with the above mentioned formation but, in case the movement is fast, though the movement detecting circuit is correctly operating, an image having an image fogging or color smear will be frozen to disadvantage.

This 17th embodiment is an example in which such disadvantage as in the above is eliminated, a picture image signal delaying means 810 is added to the input step of a picture image memory 811 and the delay amount of the movement detecting means 719 is corrected by this picture image signal delaying means 810 so that the picture image judged to be of the movement amount of the object below a predetermined value and the picture image to be frozen may coincide with each other.

The least value of the movement amount within the set time is detected by the least value detecting circuit 721 from the movement amount detected by the movement detecting circuit 719 and the picture image signal judged to be of the least value is displayed in a monitor not illustrated. At this time, the operation of writing-in from the memory R/W controller 722 will be controlled on the basis of the output from the above mentioned least value detecting circuit 721 in a writing-in inhibiting gate 812.

By the way, the detecting time can be set by using the system shown in the above mentioned 14th and 15th embodiments.

The other formation, operation and effect of this 17th embodiment are the same as of the above mentioned modification in FIG. 70.

Figure 77:
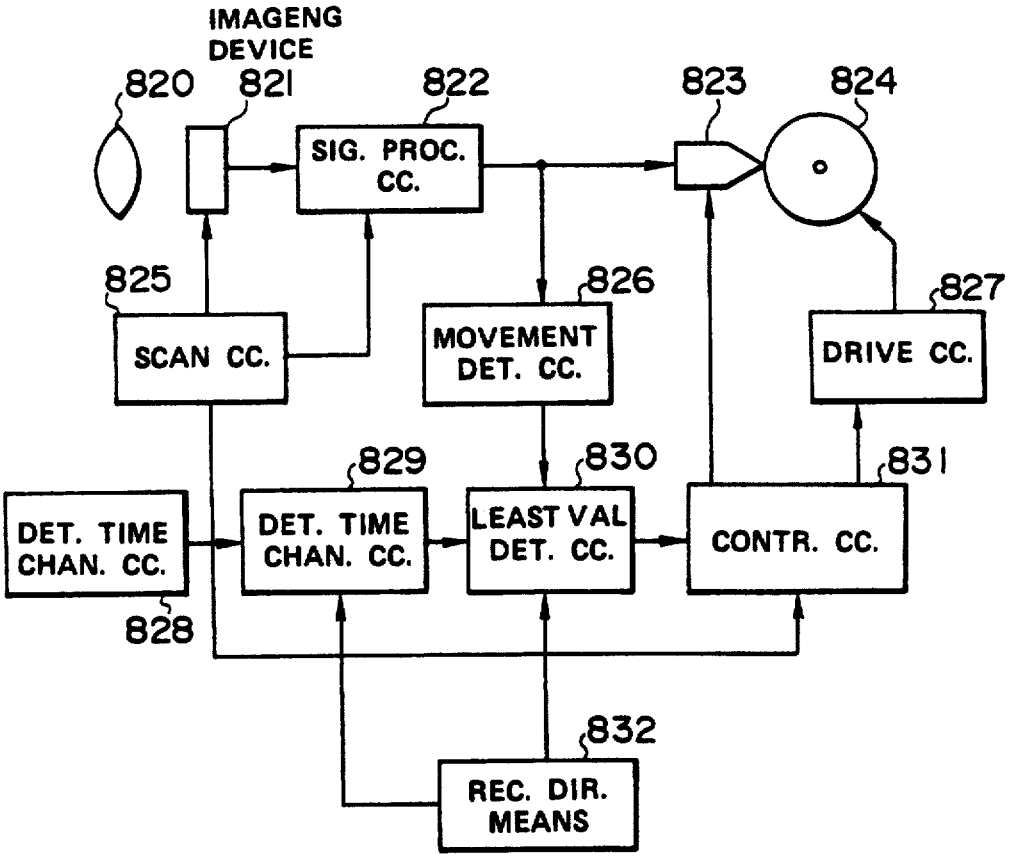
FIG. 77 is a block diagram of the 18th embodiment of the present invention.

FIG. 77 shows the 18th embodiment of the present invention. In this 18th embodiment, the present invention is applied to an apparatus whereby an object is imaged and its frozen picture image is recorded in a recording medium. This embodiment shall be briefly explained in the following. The optical image of the object imaged by an imaging optical system 820 and formed on the imaging surface of an imaging device 821 is photoelectrically converted by this imaging device 821, is scanned under the control of a scanning circuit 825, is input as a picture image signal into a signal processing circuit 822, is variously processed and is transmitted to a [header] *recording head* 823 of a recording medium. At the same time, this signal is transmitted also to a movement detecting circuit 826 and the movement amount of the object is detected. Now, when a recording directing signal is issued from a recording directing means 832 (corresponding to the picture image freezing directing means in the above mentioned respective embodiments), a detecting time setting circuit 829 and least value detecting circuit 830 will start and a control signal will be transmitted to the detecting time setting circuit 829 so that a detecting time corresponding to the object may be set by a detecting time switching circuit 828. Within the time set by this detecting time setting circuit 829, the least value of the movement amount of the input picture image signal is determined by the least value detecting circuit 830. The picture image at this time is recorded in a recording medium 824 under the control of the [header] *recording head* 823 and a driving circuit 827 by a control circuit 831.

By the way, the above mentioned recording medium 824 may be a magnetic tape, magnetic disc, photodisc or still video floppy disc.

The other formation, operation and effect of the 18th embodiment are the same as of the above mentioned modification in FIG. 70.

Figure 78:
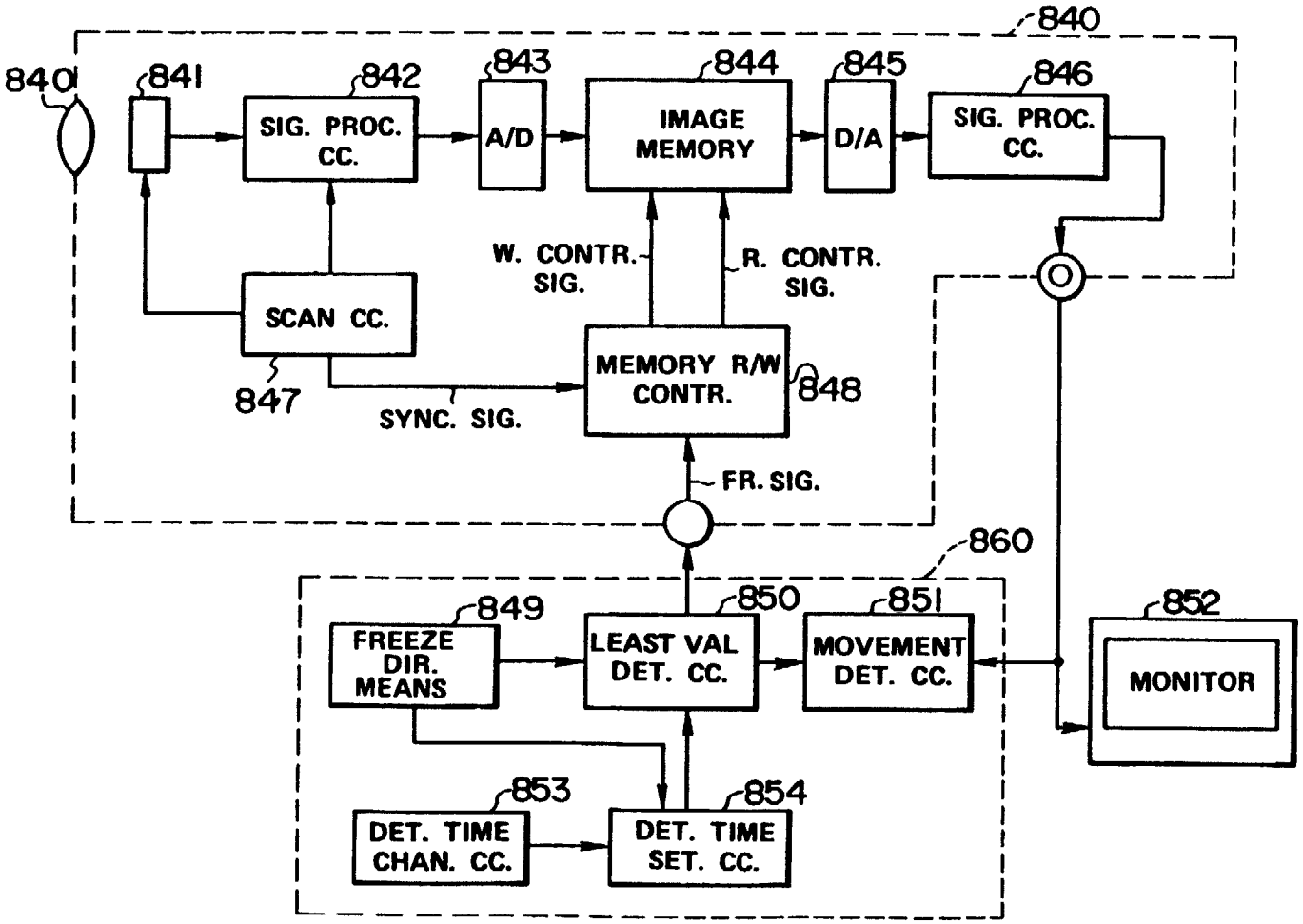
FIG. 78 is a block diagram of the 19th embodiment of the present invention.

FIG. 78 is a block diagram showing the formation of a picture image freezing signal processing apparatus in the 19th embodiment of the present invention. In this embodiment, a part of the picture image freezing signal processing apparatus is formed outside the [body] *main* apparatus as an attached apparatus. As shown in FIG. 78, the picture image freezing apparatus of this embodiment comprises a [body] *main* apparatus 840 and an attached apparatus 860 provided outside this [body] *main* apparatus 840.

The above mentioned [body] *main* apparatus 840 is formed as follows. That is to say, an optical image of an object formed on the imaging surface of an imaging device 841 by an imaging optical system 840 is photoelectrically converted by the above mentioned imaging device 841 and is input as a picture image signal into a signal processing circuit 842 under the control of a scanning circuit 847. The picture image signal is variously processed by this signal processing circuit 842, is then A/D-converted by an A/D converter 843 and is written into a picture memory 844. The picture image signal read out of the above mentioned picture image memory 844 is D/A-converted by a D/A converter 845 and is then processed by a signal processing circuit 846 and the picture image is displayed in a monitor 845. By the way, the above mentioned picture image memory 844 is controlled in the writing-in and reading-out by a memory R/W controller 848 provided within the body apparatus 840. A synchronized signal from the above mentioned scanning circuit 847 is input into this memory R/W controller 848 which is thus synchronized with the imaging device 841 and signal processing circuit 846.

On the other hand, the above mentioned attached apparatus 860 comprises a movement detecting means 851 detecting the movement of the object from the picture image signal output from the above mentioned signal processing circuit 846, a least value detecting circuit 850 detecting the least value of the movement amount detected by this movement detecting means, a detecting time setting circuit setting the detecting time of this least value detecting circuit 850, a freezing directing means 849 starting the above mentioned least value detecting circuit 850 and time setting circuit 854 and a detecting time switching circuit 853 switching the detecting time of the above mentioned time setting circuit 854. The least value of the movement amount detected by the above mentioned least value detecting circuit 850 is transmitted to the memory R/W controller 848 within the above mentioned body apparatus.

In this 19th embodiment, when a freezing directing signal is issued by the freezing directing means 849, a picture image signal of the least movement within the time set in response to the object will be detected on the basis of the movement amount of the object detected by the movement detecting means 851 from the output picture image signal of the [body] *main* apparatus and a discriminating signal will be transmitted to the memory R/W controller 848 to control the freezing.

The other formation, operation and effect of this 19th embodiment are the same as in FIG. 70.

Figure 79:
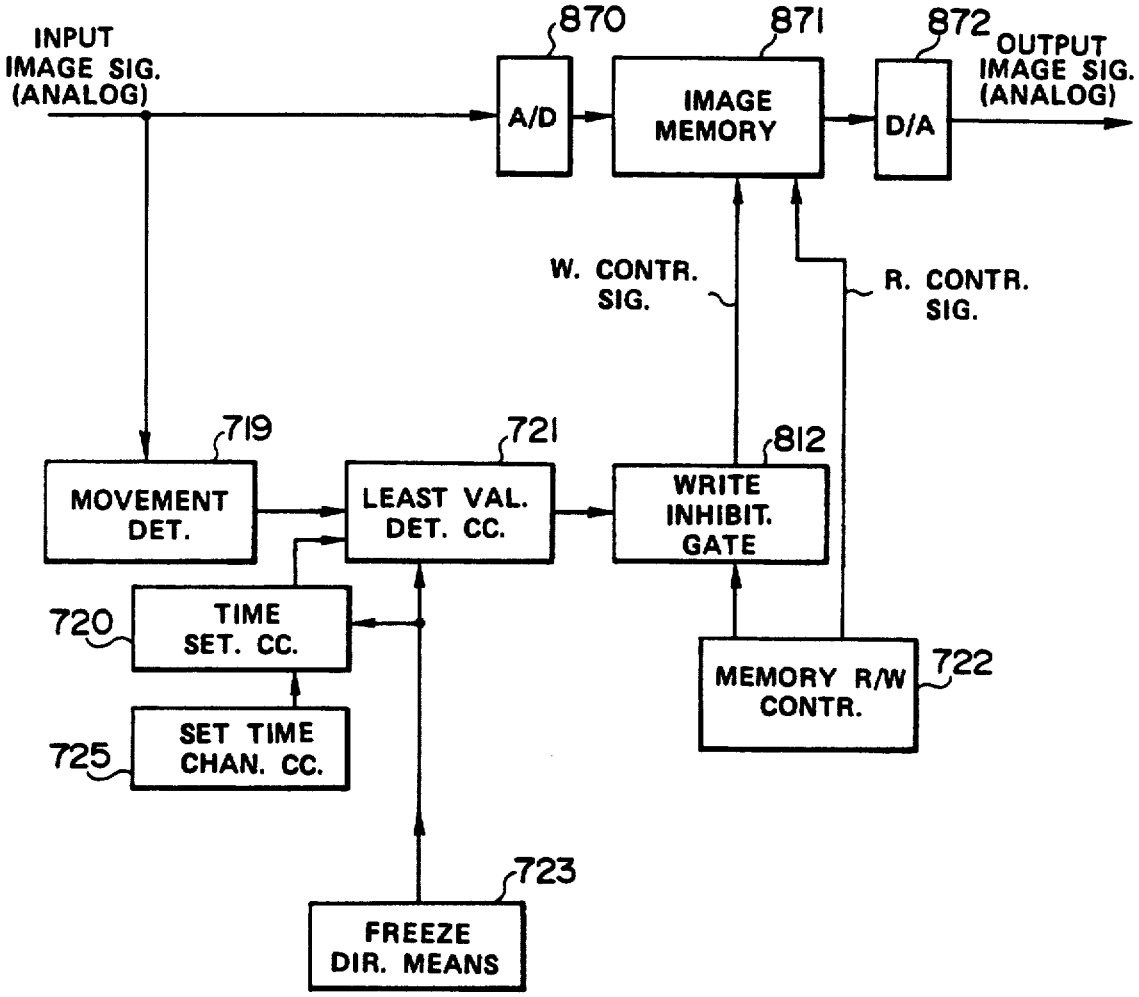
FIG. 79 is a block diagram of the 20th embodiment of the present invention.

FIG. 79 shows the 20th embodiment of the present invention. In this embodiment, the input picture image signal to the movement detecting means is an analogue type picture image signal and accordingly the movement detecting circuit is formed as described below but is otherwise the same as in FIG. 70.

In this 20th embodiment, as shown in FIG. 79, an analogue input picture image signal is digital-converted by an A/D converter 870, is input into a picture image memory 871, is read out of this picture image memory 871, is then again analogue-converted by a D/A converter 872 and is output as an analogue type picture image signal. The above mentioned analogue type input picture image signal is input also into a movement detecting circuit [873] *719* to detect the movement of the object. The subsequent signal processing is the same as in FIG. 76.

The other formation, operation and effect of this 20th embodiment are the same as in FIG. 70.

Figure 80:
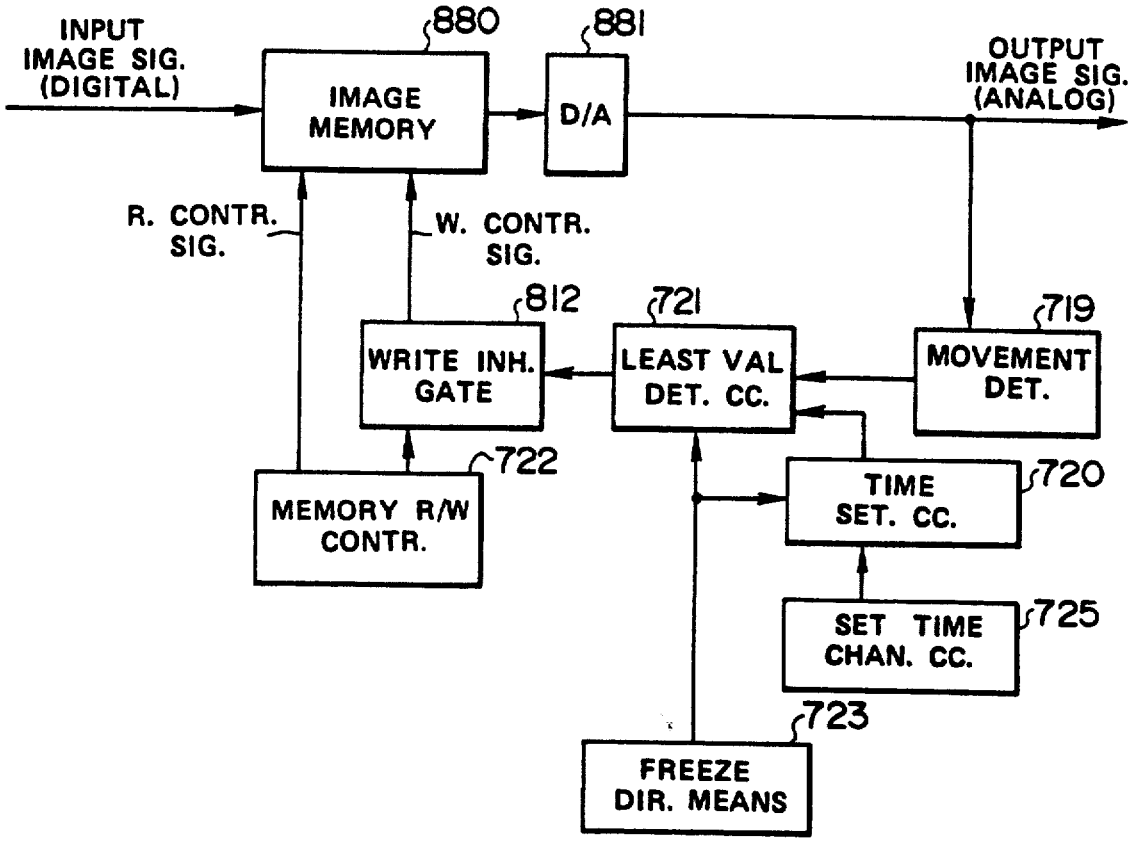
FIG. 80 is a block diagram of the 21st embodiment of the present invention.

FIG. 80 is a block diagram showing the formation of a picture image freezing signal processing apparatus of the 21st embodiment of the present invention.

In this 21st embodiment, a picture image signal input into the movement detecting means 719 is analogue-converted to be an analogue type signal through a D/A converter 881 from a picture image memory 880.

The other formation, operation and effect of this 21st embodiment are the same as in FIG. 76.

Figure 81:
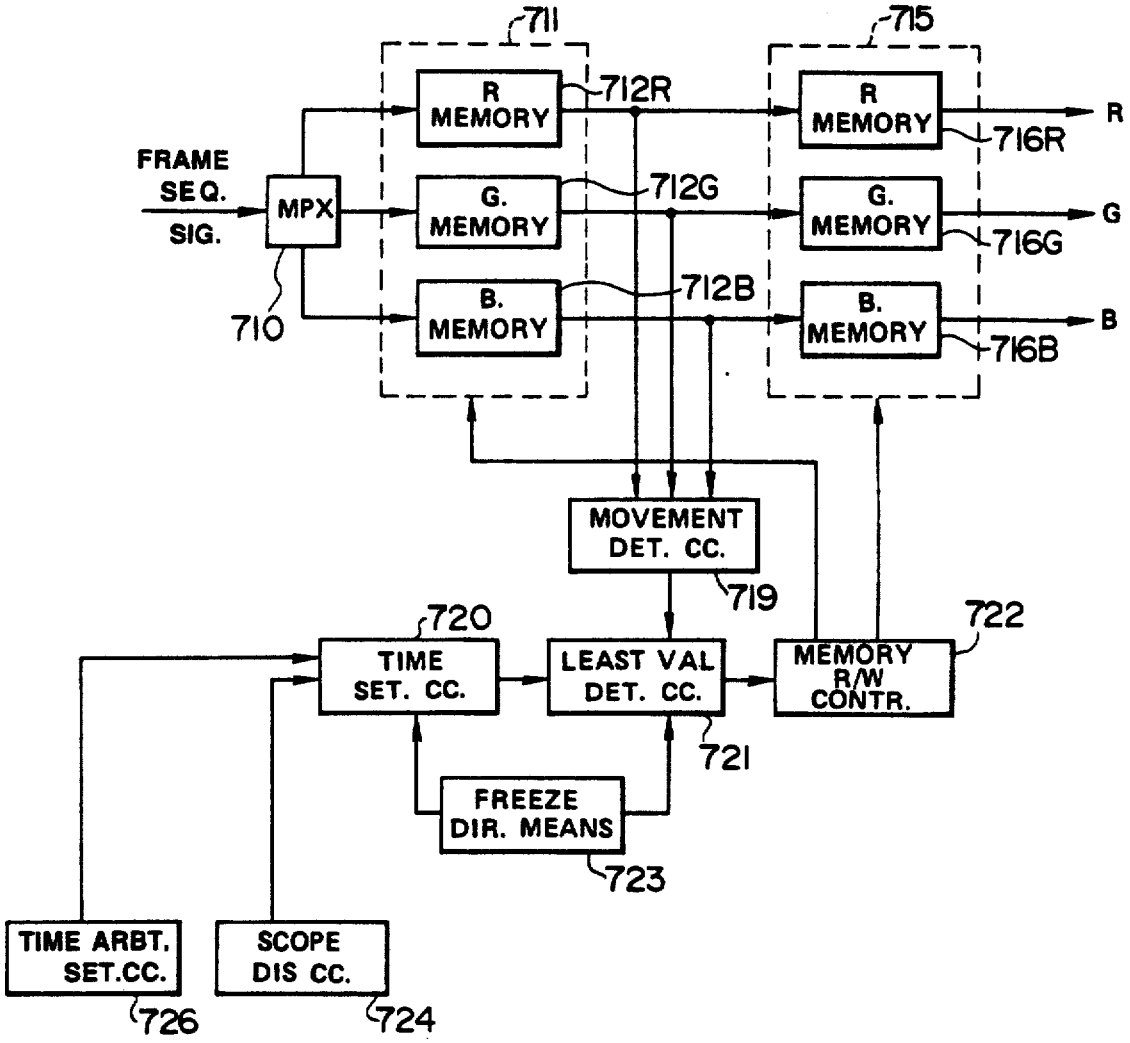
FIG. 81 is a block diagram of the 22nd embodiment of the present invention.
Figure 82:
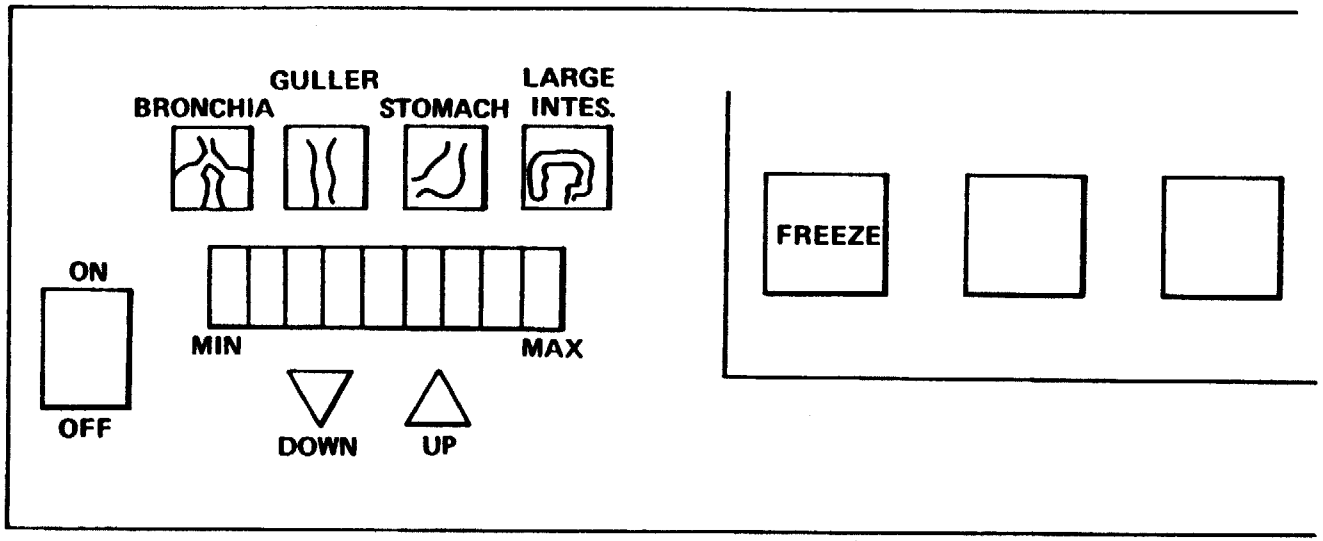
FIG. 82 is a view showing a displaying panel in the 22nd embodiment.

FIG. 81 shows the 22nd embodiment of the present invention. In this 22nd embodiment, the least value detecting time setting methods of the above mentioned 14th and 15th embodiments can be used together and the detecting time set in response to the scope discriminating signal from the scope discriminating circuit 724 in the above mentioned 14th embodiment can be set by a detecting time optionally setting circuit 726. The other parts of this 22nd embodiment are the same as in the above mentioned embodiment.

In FIG. 81, in the movement detecting circuit 719, the movement amount of the object is detected from an input picture image signal and is transmitted to the least value detecting circuit 721. Now, when a freezing signal is transmitted out of the picture image freezing circuit 723, the time setting circuit 720 and least value detecting circuit 721 will start and, in the time setting circuit 720, the endoscope to be connected to this apparatus will be discriminated by the scope discriminating circuit 724 and, when the discriminating signal is fed to this time sitting circuit 720, the least value detecting time corresponding to each endoscope will be set. At this time, in case the same object is observed with an endoscope different in the picture angle, the movement amount of the input picture image will be different (when the picture angle expands, the movement amount will become smaller). Therefore, the time optionally setting circuit 726 is provided so that the detecting time adapted to the respective endoscopes may be set and, in addition to setting the time by discriminating the scope, the operator may optionally set the detecting time. A least value detecting time more adapted to the endoscope to be connected to this apparatus can be set.

FIG. [22] *82* shows an example of the displaying panel of the apparatus of this embodiment.

In an endoscope, when the scope is discriminated by the scope discriminating circuit 724, the respective observed parts will be determined. Therefore, such observed parts can be displayed by an LED or the like on a displaying panel. An adjusting mechanism is provided on the panel so that the least value detecting time may be varied in response to the difference in the kind of the endoscope and picture angle even in the same observed part.

As described above, according to this embodiment, the part to be inspected can be discriminated by the scope, the least value detecting time corresponding to the movement can be set, the observer can optionally set this least value detecting time and therefore the optimum least value detecting time can be set in response to the object.

The other formation, operation and effect of this 22nd embodiment are the same as of the above mentioned 14th embodiment.

Figure 83:
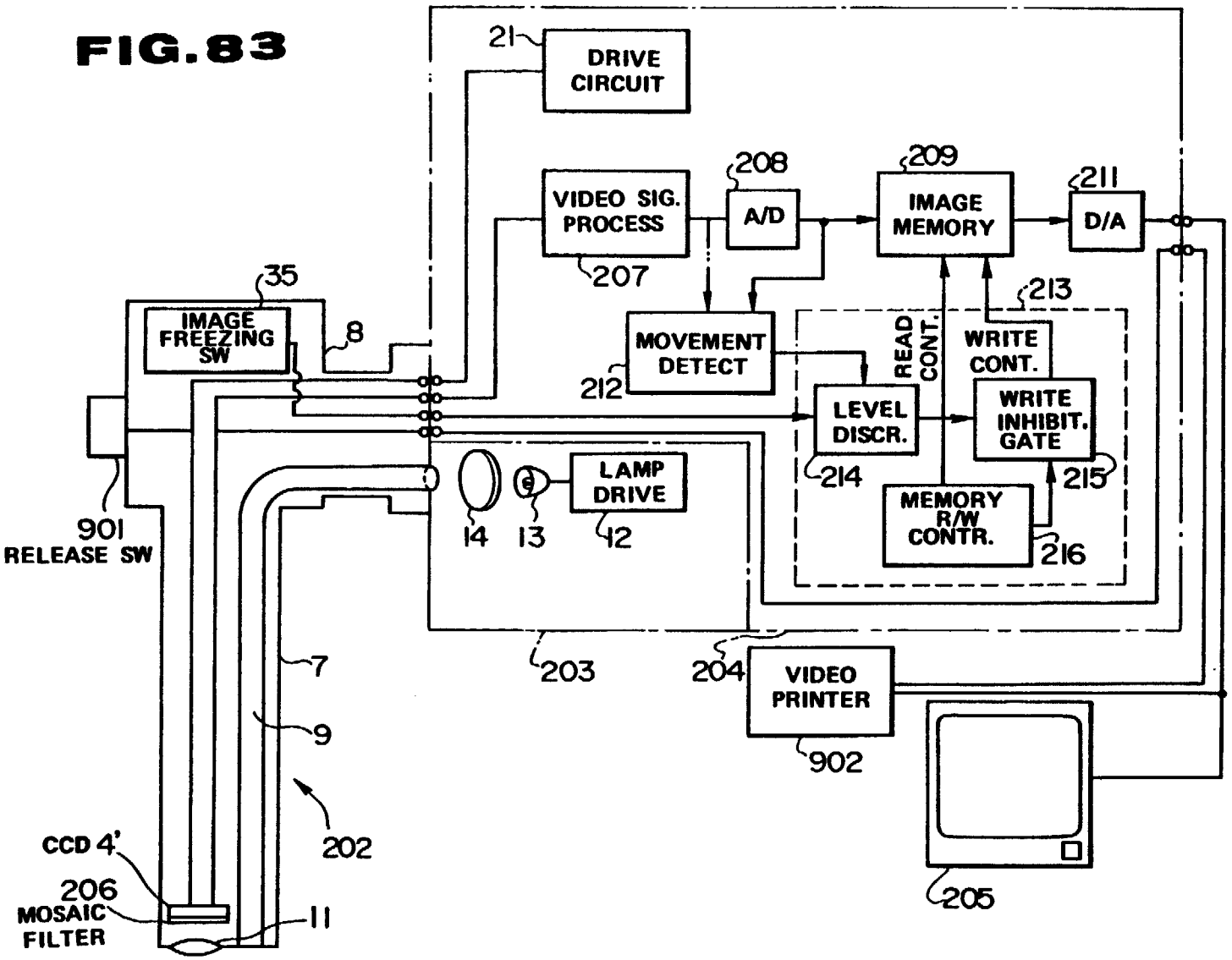
FIG. 83 is a block diagram showing the formation of the 23rd embodiment of the present invention.

FIG. 83 shows an essential part of the 23rd embodiment of the present invention. In this embodiment, a releasing directing means 901 is provided in the embodiment shown, for example, in FIG. 25 and, by this releasing directing means 901, the picture image displayed in the color monitor 205 can be printed out in a video printer 902.

The above mentioned releasing directing means 901 is provided, for example, in the operating part 8 of the electronic scope 202.

Figure 84:
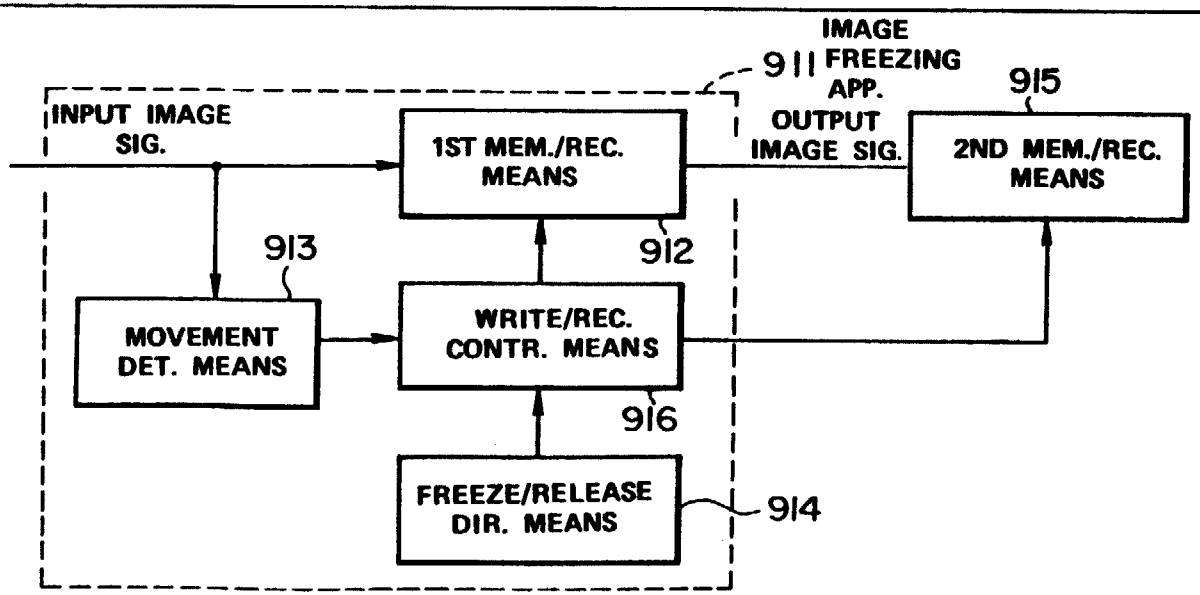
FIG. 84 is a block diagram showing the fundamental formation of an essential part of the 24th embodiment of the present invention.

FIG. 84 shows the fundamental formation of an essential part of the 24th embodiment of the present invention.

A picture image freezing apparatus 911 shown in FIG. 84 comprises a first memorizing/recording means 912 memorizing or recording input picture image signals, a movement detecting means 913 detecting the movement of an object from the above mentioned picture image signal, a freezing directing means 914 directing the above mentioned first memorizing/recording means 912 to memorize or record a frozen picture, a releasing directing means 914 directing a second memorizing/recording means 915 memorizing or recording a frozen picture memorized or recorded in the above mentioned first memorizing/recording means 912 to memorize or record a frozen picture, a first controlling means 916 controlling the operation of writing or recording picture image signals into the above mentioned first memorizing/recording means 912 in response to the output of the above mentioned movement detecting means 913 by the directing signal from the above mentioned freezing directing means or releasing directing means 914 and a second controlling means 916 controlling the operation of memorizing or recording frozen pictures into the above mentioned memorizing-/recording means 915 after the end of memorizing or recording frozen pictures into the above mentioned first memorizing/recording means 912 by the directing signal from the above mentioned releasing directing means 914. By the way, in FIG. 84, the freezing directing means and releasing directing means are shown integrally as a freezing/releasing directing means 914 and the first controlling means and second controlling means are shown integrally as a writing-in/recording controlling means 915.

In the above mentioned formation, when the first recording/memorizing means 912 is directed by the freezing directing means 914 to memorize or record a frozen picture, by the directing signal from this directing means 914, the first controlling means 916 will control the operation of writing/recording input picture image signals into the first memorizing /recording means 912 in response to the output of the movement detecting means 913 and the frozen picture will be memorized or recorded in this first memorizing/recording means 912.

On the other hand, when the second memorizing-/recording means 915 is directed by the releasing directing means 914 to memorize or record a frozen picture, by the directing signal from this directing means 914, the second controlling means 916 will control the operation of writing/recording input picture image signals into the first memorizing/recording means 912, the frozen picture will be memorized or recorded in this first memorizing/recording means 912 and, after the end of memorizing or recording the frozen picture into this first memorizing/recording means 912, the operation of memorizing or recording the frozen picture into the second memorizing/recording means 915 will be controlled and the frozen picture will be memorized or recorded in this second memorizing/recording means 915.

In the embodiment shown in FIG. 83, by the releasing direction, the picture image of the color monitor 205 is immediately printed out, whereas, in this embodiment, when the releasing is directed, first the releasing direction will be started, by this releasing direction, the frozen picture will be memorized in the first memorizing/recording means (the picture image memory 209 in FIG. 83) and then will be output to the second memorizing/recording means (the video printer in FIG. 83).

Figure 85:
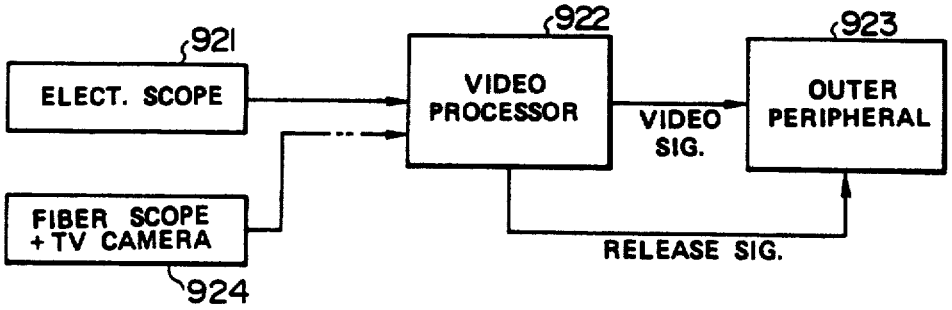
FIG. 85 is a block diagram showing a system formation in the 24th embodiment.

FIG. 85 is a block diagram showing the formation in FIG. 84. An electronic scope 921 outputs to a video processor 922 a picture image signal and freezing and releasing directing signals. This video processor 922 contains a signal processing means and light source means and outputs to an external recording apparatus 923 a picture image signal and releasing signal.

In this embodiment, a fiber scope 924 and television camera 925 can be used instead of the electronic scope 921.

Figure 86:
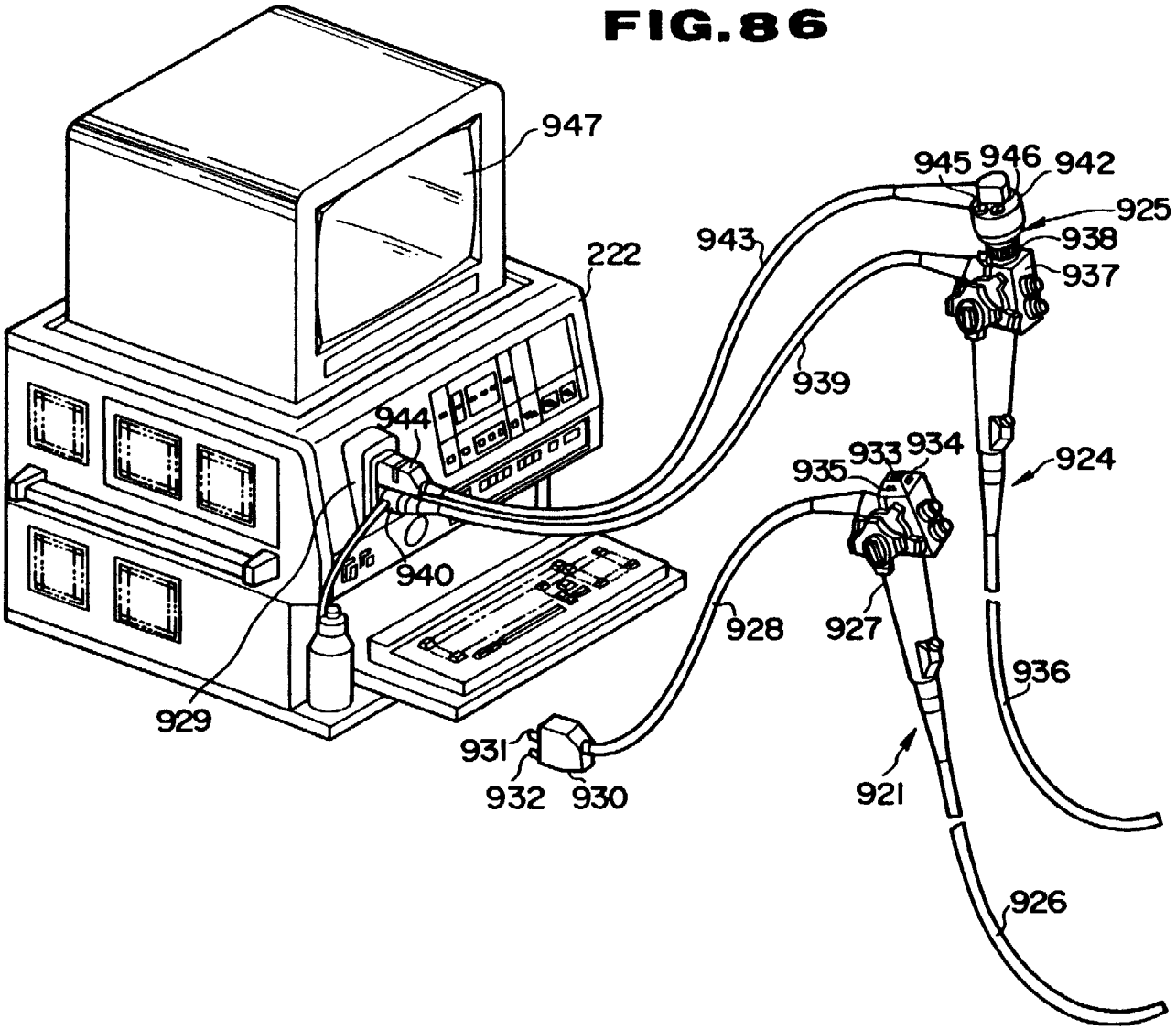
FIG. 86 is a perspective view showing the contours of an imaging means and video processor in the 24th embodiment.

FIG. 86 shows the electronic scope 921, the television camera 925 connected to the fiber scope 924 and the [contour] *general construction* of the video processor 922.

The television camera 925 fitted to the electronic scope 921 or fiber scope 924 can be connected to the above mentioned video processor 922.

This electronic scope 921 has an elongate and, for example, flexible insertable part 926 and a thick hand base operating part 927 connected to the rear end of this insertable part 926. A flexible universal cord 928 is extended sidewise from the above mentioned hand base operating part 927 and is provided at the end with a connector 930 removably connected to a connector receptacle 929 of the above mentioned video processor 922. This connector 930 is provided with an electric contact 931 and light guide connector 932.

The above mentioned hand base operating part 927 is provided with a freezing switch 933 which is a freezing directing means, a releasing switch 934 which is a releasing directing means and a VTR switch 935 controlling a VTR.

The above mentioned fiber scope 924 has an elongate and, for example, flexible insertable part 936 and a thick hand base operating part 937 connected to the rear end of this insertable part 936. This hand base operating part 937 is provided at the rear end with an eyepiece part 938. A flexible light guide cable 939 is extended sidewise from the above mentioned hand base operating part 937 and is provided at the end with a light guide connector 940 removably connected to a connector receptacle 929 of the above mentioned video processor 922.

The above mentioned television camera 925 has a camera body 942 fitted to the above mentioned eyepiece part 938, an electric cable 943 extended from this camera body 942 and a connector 944 provided at the end of this electric cable 943 and removably connected to the connector receptacle 929 of the above mentioned video processor. The camera body 942 is provided with a freezing switch 945 and releasing switch 946.

The above mentioned video processor 922 is connected with a color monitor 947 and displays a signal-processed color video in this color monitor 947.

Figure 87:
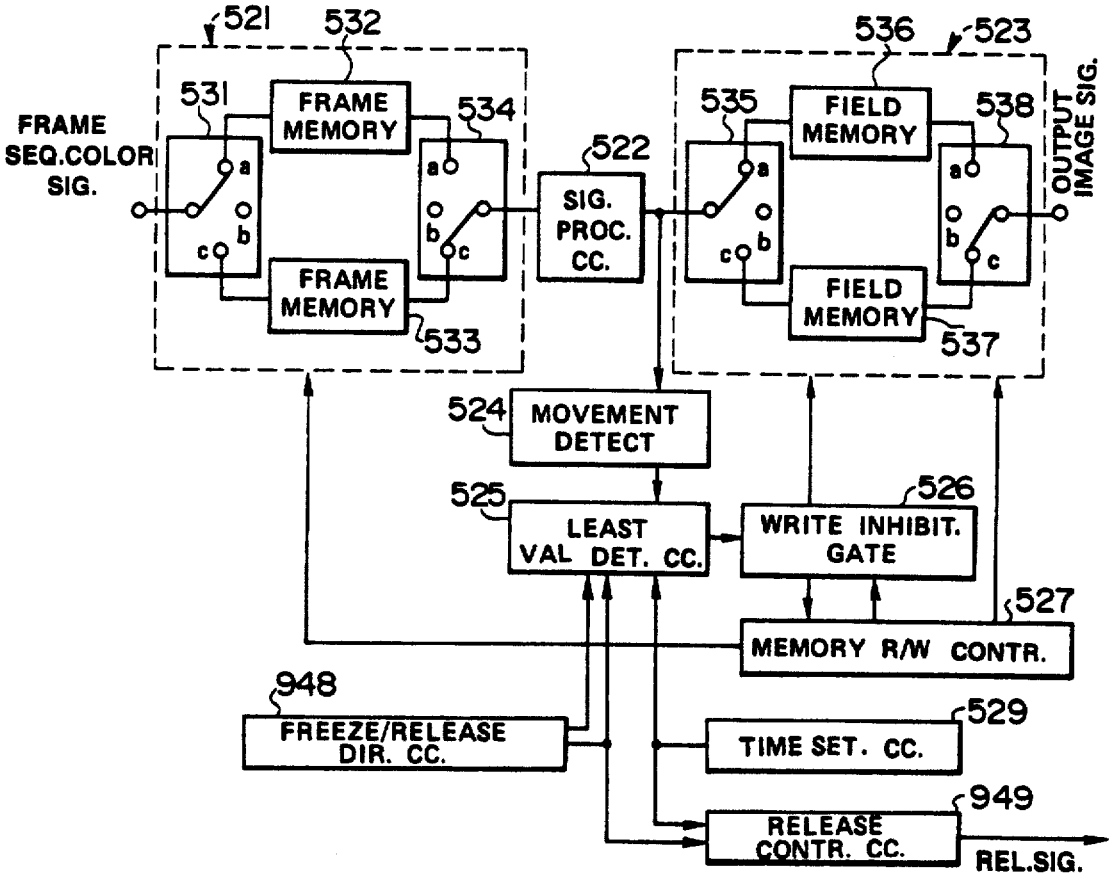
FIG. 87 is a block diagram showing the formation of a signal processing system in the 24th embodiment.

Now, a signal processing system within the video processor 922 is shown in FIG. 87.

This signal processing system is provided with a freezing/releasing directing circuit 948 outputting freezing and releasing directing signals instead of the freezing directing circuit 528, for example, in FIG. 52. This directing circuit 948 outputs a releasing directing signal to the least value detecting circuit 525. The releasing directing signal is input into the least value detecting circuit 525 and a releasing controlling circuit 949. The output signal of the set time detecting circuit 529 is input into the least value detecting circuit 525 and releasing controlling circuit 949.

The [others] *other components* are of the same formation as in the above mentioned FIG. 52.

This embodiment is the same as the embodiment in FIG. 52 as regards the freezing operation.

On the other hand, in case a releasing directing signal is output from the above mentioned freezing/releasing directing circuit 948, with the above mentioned freezing operation, the releasing controlling circuit 949 will output a releasing signal after the time set by the set time detecting circuit 529, that is, after the above mentioned freezing operation ends. The external recording apparatus 923 receives this releasing signal and records the output picture image signal of the video processor 922, that is, the frozen picture image at the time when the movement of the object is the least.

Thus, according to this embodiment, the picture image at the time when the movement of the object is the least can be frozen and a frozen picture little in such deterioration as the color smear or image fogging caused by the movement of the object can be recorded. Further, this frozen picture having little picture quality deterioration can be recorded in the external recording apparatus 923.

Figure 88:
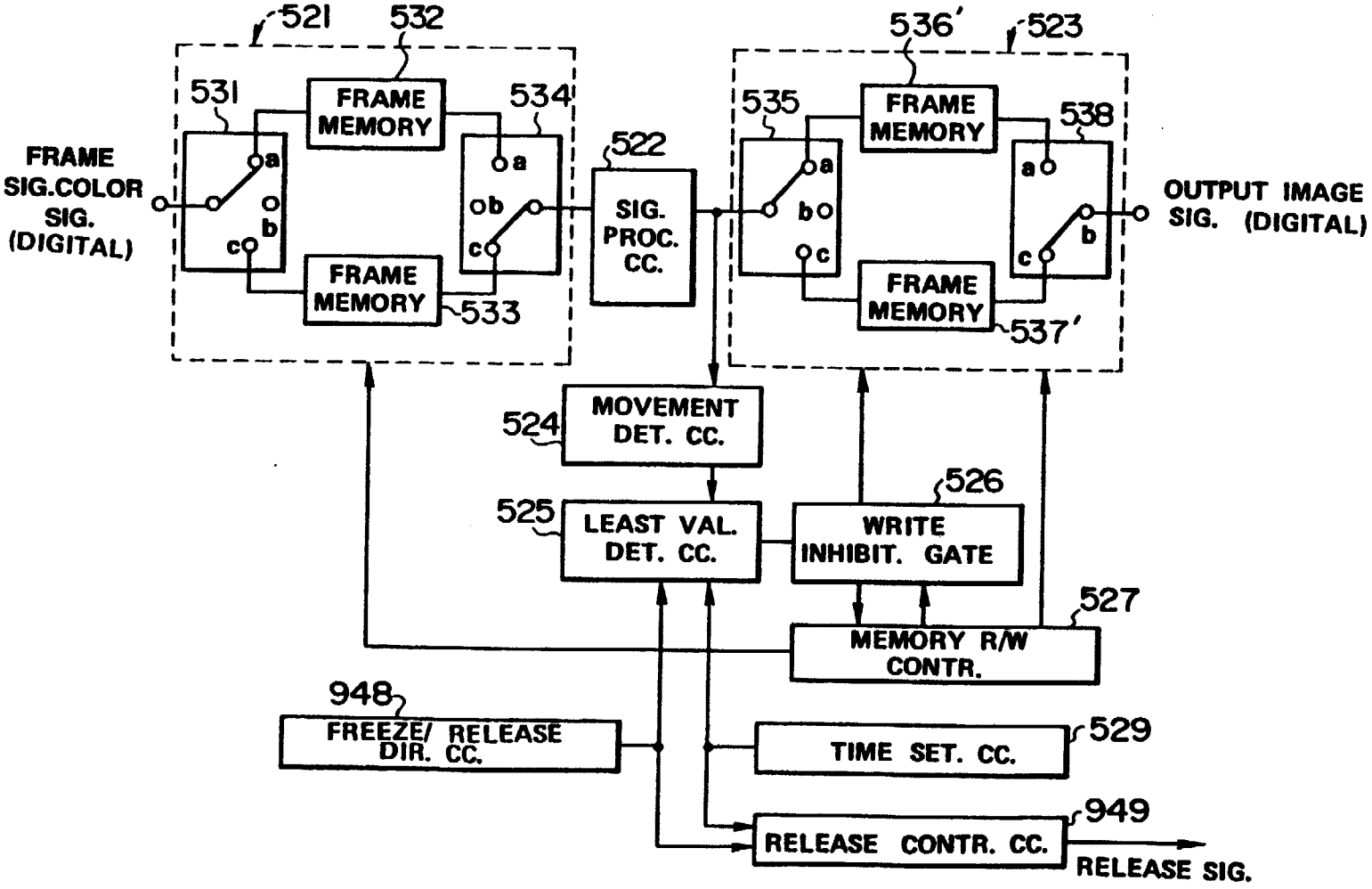
FIG. 88 is a block diagram showing the formation of a signal processing system in a modification of the 24th embodiment.

FIG. 88 shows a signal processing system of a modification of the 24th embodiment. In this signal processing system, the freezing memory 523 in FIG. 87 is formed of frame memories 536' and 537' and the [others] *other components* are the same and shall not be explained here.

Figure 89:
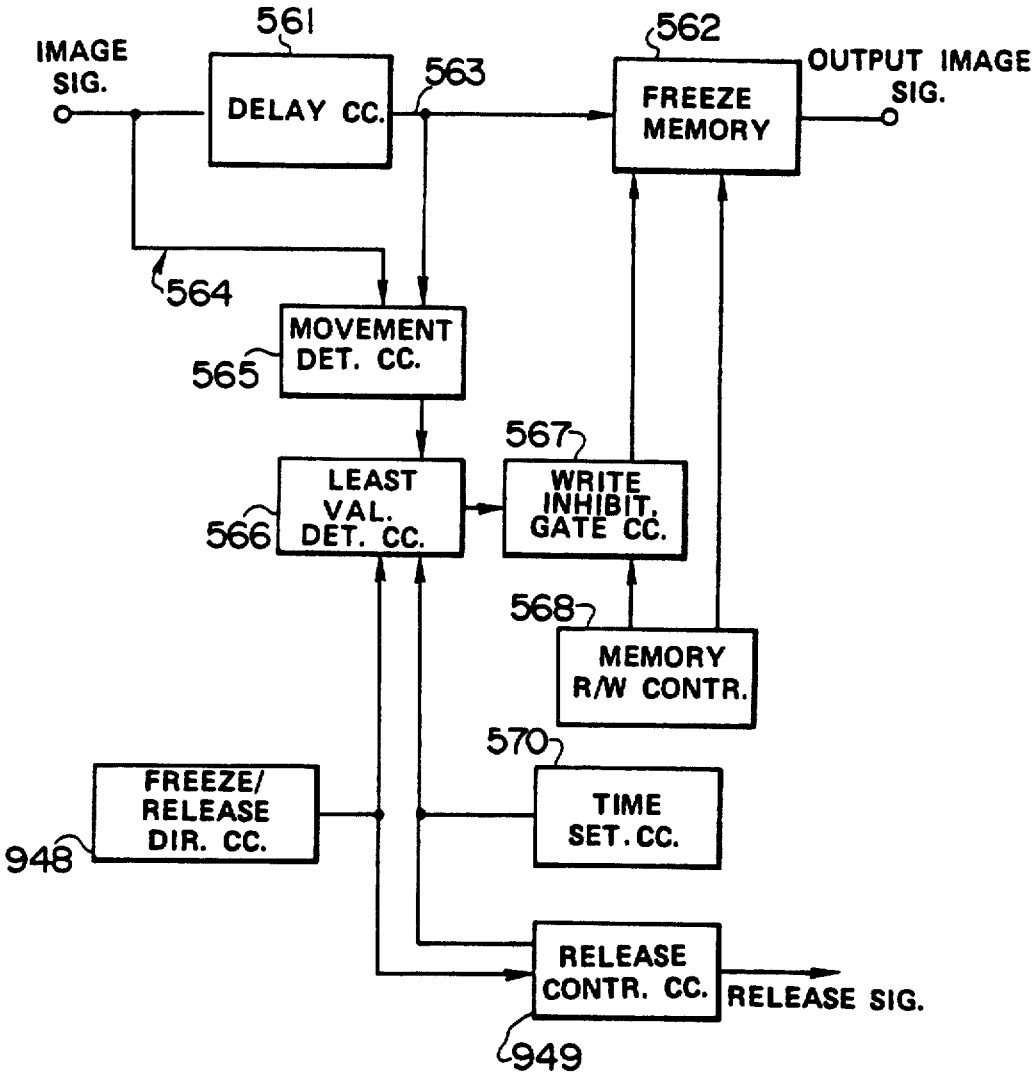
FIG. 89 is a block diagram showing the formation of a signal processing system in the 25th embodiment of the present invention.

In FIG. 87 or 88, a frame sequential type signal processing system has been explained. In the 25th embodiment shown in FIG. 89, an example of a simultaneous type signal processing system is shown.

In this embodiment, the releasing/freezing directing circuit 948 is used instead of the releasing directing circuit 569 in FIG. 58 and further the releasing controlling circuit 949 is provided.

As the signal processing system is of the simultaneous type, the operation of outputting the releasing signal of the releasing controlling circuit 949 by the operation of the releasing direction is the same as in the above described embodiment and shall not be explained here.

Figure 90:
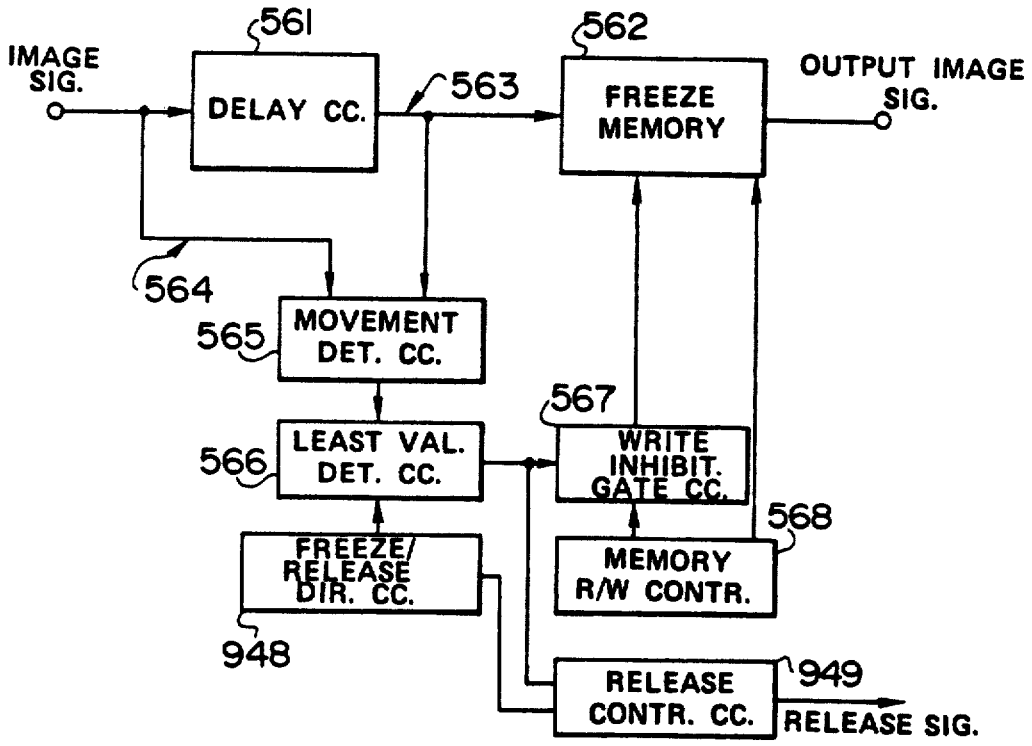
FIG. 90 is a block diagram showing the formation of a signal processing system in the 26th embodiment of the present invention.

FIG. 90 shows a signal processing system of the 26th embodiment of the present invention. In this embodiment, the freezing/releasing directing circuit 948 is used instead of the freezing directing circuit 569 in FIG. 59 and the releasing controlling circuit 949 is provided.

The operation by directing freezing is the same as in FIG. 59 and the operation by directing releasing is the same as is described above. That is to say, after the freezing operation is made, a releasing signal will be output from the releasing controlling circuit 949.

Figure 91:
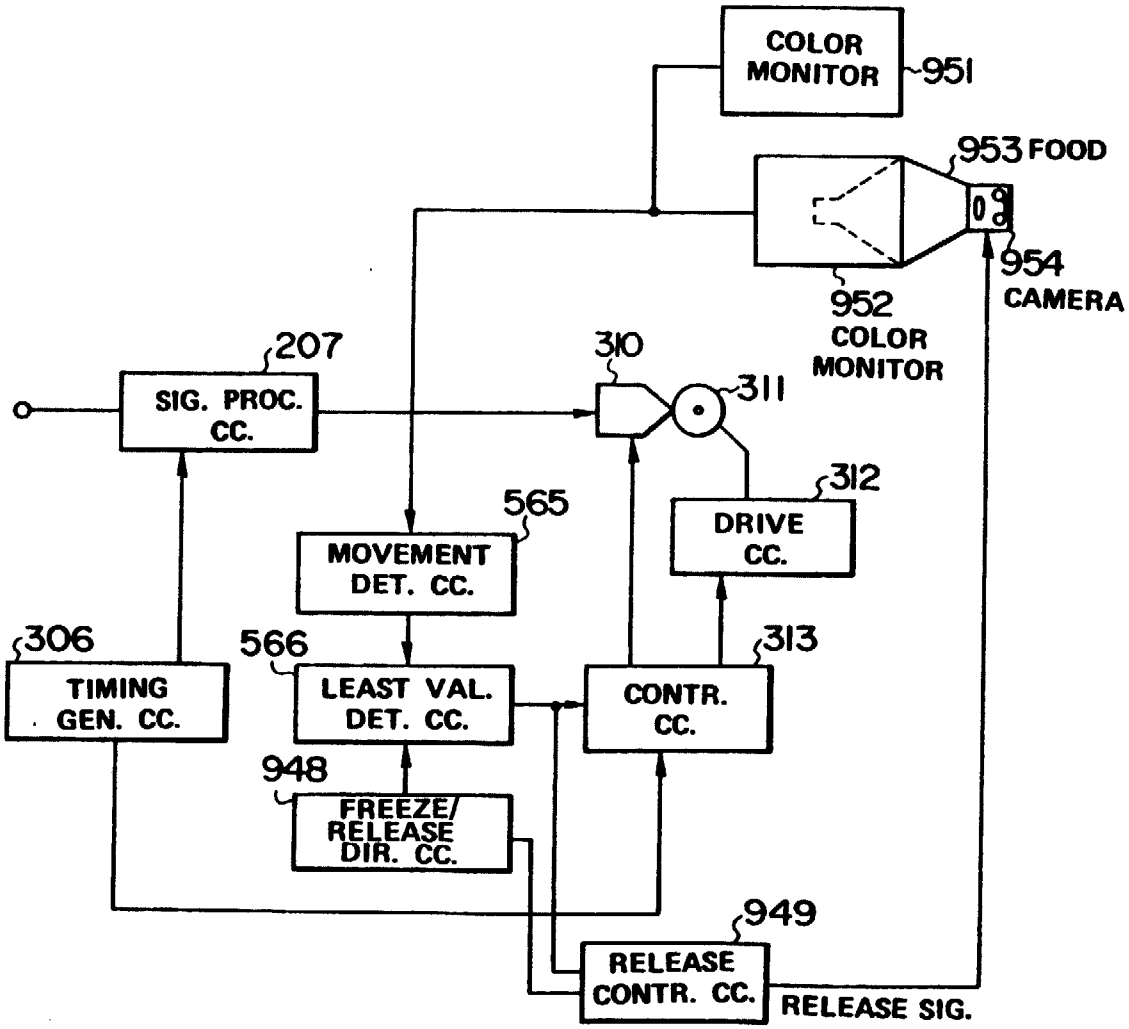
FIG. 91 is a block diagram showing the formation of an essential part of the 27th embodiment of the present invention.

FIG. 91 shows an essential part of the 27th embodiment of the present invention. In this embodiment, the freezing/releasing directing circuit 948 is used instead of the releasing directing circuit 569 in FIG. 61 and the releasing controlling circuit 949 is provided.

By the way, in this embodiment, the output of the signal processing circuit 207 is color-displayed in the color monitor 951 and the frozen picture displayed in the color monitor 952 can be color-photographed by transmitting a releasing signal to the photographing apparatus (still camera) 954 fitted to the monitor surface of the other color monitor 952 through the hood 953.

By the way, it is apparent that the freezing/releasing directing means and releasing controlling means can be applied to the other embodiments.

Figure 92:
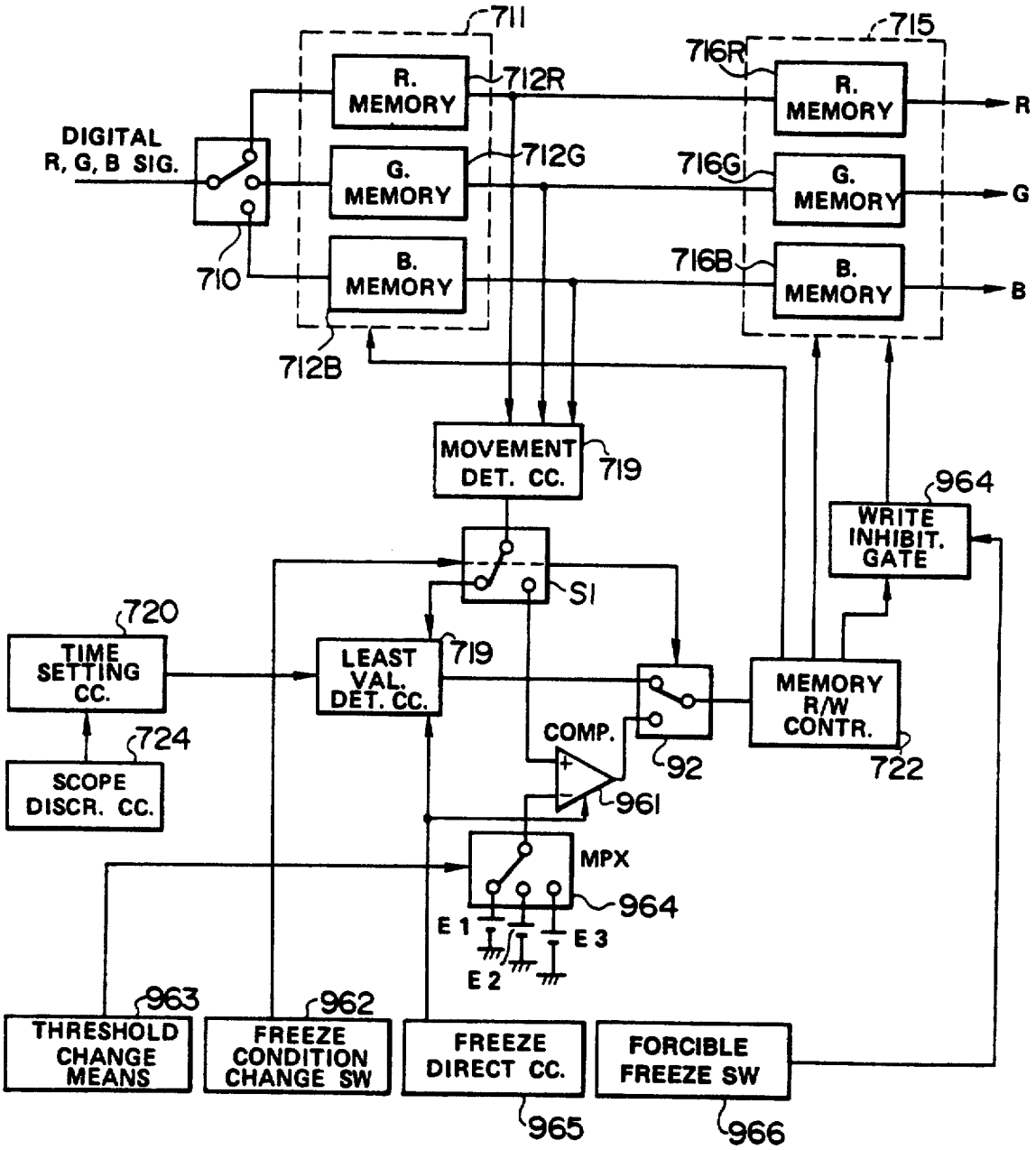
FIG. 92 is a block diagram showing the formation of an essential part of the 28th embodiment of the present invention.

FIG. 92 shows an essential part of the 28th embodiment of the present invention. In this embodiment, the condition of taking in the frozen picture in FIG. 66 can be met by either of the least value detection and threshold value detection. That is to say, the output of the movement detecting circuit 719 can be input into the least value detecting circuit 721 and threshold value circuit 961 through a switch S1 which can be selected by a freezing condition changing means 962.

In the above mentioned least value detecting circuit 719, the time of detecting the least value can be set by the time setting circuit 720. On the other hand, in the threshold value circuit 961, the threshold values E1, E2 and E3 can be selected by the threshold value changing means 963 through the multiplexer 964.

The output of the above mentioned least value detecting circuit 719 and the output of the threshold value circuit 961 are input into the memory R/W controller 722 through a switch S2 switched as operatively connected with the switch S1. In this memory R/W controller 722, when a signal meeting the freezing condition is input through the switch S2, a writing-in inhibiting signal will be output to the memory 715 through the writing-in inhibiting gate circuit 964 and the subsequent writing-in will be inhibited. When the freezing directing switch 965 is operated, the switches S1 and S2 will be switched on by the freezing condition changing means 962. When a judging signal meeting the condition is output by the least value detecting circuit 719 or threshold value circuit 961, the frozen picture image will be held in the memory 715.

Also, in this embodiment, a forcible freezing switch 966 is provided and, when this switch 966 is operated, the writing-in inhibiting gate circuit 964 will output a signal forcibly holding the frozen picture image in the memory 715.

By the way, it is apparent that many different embodiments can be formed by partly combining the above described respective embodiments. Such embodiments also fall under the present invention.

What is claimed is:

1. An electronic endoscope system comprising:

an electronic endoscope provided with an elongate insertable part, an objective optical system provided on [the] *a* tip side of said insertable part and forming an image of an object, an imaging device *having an imaging surface for* photoelectrically converting the image based on said objective optical system and an illuminating light emitting means emitting an illuminating light from the tip side of said insertable part;

a driving signal outputting means *for* outputting a driving signal [outputting] *to said imaging device and causing said imaging device to output* a picture image signal [from said imaging device];

a video signal processing means *for* producing a video signal from said picture image signal;

a displaying means *for* displaying said video signal on a monitor picture surface;

a picture image [recording] *memorizing* means which can write-in/read-out said picture image signal or said video signal;

a movement detecting means whereby picture image signals imaged by said imaging device at different times are input and the movement amounts of the respective picture image signals are detected;

a frozen picture memory judging means *for* judging whether said movement amount detected by said movement detecting means [is adapted] *corresponds* to [the] *a* frozen picture memorizing condition or not;

a frozen picture memorizing signal outputting means *for* outputting a control signal [making] *and causing* said picture image memorizing means *to* hold the picture image signal of the frozen picture [by the] *in response to a* judging signal [judged] *outputted* by said judging means [to be adapted to said memorizing condition]; and a frozen picture directing means *for* directing the memorization of the frozen picture [adapted] *corresponding* to said memorizing condition.

2. An electronic endoscope system according to claim 1 wherein said frozen picture [memorization] *memory* judging means [has a] *comprises* least movement amount detecting means [by which the] *for detecting a* least or minimum movement amount of the movement detecting signal [of the] *from* respective picture image signals input from said movement detecting means [is made], *said least movement amount indicating* a frozen picture memory memorizing condition, and [and a] *further comprising* threshold value comparing means [by which the case that] *for comparing* the movement detecting signals input from said movement detecting means *with a threshold value, wherein when said movement detecting signals* are within [the] *said* threshold value [is made], a frozen picture memory memorizing condition *is indicated.*

3. An electronic endoscope system according to claim 1 wherein said frozen picture directing means [is formed of] *comprises* a switch provided in said electronic endoscope.

4. An electronic endoscope system according to claim 1 wherein said frozen picture directing means [is] *comprises* a foot switch.

5. An electronic endoscope system according to claim 3 or 4 wherein said frozen picture [memorization] *memory* judging means [has a] *comprises* memorizing condition changing means [making it possible to change] *for changing* said memorizing condition.

6. An electronic endoscope system according to any one of claims 1, 3 and 4 wherein said movement detecting means detects the movement amount by detecting [the size] *a magnitude* of [the] *a* time correlation amount between [the] picture image signals imaged at respectively different times.

7. An electronic endoscope system according to any one of claims 1, 3 and 4 further [having a] *comprising* forcible frozen picture directing means [forcibly making] *for forcing* said picture image [recording] *memorizing* means [record] *to hold* not only the output signal from said judging means but also the picture image signal by one field/frame as a frozen picture.

8. An electronic endoscope system according to any one of claims 1, 3 and 4 wherein said picture image memorizing means [has a] *comprises* delaying means *for* delaying [the picture image] *an* input *of the picture image* for [the] *a* time exceeding the time required to detect [the] *a* size of the movement [amount] *amounts detected* by said movement detecting means.

9. An electronic endoscope system according to any one of claims 1, 3 and 4 wherein said movement detecting means detects movement amounts in [the] picture image signals imaged at the same time.

10. An electronic endoscope system according to claim 9 wherein said movement detecting means [is formed of a] *comprises extracting* means [of] *for* extracting high band components of spatial frequencies in the picture image signal.

11. An electronic endoscope system according to any one of claims 1, 3 and 4 wherein said frozen picture [memorization] *memory* judging means compares said movement amounts in a plurality of picture image signals and judges [the] *a* least or minimum movement amount [to be adapted] *corresponding* to the memorizing condition.

12. An electronic endoscope system according to claim 11 wherein said picture image memorizing means [has] *comprises* a plurality of picture image [memories] *memory means for* respectively memorizing a plurality of color picture images.

13. An electronic endoscope system according to claim 12 wherein said movement detecting means [judges] *determines from* a picture image signal [in which the] *having a least or minimum* movement amount [is the least or minimum in] *from among* said plurality of picture image memories.

14. An electronic endoscope system according to any one of claims 1, 3 and 4 wherein said frozen picture image memorization judging means [is a] *comprises* threshold value outputting means *for* outputting a threshold value [in] *within* an allowable range of the size of the movement amount [as said] *so that when said movement amount is within said allowable range, the movement amount corresponds to said* memorizing condition.

15. An electronic endoscope system according to claim 14 wherein said threshold value outputting means

[can vary] *comprises means for varying* said threshold value.

16. An electronic endoscope system according to claim 14, wherein said frozen picture memorizing controlling means [has] *comprises* a timer, *said timer being* started by a directing signal [by] *output from* said frozen picture memorizing directing means and [forcibly] *wherein said frozen picture memorizing directing means* outputs a frozen picture writing-in signal to said picture image memorizing means after the time set by said timer.

17. An electronic endoscope system according to any one of claims 1, 3 and 4 further [having a] *comprising* picture image recording means *for* recording a picture image signal corresponding to the frozen picture memorized in said picture image memorizing means.

18. An electronic endoscope system according to claim [19] *17* wherein said picture image [memorizing] *recording* means [is] *comprises* any one of a video printer, video disc and video tape recorder.

19. An electronic endoscope system according to claim 17 further [having a] *comprising* releasing directing means [making] *for outputting a releasing directing signal and directing* said picture image recording means *to* record the picture image of said picture image memorizing means.

20. An electronic endoscope system according to claim 19 further [having a] *comprising* releasing controlling means *for outputting a releasing signal to said picture image recording means,* wherein the releasing directing signal from said releasing directing means is input and, after the memorization of the frozen picture in said picture image memorizing means ends, [a] *said* releasing signal is output to said picture image recording means.

21. An electronic endoscope system according to claim 1 wherein said frozen picture [memorization] *memory* judging means [has a] *comprises* memorizing condition changing means [making it possible to change] *for changing* said memorizing condition.

22. An electronic endoscope system according to claim 21 wherein said memorizing condition changing means [can] *comprises means for* manually [change] *changing* the memorizing condition.

23. An electronic endoscope system according to claim 21 wherein said memorizing condition changing means is set at the least value of the size of a plurality of movement amounts output for [the] respective picture image signals from said movement detecting means.

24. An electronic endoscope system according to claim 21 wherein said memorizing condition changing means renews the memorizing condition by the size of the movement amount in the case that said changing means judges the movement amount to [be adapted] *correspond* to said memorizing condition at that time.

25. An electronic endoscope system according to claim 24 wherein said memorizing condition changing means [is formed of] *comprises* a digital circuit.

26. An electronic endoscope system according to claim 24 wherein said memorizing condition changing means [is formed of] *comprises* analogue circuit.

27. An electronic endoscope system according to claim 24 wherein said memorizing condition changing means [has a] *comprises* renewing operation time setting means *for* determining [the] *an* operation time [of] *for* renewing said memorizing condition.

28. An electronic endoscope system according to claim 27 wherein said renewing operation time setting means [has a] *comprises* scope discriminating means *for* discriminating the electronic endoscope to be connected and *for* automatically [sets] *setting* said operation time [by the] *response to an* output signal [of] *from* said scope discriminating means.

29. An electronic endoscope system according to claim 27 wherein said renewing operation time setting means [is] *comprises* a timer.

30. An electronic endoscope system according to claim 29 wherein said timer [can] variably [set] *sets* the time [of making] *for effecting* said renewing operation.

31. An electronic endoscope system according to any one of claims 1, 3, 4, or 21 wherein said movement detecting means detects [the] *a* movement amount within the picture image region of the picture image signal imaged by said imaging device.

32. An electronic endoscope system according to claim 31 wherein said movement detecting means detects the movement amount within [the] *a part of said* picture image region [of a part of said picture image region].

33. An electronic endoscope system according to claim 32 further [having a] *comprising* region varying means [which can] *for varying* vary the picture image region of said [one] part [detecting the movement amount] *of said picture image region.*

34. An electronic endoscope system according to any one of claims 1, 3, 4, or 21 wherein said illuminating light emitting means [is formed of] *comprises* a light guide *means for* transmitting an illuminating light fed to one end surface *thereof* and emitting [it] *the illuminating light* from [the other] *another* end surface arranged on the tip side of said insertable part [and] *of* said light guide [can be held at] *and wherein* said one end *is releasably held* by a light source means outputting the illuminating light.

35. An electronic endoscope system according to claim 34 wherein said light source means [is a] *comprises* sequential light outputting means *for* time-sequentially outputting illuminating lights of respectively different wavelength ranges.

36. An electronic endoscope system according to claim 35 wherein said imaging device has a color separating color filter in front of [its] *said* imaging surface.

37. An electronic endoscope system according to claim 35 wherein said movement detecting means [is a] *comprises* color smear detecting means *for* detecting [the size] *a magnitude* of [the] *a* time-correlation amount for the picture image signal components of respectively different wavelength bands imaged at different times and forming [the] color picture images of one field/frame.

38. An electronic endoscope system according to claim 37 wherein said movement detecting means [has a] *comprises* signal level standardizing means *for* arranging the levels in [the] one field/frame period [of] *from* a plurality of picture image signal components having [the size] *said magnitude* of the [correlation] *time-correlation* amount detected.

39. An electronic endoscope system according to claim 37 wherein said picture image signal components of respectively different wavelength bands are imaged in the wavelength band of at least one of [the] respective wavelength bands of red, green and blue.

40. An electronic endoscope system according to claim 34 wherein said light source means [is a] *com-*

*prises* white light outputting means *for* outputting a white light.

41. An electronic endoscope system according to claim 40 wherein said movement detecting means detects [the size] *a magnitude* of [the] *a* correlation amount between [the] picture image signal components of respectively different wavelength bands forming a color picture image of one field/frame.

42. An electronic endoscope system according to claim 40 wherein said imaging device has a color separating color filter in front of [its] *said* imaging surface.

43. An electronic endoscope system according to claim [41] *42* wherein said electronic endoscope [is] *comprises* an electronic scope in which said imaging device is arranged in [the] *a* focal plane of said objective optical system.

44. An electronic endoscope system according to claim 42 wherein said electronic endoscope [is] *comprises* a scope externally fitted with a television camera and [formed of] *further comprising* a fiber scope arranged on one end surface in [the] *a* focal plane of said objective optical system and having an optical image transmitting image guide means on the other end surface *thereof*, an image forming optical system fittable [as opposed to] *adjacent* said other end surface of said fiber scope and forming said optical image transmitted to said other end surface and a television camera [unit] *means for* photoelectrically converting the optical image *formed* by said image forming optical system.

45. An electronic endoscope system according to claim 42 wherein said picture image memorizing means [is] *comprises* a semiconductor memory *means for* memorizing color picture image signals at least of one field/frame.

46. An electronic endoscope system according to claim 45 wherein said frozen picture memorizing signal outputting means [has a] *comprises* memory writing/-reading controlling [function whereby, in case] *means for controlling said memory such that in the event* an adaptation judging signal [adapted] *corresponding* to said memorizing condition is not input from said frozen picture judging means, a memory writing signal *for effecting* writing *of* the color picture image signal of one field/frame *and* input into said semiconductor memory is output and a memory reading signal *for effecting reading out of* the color picture image signal written in before one field/frame is output.

47. An electronic endoscope system according to claim 46 *further comprising first and second semiconductor memories* wherein said frozen picture memorizing means outputs a frozen picture memorizing signal [making] *for inactivating* said memory writing signal [inactive on] *in* said first or second semiconductor memory when said adaptation judging signal is input.

48. An electronic endoscope system according to claim 42 wherein said movement detecting means [is a] *comprises* color smear detecting means *for* detecting [the size] *a magnitude* of [the] *a* time-correlation amount between the picture image signal components having a common wavelength band in a plurality of color picture images imaged at different times.

49. An electronic endoscope system according to claim 48 wherein said color smear detecting means detects the [size] *magnitude* of the time-correlation amount between the picture image signal components imaged only in a common wavelength band.

50. An electronic endoscope system according to claim 48 wherein said picture image signal components having [the] *a* common wavelength band are imaged in the wavelength band of at least one of the wavelengths of red, green and blue.

51. An electronic endoscope system according to claim 48 wherein said picture image signal components having [the] *a* common wavelength band form at least one of a luminance signal and color difference signal.

*52. An electronic endoscope system comprising:*

*an electronic endoscope provided with an elongate insertable part, an objective optical system provided on a tip side of said insertable part and forming an image of an object, an imaging device having an imaging surface for photoelectrically converting the image based on said objective optical system and an illuminating light emitting means emitting an illuminating light from the tip side of said insertable part;*

*a driving signal outputting means for outputting a driving signal to said imaging device and causing said imaging device to output a picture image signal;*

*a video signal processing means for producing a video signal from said picture image signal;*

*a displaying means for displaying said video signal on a monitor;*

*a picture image memorizing means which can write-in/read-out said picture image signal or said video signal;*

*a movement detecting means whereby a picture image signal imaged by said imaging device is input and the movement signal is detected;*

*a frozen picture memory judging means for judging whether said movement amount detected by said movement detecting means corresponds to a frozen picture memorizing condition or not;*

*a frozen picture memorizing signal outputting means for outputting a control signal and causing said picture image memorizing means to hold the picture image signal of the frozen picture in response to a judging signal outputted by said judging means; and*

*a frozen picture directing means for directing the memorization of the frozen picture corresponding to said memorizing condition.*

*53. An electronic endoscope system according to claim 52 wherein said frozen picture directing means comprises a switch provided in said electronic endoscope.*

*54. An electronic endoscope system according to claim 52 wherein said frozen picture directing means comprises a foot switch.*

*55. An electronic endoscope system according to claim 52 further comprising forcible frozen picture directing means for forcing said picture image memorizing means to hold not only the output signal from said judging means but also the picture image signal by one field/frame as a frozen picture.*

*56. An electronic endoscope system according to claim 52 wherein said movement detecting means detects a movement amount by self-correlating an imaged picture image signal.*

*57. An electronic endoscope system according to claim 56 wherein said movement detecting means comprises means for extracting high band components of spatial frequencies in the picture image signal.*

*58. An electronic endoscope system according to claim 52, wherein said frozen picture memory judging means compares said movement amount in a plurality of picture image signals and judges the least or minimum movement amount corresponding to the memorizing condition.*

*59. An electronic endoscope system according to claim 52 wherein said frozen picture image memorization judg-*

*ing means comprises threshold value outputting means for outputting a threshold value within an allowable range of the size of the movement amount so that when said movement amount is within said allowable range, the movement amount corresponds to said memorizing condition.*

*60. An electronic endoscope system according to claim 59 wherein said threshold value outputting means comprises means for varying said threshold value.*

*61. An electronic endoscope system according to claim 52 wherein said frozen picture memory judging means comprises memorizing condition changing means for changing said memorizing condition.*

*62. An electronic endoscope system according to claim 61 wherein said memorizing condition changing means comprises means for manually changing the memorizing condition.*

*63. An electronic endoscope system according to claim 61 wherein said memorizing condition changing means is set at the least value of the size of a plurality of movement amount output for respective picture image signals from said movement detecting means.*

*64. An electronic endoscope according to claim 61 wherein said memorizing condition changing means renews the memorizing condition by the size of the movement amount in the case that said changing means judges the movement amount to correspond to said memorizing condition at that time.*

*65. An electronic endoscope system according to claim 64 wherein said memorizing condition changing means comprises renewing operation time setting means for determining an operation time for renewing said memorizing condition.*

*66. An electronic endoscope system according to claim 65 whereins said renewing operation time setting means comprises a timer.*

*67. An electronic endoscope system according to claim 66 wherein said timer variably sets the time for effecting said renewing operation.*

*68. An electronic endoscope system according to claim 52 wherein said movement detecting means detects a movement amount within a picture image region of the picture image signal image by said imaging device.*

*69. An electronic endoscope system according to claim 68 wherein said movement detecting means detects the movement amount within a part of said picture image region.*

*70. An electronic endoscope system according to claim 52 wherein said electronic endoscope comprises a scope externally fitted with a television camera and further comprising a fiber scope arranged on one end surface in a focal plane of said objective optical system and having an optical image transmitting image guide means on the other end surface thereof, an image forming optical system fittable adjacent said other end surface of said fiber scope and forming said optical image transmitted to said other end surface and a television camera means for photoelectrically converting the optical image formed by said image forming optical system.*

* * * * *

UNITED STATES PATENT AND TRADEMARK OFFICE
CERTIFICATE OF CORRECTION

PATENT NO.: Re. 34,504
DATED : January 11, 1994
INVENTOR(S): UEHARA et al.

It is certified that error appears in the above-identified patent and that said Letters Patent is hereby corrected as shown below:

On the title page, Item [75], the second inventor's name "Mashide Kanno" should be -- Masahide Kanno --.

Signed and Sealed this

Fourth Day of October, 1994

*Attest:*

*Attesting Officer*

BRUCE LEHMAN

*Commissioner of Patents and Trademarks*